US011324526B2

(12) United States Patent
Yurek

(10) Patent No.: US 11,324,526 B2
(45) Date of Patent: May 10, 2022

(54) DEVICES AND METHODS FOR MINIMALLY INVASIVE KIDNEY STONE REMOVAL BY COMBINED ASPIRATION AND IRRIGATION

(71) Applicant: CALYXO, INC., Pleasanton, CA (US)

(72) Inventor: Matthew Yurek, San Diego, CA (US)

(73) Assignee: CALYXO, INC., Pleasanton, CA (US)

( * ) Notice: Subject to any disclaimer, the term of this patent is extended or adjusted under 35 U.S.C. 154(b) by 0 days.

(21) Appl. No.: 17/489,733

(22) Filed: Sep. 29, 2021

(65) Prior Publication Data

US 2022/0087698 A1 Mar. 24, 2022

Related U.S. Application Data

(63) Continuation of application No. 16/966,856, filed as application No. PCT/US2019/016172 on Jan. 31, 2019.

(Continued)

(51) Int. Cl.
*A61B 17/221* (2006.01)
*A61M 25/00* (2006.01)
(Continued)

(52) U.S. Cl.
CPC ......... *A61B 17/221* (2013.01); *A61M 25/003* (2013.01); *A61B 2017/22079* (2013.01);
(Continued)

(58) Field of Classification Search
CPC ........ A61B 17/221; A61B 2017/22079; A61B 2217/007; A61M 25/003; A61M 2210/1082
See application file for complete search history.

(56) References Cited

U.S. PATENT DOCUMENTS 3,065,749 A 11/1962 Brass
3,749,090 A 7/1973 Stewart
(Continued)

FOREIGN PATENT DOCUMENTS

CN 203776869 U 8/2014
CN 203776946 U 8/2014
(Continued)

OTHER PUBLICATIONS

Communication dated Oct. 26, 2021 forwarding the extended European Search Report for European Patent Application No. 19746731.9, 12 pages.
(Continued)

*Primary Examiner* — Bradley J Osinski
(74) *Attorney, Agent, or Firm* — Squire Patton Boggs (US) LLP

(57) ABSTRACT

Disclosed herein are systems, devices, and methods for the removal of objects from the body. The device may be a urethral catheter configured to aspirate kidney stones from the urinary tract through one or more aspiration ports at the distal face or along a lateral side of the catheter. The catheter may include one or more irrigation ports at the distal face or along the lateral side of the catheter for dislodging kidney stones. The device may be steerable. The spatial arrangement of the one or more irrigation ports with respect to the one or more aspiration ports may vary. The device may include an irrigation tube and/or a shield member configured to spatially confine the kidney stones adjacent the catheter. Various temporal patterns of aspiration and irrigation are disclosed for optimizing removal of kidney stones.

20 Claims, 29 Drawing Sheets

Related U.S. Application Data

(60) Provisional application No. 62/649,430, filed on Mar. 28, 2018, provisional application No. 62/625,766, filed on Feb. 2, 2018.

(51) Int. Cl.
    *A61B 90/00*    (2016.01)
    *A61B 17/22*    (2006.01)

(52) U.S. Cl.
    CPC ... *A61B 2090/376* (2016.02); *A61B 2217/007* (2013.01); *A61M 2210/1082* (2013.01); *A61M 2210/1085* (2013.01); *A61M 2210/1089* (2013.01)

(56) References Cited

U.S. PATENT DOCUMENTS

| | | |
|---|---|---|
| 3,830,240 A | 8/1974 | Antonevich et al. |
| 4,215,476 A | 8/1980 | Armstrong |
| 4,630,598 A | 12/1986 | Bonnett |
| 4,680,026 A | 7/1987 | Weightman et al. |
| 4,706,656 A | 11/1987 | Kuboto |
| 4,708,717 A | 11/1987 | Deane et al. |
| 4,802,461 A | 2/1989 | Cho |
| 4,874,360 A | 10/1989 | Goldberg et al. |
| 4,941,872 A | 7/1990 | Felix et al. |
| 5,057,080 A | 10/1991 | Takahashi |
| 5,120,305 A | 6/1992 | Boehringer et al. |
| 5,226,885 A | 7/1993 | Takahashi |
| 5,265,840 A | 11/1993 | Gillespie et al. |
| 5,273,524 A | 12/1993 | Fox et al. |
| 5,295,956 A | 3/1994 | Bales et al. |
| 5,312,327 A | 5/1994 | Bales et al. |
| 5,312,332 A | 5/1994 | Bales et al. |
| 5,312,400 A | 5/1994 | Bales et al. |
| 5,314,406 A | 5/1994 | Arias et al. |
| 5,336,172 A | 8/1994 | Bales et al. |
| 5,336,220 A | 8/1994 | Ryan et al. |
| 5,350,356 A | 9/1994 | Bales et al. |
| 5,354,291 A | 10/1994 | Bales et al. |
| 5,429,596 A | 7/1995 | Arias et al. |
| 5,476,450 A | 12/1995 | Ruggio |
| 5,484,402 A | 1/1996 | Saravia et al. |
| 5,512,045 A | 4/1996 | Gurchumelidze |
| 5,549,547 A | 8/1996 | Cohen et al. |
| 5,776,096 A | 7/1998 | Fields |
| 5,827,229 A | 10/1998 | Auth et al. |
| 5,885,228 A | 3/1999 | Rosenman et al. |
| 5,885,288 A | 3/1999 | Aust et al. |
| 5,961,485 A | 10/1999 | Martin |
| 5,980,504 A | 11/1999 | Sharkey et al. |
| 6,213,970 B1 | 4/2001 | Nelson et al. |
| 6,328,730 B1 | 12/2001 | Harkrider |
| 6,358,200 B1 | 3/2002 | Grossi |
| 6,471,639 B2 | 10/2002 | Rudischhauser et al. |
| 6,623,445 B1 | 9/2003 | Nelson et al. |
| 6,645,140 B2 | 11/2003 | Brommersma et al. |
| 6,827,701 B2 | 12/2004 | MacMahon et al. |
| 6,830,556 B2 | 12/2004 | Harmon et al. |
| 6,857,617 B2 | 2/2005 | Forberg |
| 6,887,221 B1 | 5/2005 | Baillargeon et al. |
| 6,929,236 B1 | 8/2005 | Height et al. |
| 6,932,788 B2 | 8/2005 | Kamiyama et al. |
| 6,969,368 B2 | 11/2005 | Anspach et al. |
| 6,997,867 B2 | 2/2006 | Soble et al. |
| 7,004,931 B2 | 2/2006 | Hogendijk |
| 7,025,720 B2 | 4/2006 | Boebel et al. |
| 7,249,602 B1 | 7/2007 | Emanuel |
| 7,297,133 B2 | 11/2007 | Nelson et al. |
| 7,465,288 B2 | 12/2008 | Dudney et al. |
| 7,530,976 B2 | 5/2009 | MacMahon et al. |
| 7,540,868 B2 | 6/2009 | Elliott et al. |
| 7,802,574 B2 | 9/2010 | Schultz |
| 7,810,784 B2 | 10/2010 | Abe et al. |
| 7,846,126 B2 | 12/2010 | Steen et al. |
| 7,883,516 B2 | 2/2011 | Huang et al. |
| 7,935,049 B2 | 5/2011 | Michel et al. |
| 7,947,039 B2 | 5/2011 | Sartor |
| 8,002,732 B2 | 8/2011 | Vicsonti |
| 8,062,214 B2 | 11/2011 | Shener et al. |
| 8,192,500 B2 | 6/2012 | Chung |
| 8,241,278 B2 | 8/2012 | Sartor |
| 8,313,081 B2 | 11/2012 | Adelberg |
| 8,353,860 B2 | 1/2013 | Boulais et al. |
| 8,419,626 B2 | 4/2013 | Shener-Irmakoglu et al. |
| 8,460,182 B2 | 6/2013 | Ouyang et al. |
| 8,613,735 B2 | 12/2013 | Omeda et al. |
| 8,672,928 B2 | 3/2014 | Liu et al. |
| 8,702,681 B2 | 4/2014 | Douglas et al. |
| 8,721,595 B2 | 5/2014 | Stiehl et al. |
| D715,921 S | 10/2014 | Wan |
| 8,858,569 B2 | 10/2014 | Wan |
| 8,888,683 B2 | 11/2014 | Mejia |
| 8,894,601 B2 | 11/2014 | Moehle et al. |
| 8,945,093 B2 | 2/2015 | Ahluwalia |
| 9,011,412 B2 | 4/2015 | Albritton et al. |
| 9,089,631 B2 | 7/2015 | Schaeffer et al. |
| 9,095,646 B2 | 8/2015 | Chow et al. |
| 9,119,926 B2 | 9/2015 | Cuevas et al. |
| 9,138,347 B2 | 9/2015 | Wiljanen et al. |
| 9,155,453 B2 | 10/2015 | Kumar et al. |
| 9,155,454 B2 | 10/2015 | Sahney et al. |
| 9,167,958 B2 | 10/2015 | Banik et al. |
| 9,179,968 B2 | 11/2015 | Leo et al. |
| 9,192,284 B2 | 11/2015 | Hirsch et al. |
| 9,248,228 B2 | 2/2016 | Bono et al. |
| 9,339,631 B2 | 5/2016 | Graham et al. |
| 9,358,061 B2 | 6/2016 | Plascencia et al. |
| 9,360,124 B2 | 6/2016 | Schaeffer et al. |
| 9,387,121 B2 | 7/2016 | Wiljanen et al. |
| 9,427,504 B2 | 8/2016 | Newman |
| 9,545,334 B2 | 1/2017 | Steen et al. |
| 9,572,933 B2 | 2/2017 | Grannell et al. |
| 9,622,646 B2 | 4/2017 | Ouyang et al. |
| 9,668,643 B2 | 6/2017 | Kennedy et al. |
| 9,744,276 B2 | 8/2017 | Ahluwalia |
| 9,757,195 B2 | 9/2017 | Plascencia et al. |
| 9,775,674 B2 | 10/2017 | Schaeffer et al. |
| 9,820,762 B2 | 11/2017 | Cadeddu et al. |
| 9,833,130 B2 | 12/2017 | Schaeffer et al. |
| 9,839,739 B2 | 12/2017 | Qian |
| 9,878,145 B2 | 1/2018 | Holm et al. |
| 9,884,143 B2 | 2/2018 | Kobida et al. |
| 9,936,963 B2 | 4/2018 | Batchelor et al. |
| 9,968,249 B2 | 5/2018 | Huang et al. |
| 9,974,554 B2 | 5/2018 | Antonelli et al. |
| 9,980,631 B2 | 5/2018 | Schaeffer et al. |
| 9,982,791 B2 | 5/2018 | Schaeffer et al. |
| 10,004,385 B2 | 6/2018 | Bresco Torras et al. |
| 10,010,657 B2 | 7/2018 | Torrance et al. |
| 10,028,763 B2 | 7/2018 | Kumar et al. |
| 10,092,173 B2 | 10/2018 | Dejima |
| 10,165,933 B2 | 1/2019 | Dejima |
| 10,166,013 B2 | 1/2019 | Nguyen et al. |
| 10,213,533 B2 | 2/2019 | Walter |
| 10,220,123 B2 | 3/2019 | Monty et al. |
| 10,231,793 B2 | 3/2019 | Romo |
| 10,245,359 B2 | 4/2019 | Bono et al. |
| 10,251,539 B2 | 4/2019 | Sahney et al. |
| 10,251,671 B2 | 4/2019 | Dejima |
| 10,271,716 B2 | 4/2019 | Ferreira et al. |
| 10,286,141 B2 | 5/2019 | Monty et al. |
| 10,293,105 B2 | 5/2019 | Panotopoulos |
| 10,434,259 B2 | 10/2019 | Dejima et al. |
| 10,441,153 B2 | 10/2019 | Huang et al. |
| 10,441,460 B2 | 10/2019 | Ross et al. |
| 10,456,519 B2 | 10/2019 | Ngo-Chu et al. |
| 10,478,596 B2 | 11/2019 | Graham et al. |
| 10,500,323 B2 | 12/2019 | Huering et al. |
| 10,531,883 B1 | 1/2020 | Deville et al. |
| 10,596,306 B2 | 3/2020 | Ahluwalia |
| 10,610,622 B2 | 4/2020 | Jeong |
| 10,722,253 B2 | 7/2020 | Deville et al. |

(56) References Cited

U.S. PATENT DOCUMENTS

| | | |
|---|---|---|
| 10,722,620 B2 | 7/2020 | Chuang et al. |
| 10,765,449 B2 | 9/2020 | Dejima |
| 10,842,519 B2 | 11/2020 | Suh et al. |
| 10,850,013 B2 | 12/2020 | Hsu et al. |
| 10,912,873 B2 | 2/2021 | Nitzan et al. |
| 10,925,666 B2 | 2/2021 | Plascencia et al. |
| 11,026,715 B2 | 6/2021 | Mayberry |
| 11,035,481 B2 | 6/2021 | Schaeffer et al. |
| 11,064,871 B2 | 7/2021 | Gerbo et al. |
| 11,076,755 B2 | 8/2021 | Huang et al. |
| 11,096,568 B2 | 8/2021 | Harrah et al. |
| 11,123,483 B2 | 9/2021 | Panotopoulos |
| 2003/0199986 A1 | 10/2003 | Mcweeney et al. |
| 2003/0216760 A1 | 11/2003 | Welch et al. |
| 2004/0019358 A1 | 1/2004 | Kear |
| 2004/0153095 A1 | 8/2004 | Seddon |
| 2004/0153111 A1 | 8/2004 | Hosoada |
| 2004/0193103 A1 | 9/2004 | Kumar |
| 2004/0267213 A1 | 12/2004 | Knapp |
| 2005/0085692 A1 | 4/2005 | Kiehn et al. |
| 2005/0085769 A1 | 4/2005 | MacMahon et al. |
| 2005/0143678 A1 | 6/2005 | Schwarz et al. |
| 2005/0149201 A1 | 7/2005 | Mcweeney et al. |
| 2006/0069343 A1 | 3/2006 | Rontal |
| 2006/0206004 A1 | 9/2006 | Dehmel et al. |
| 2006/0264995 A1 | 11/2006 | Fanton et al. |
| 2007/0185383 A1 | 8/2007 | Mulhern et al. |
| 2007/0298069 A1 | 12/2007 | Bucay-couto et al. |
| 2008/0004578 A1 | 1/2008 | Nixon et al. |
| 2008/0058588 A1 | 3/2008 | Emanuel |
| 2008/0146991 A1 | 6/2008 | Hernandez et al. |
| 2008/0249483 A1 | 10/2008 | Slenker et al. |
| 2009/0163846 A1 | 6/2009 | Aklog et al. |
| 2009/0270894 A1 | 10/2009 | Rubin et al. |
| 2010/0010431 A1 | 1/2010 | Tulley |
| 2010/0056867 A1 | 3/2010 | Labombard et al. |
| 2010/0137846 A1 | 6/2010 | Desai et al. |
| 2010/0305475 A1 | 12/2010 | Hinchliffe et al. |
| 2011/0004197 A1 | 1/2011 | Sansoucy |
| 2011/0060315 A1 | 3/2011 | Windheuser et al. |
| 2011/0202039 A1 | 8/2011 | Schaaf |
| 2011/0224489 A1 | 9/2011 | Deal et al. |
| 2011/0245841 A1 | 10/2011 | Shohat et al. |
| 2012/0041358 A1 | 2/2012 | Mann et al. |
| 2013/0024003 A1 | 1/2013 | Mcweeney et al. |
| 2013/0123721 A1 | 5/2013 | Stiehl et al. |
| 2013/0131445 A1 | 5/2013 | Zerfas et al. |
| 2013/0138036 A1 | 5/2013 | Solomon et al. |
| 2013/0165944 A1 | 6/2013 | Gal et al. |
| 2013/0231605 A1 | 9/2013 | Walter |
| 2014/0107565 A1 | 4/2014 | Wiljanen et al. |
| 2014/0171922 A1 | 6/2014 | Douglas et al. |
| 2014/0276377 A1 | 9/2014 | Chang et al. |
| 2014/0288460 A1 | 9/2014 | Ouyang et al. |
| 2014/0296894 A1 | 10/2014 | Kojima et al. |
| 2015/0150441 A1 | 6/2015 | Ouyang et al. |
| 2015/0305759 A1 | 10/2015 | St. George et al. |
| 2015/0328394 A1 | 11/2015 | Chow et al. |
| 2016/0001050 A1 | 1/2016 | Yee et al. |
| 2016/0022289 A1 | 1/2016 | Wan |
| 2016/0030070 A1 | 2/2016 | Eisner |
| 2016/0120557 A1 | 5/2016 | Goddard et al. |
| 2016/0270804 A1* | 9/2016 | Honda .................. A61B 17/22 |
| 2016/0374755 A1 | 12/2016 | Mirigian et al. |
| 2017/0027604 A1 | 2/2017 | Wallace |
| 2017/0065752 A1 | 3/2017 | Eisner |
| 2017/0215899 A1 | 8/2017 | Harrah et al. |
| 2017/0215964 A1 | 8/2017 | Harrah et al. |
| 2017/0215965 A1 | 8/2017 | Harrah et al. |
| 2017/0252051 A1 | 9/2017 | Wan et al. |
| 2017/0266046 A1 | 9/2017 | Steen et al. |
| 2017/0303941 A1 | 10/2017 | Eisner |
| 2017/0319776 A1 | 11/2017 | Eisner |
| 2017/0333614 A1 | 11/2017 | Gao et al. |
| 2017/0340862 A1 | 11/2017 | Calabrese et al. |
| 2017/0354431 A1 | 12/2017 | Rubin et al. |
| 2018/0206866 A1 | 7/2018 | Wan |
| 2018/0360480 A1 | 12/2018 | Ciulla |
| 2019/0038817 A1 | 2/2019 | Forsberg et al. |
| 2019/0059988 A1 | 2/2019 | Davison et al. |
| 2019/0099209 A1 | 4/2019 | Witt et al. |
| 2019/0192222 A1 | 6/2019 | Mirigian et al. |
| 2019/0274699 A1 | 9/2019 | Morey et al. |
| 2019/0290811 A1 | 9/2019 | Bono et al. |
| 2019/0314044 A1 | 10/2019 | Long et al. |
| 2019/0328412 A1 | 10/2019 | Mazhar et al. |
| 2019/0357762 A1 | 11/2019 | Clayman et al. |
| 2020/0009302 A1 | 1/2020 | Pyle |
| 2020/0046393 A1 | 2/2020 | Kendale et al. |
| 2020/0147294 A1 | 5/2020 | Edwards |
| 2020/0188014 A1 | 6/2020 | Woloszko et al. |
| 2020/0196843 A1 | 6/2020 | Tah et al. |
| 2020/0229907 A1 | 7/2020 | Duehlmeier |
| 2020/0297362 A1 | 9/2020 | Deville et al. |
| 2021/0085158 A1 | 3/2021 | Ikuma et al. |

FOREIGN PATENT DOCUMENTS

| | | |
|---|---|---|
| CN | 203988361 U | 12/2014 |
| WO | WO 2010/068467 A1 | 6/2010 |
| WO | WO 2014/160201 A1 | 10/2014 |
| WO | WO 2017/135980 A1 | 8/2017 |
| WO | WO 2019/178387 A1 | 9/2019 |
| WO | WO 2020/146454 A1 | 7/2020 |
| WO | WO 2020/150713 A2 | 7/2020 |
| WO | WO 2020/247103 A1 | 12/2020 |

OTHER PUBLICATIONS

Chew, et al., "Natural History, Complications and Re-Intervention Rates of Asymptomatic Residual Stone Fragments after Ureteroscopy: a Report from the EDGE Research Consortium", The Journal of Urology; Apr. 2016 (published online Nov. 2015); vol. 195, pp. 982-986.

Deng, et al., "Suctioning flexible ureteroscopy with automatic controlof renal pelvic pressure: a porcine model", International Journal of Clinical and Experimental Medicine, Mar. 30, 2016.

Deng, et al., "A Novel Flexible Ureteroscopy with Intelligent Control of Renal Pelvic Pressure: An Initial Experience of 93 Cases", Journal of Endourology; Oct. 2016 (published online Aug. 2016); vol. 30(10), pp. 1067-1072.

Emmott, et al., "Complications, Re-Intervention Rates, and Natural History of Residual Stone Fragments After Percutaneous Nephrolithotomy", Journal of Endourology; Jan. 2018; vol. 32(1), pp. 28-32.

Huang, et al., "Endourology and Stones | The Application of Suctioning Flexible Ureteroscopy With Intelligent Pressure Control in Treating Upper Urinary Tract Calculi on Patients With a Solitary Kidney", Urology Jan. 2018; vol. 111, pp. 44-47.

Kim, et al., "The Clinical Efficacy of Dual-Lumen Catheter Technique in Retrograde Intrarenal Surgery for the Management of Nephrolithiasis: A Propensity Score Analysis", Journal of Endourology; Dec. 2018; vol. 32(12).

Leveillee, et al.,"Impressive Performance: New Disposable Digital Ureteroscope Allows for Extreme Lower Pole Access and Use of 365 μm Holmium Laser Fiber", Journal of Endourology Case Reports; Jun. 1, 2016; vol. 2(1), pp. 114-116.

Li, et al., "A Novel Semirigid Ureterorenoscope with Vacuum Suctioning System for Management of Single Proximal Ureteral and Renal Pelvic Stones: An Initial Experience", Journal of Endourology; Dec. 2018; vol. 32(12), pp. 1154-1159.

Peng, et al., "Suctioning flexible ureteroscopic lithotripsy in the oblique supine lithotomy position and supine lithotomy position: a comparative retrospective study", Minerva Urologica e Nefrologica, Dec. 2018; vol. 70(6), pp. 612-616.

Portis, et al., "Endourology and Stones | Repeat Surgery After Ureteroscopic Laser Lithotripsy With Attempted Complete Extraction of Fragments: Long-term Follow-up", Urology Jun. 2015; vol. 85(6), pp. 1272-1278.

(56) References Cited

OTHER PUBLICATIONS

Raman, et al., "Natural History of Residual Fragments Following Percutaneous Nephrostolithotomy", Journal of Urology Mar. 2009; vol. 181(3), pp. 1163-1168.

Rebuck, et al., "Endourology and Stones | The Natural History of Renal Stone Fragments Following Ureteroscopy", Urology Mar. 2011; vol. 77(3), pp. 564-568.

Scales, et al., "The impact of unplanned postprocedure visits in the management of patients with urinary stones", Surgery May 2014; vol. 155(5), pp. 769-775.

Skolarikos, et al., "Urolithiasis/Endourology | Outcomes of Flexible Ureterorenoscopy for Solitary Renal Stones in the CROES URS Global Study", Journal of Urology Jul. 2015; vol. 194(1), pp. 137-143.

Villanueva, et al., "Silicone Catheters May Be Superior to Latex Catheters in Difficult Urethral Catheterization After Urethral Dilation", Journal of Endourology 2011, vol. 25(5), pp. 841-844.

Zeng, et al., "Modified Access Sheath for Continuous Flow Ureteroscopic Lithotripsy: A Preliminary Report of a Novel Concept and Technique", Journal of Endourology Sep. 2016; vol. 30(9), pp. 992-996.

\* cited by examiner

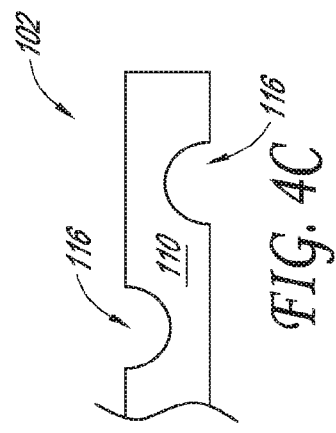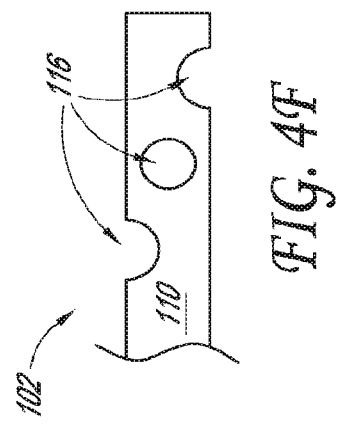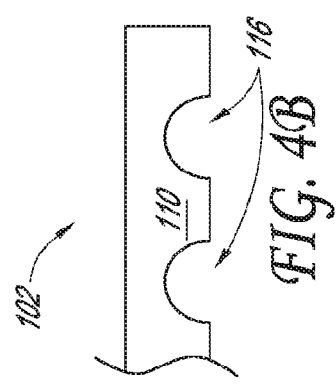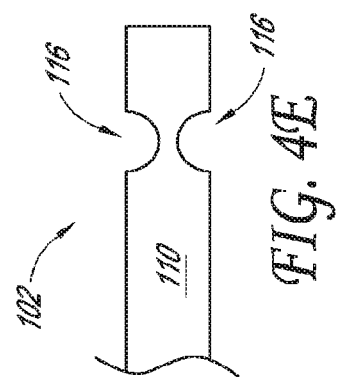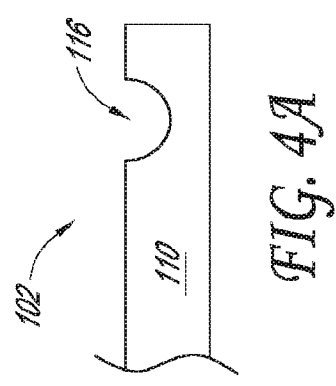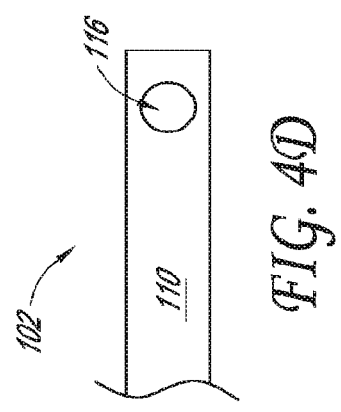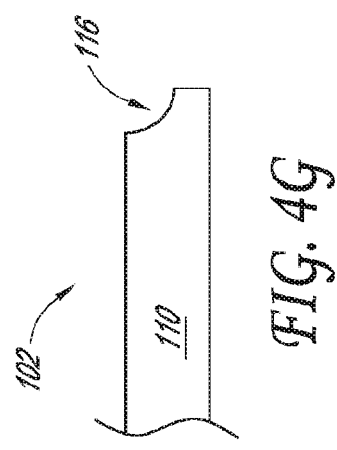

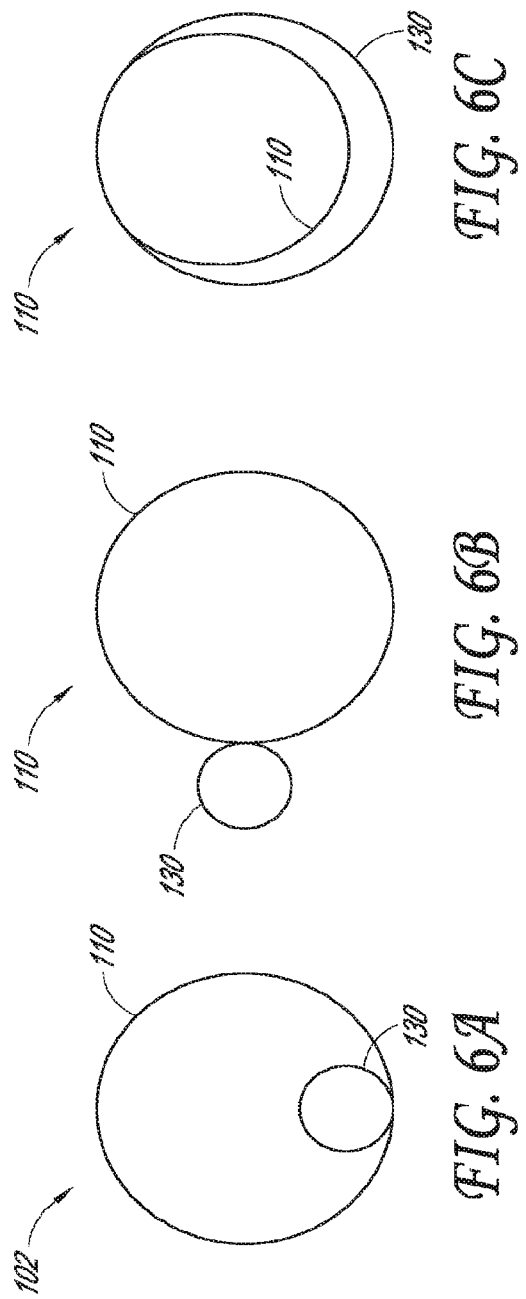

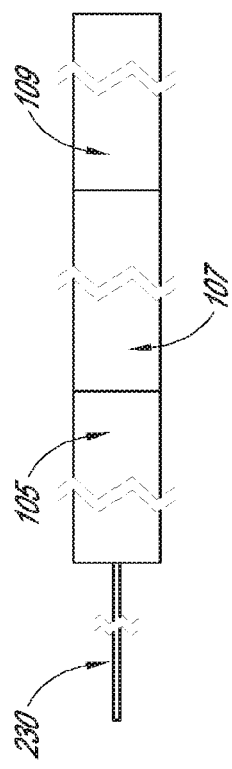
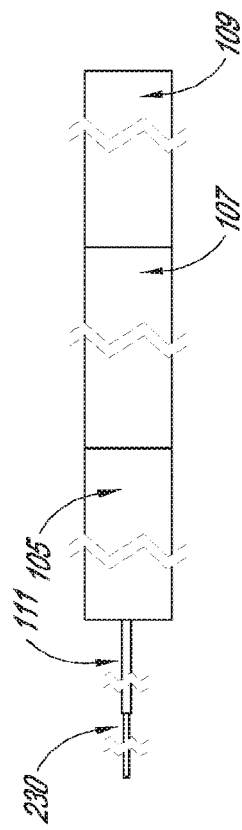

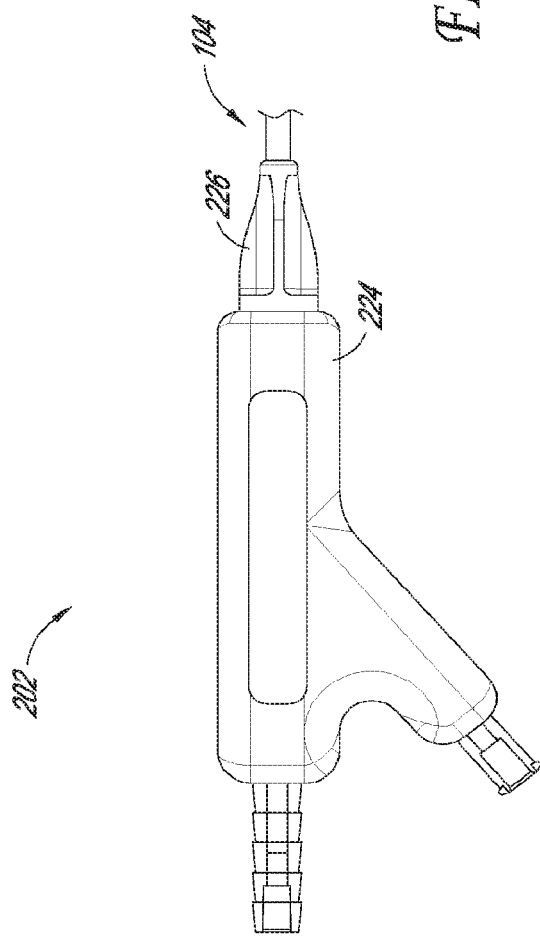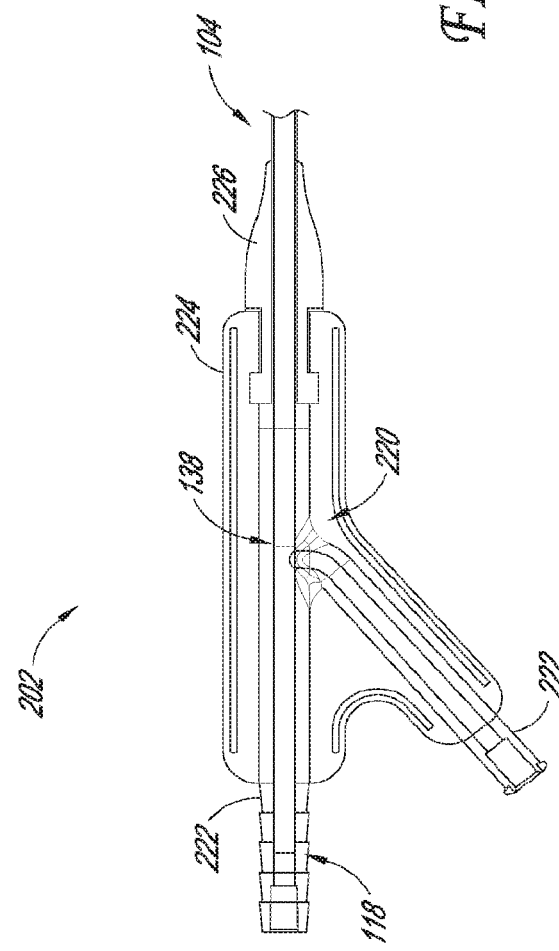

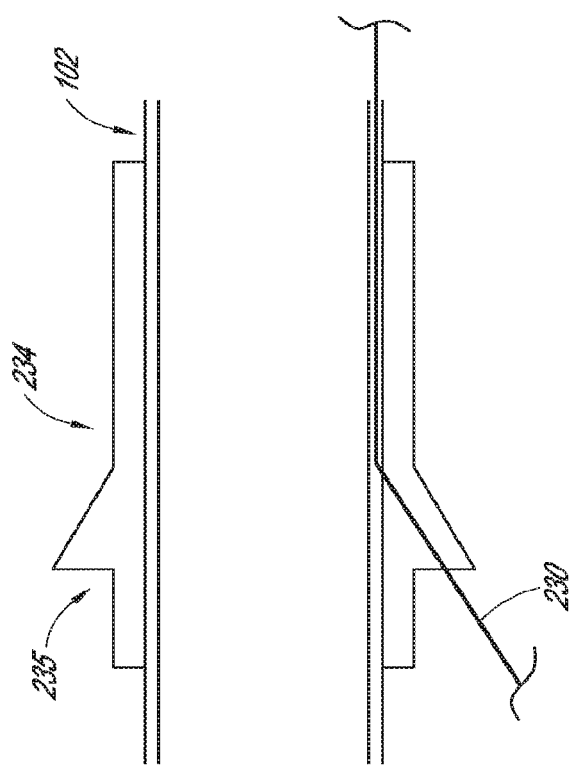

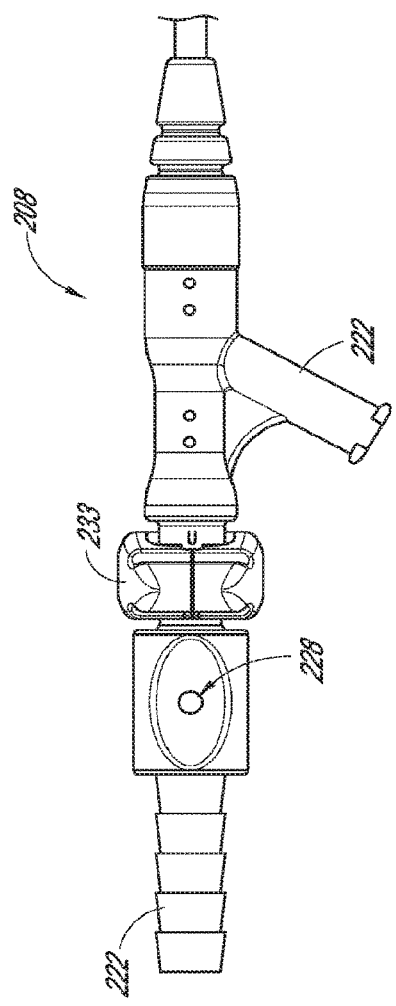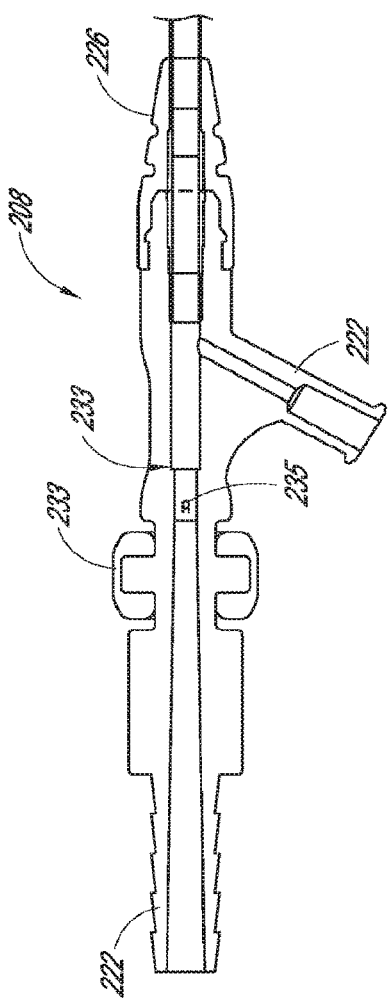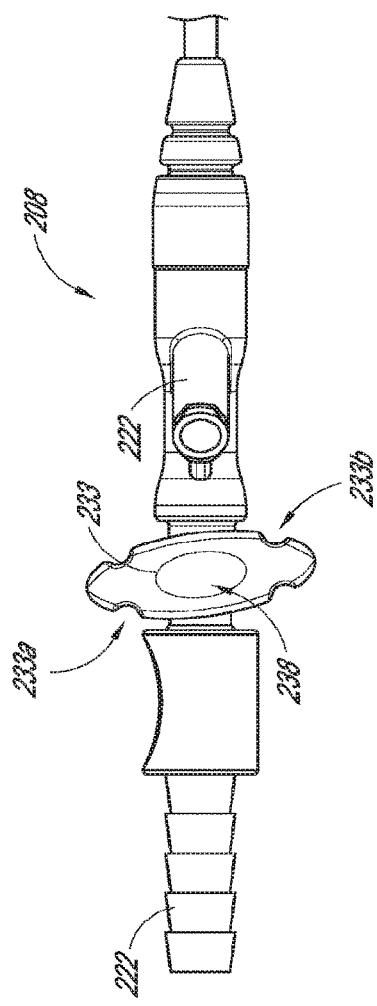

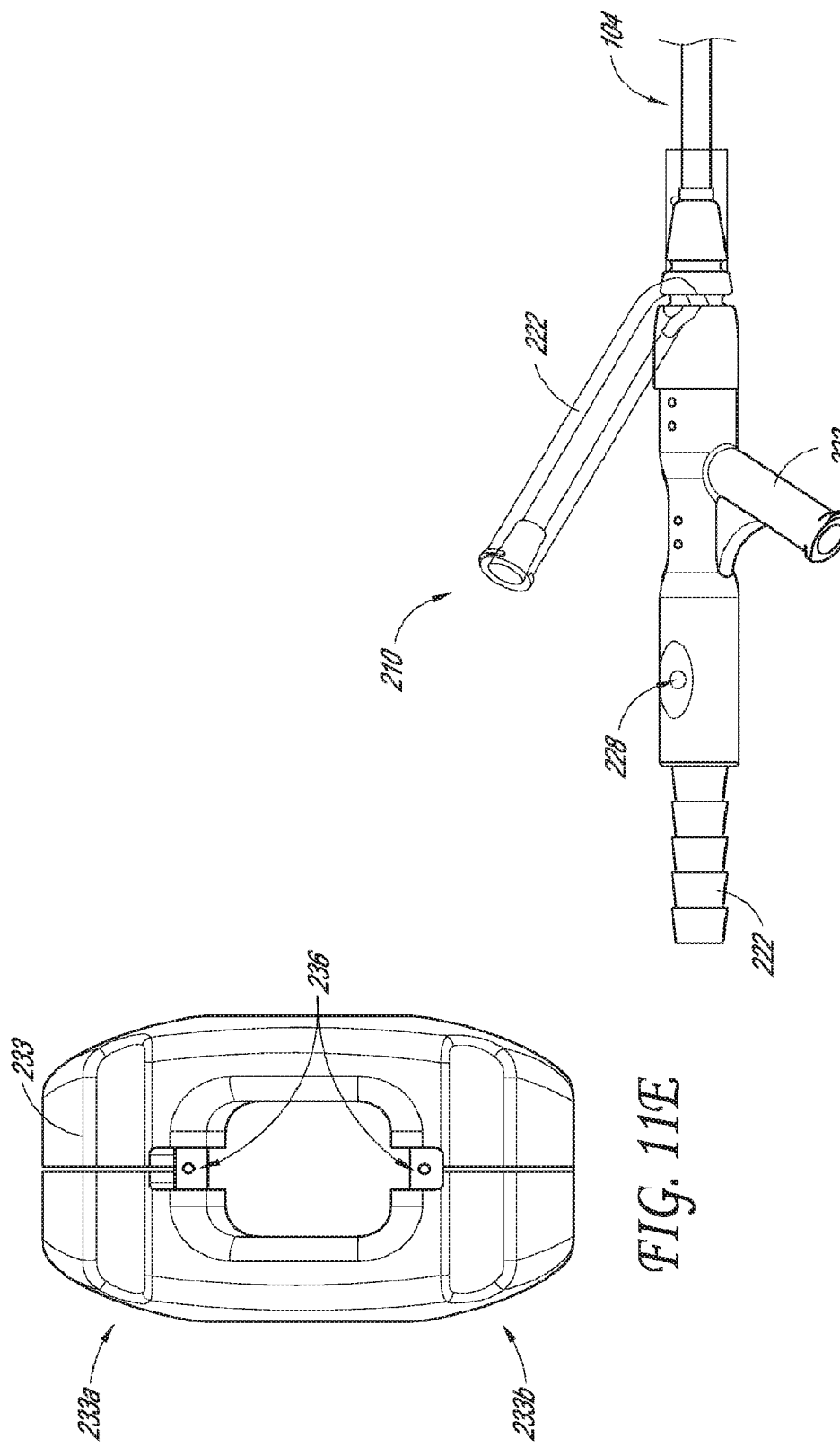

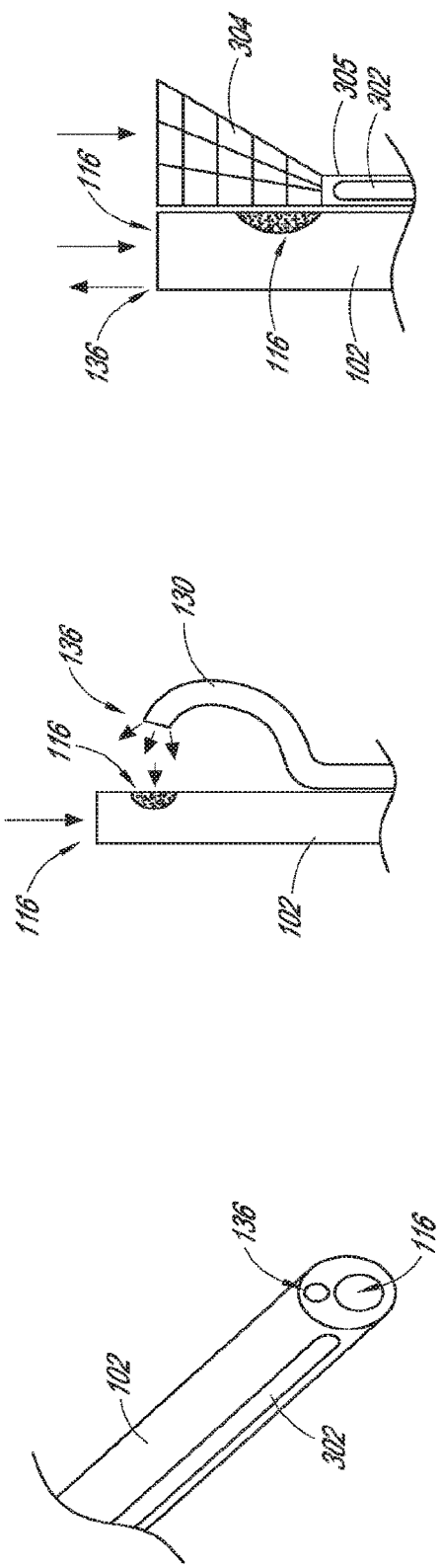
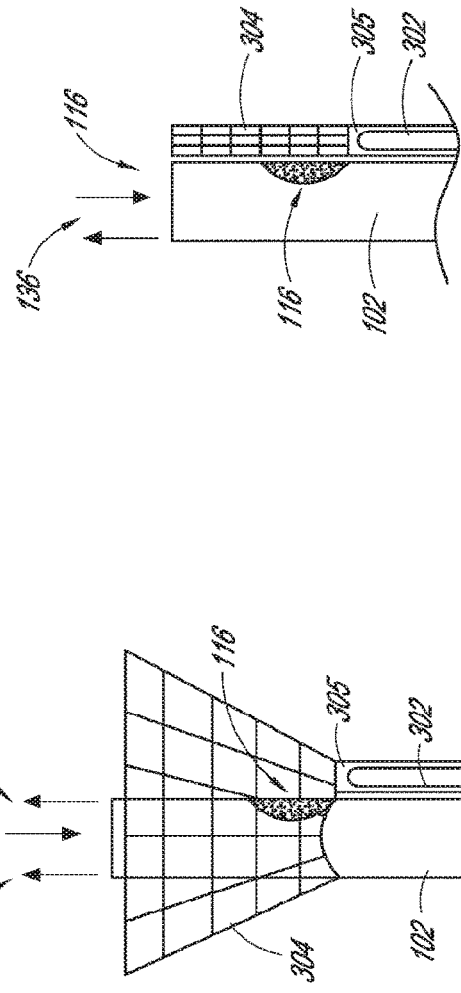

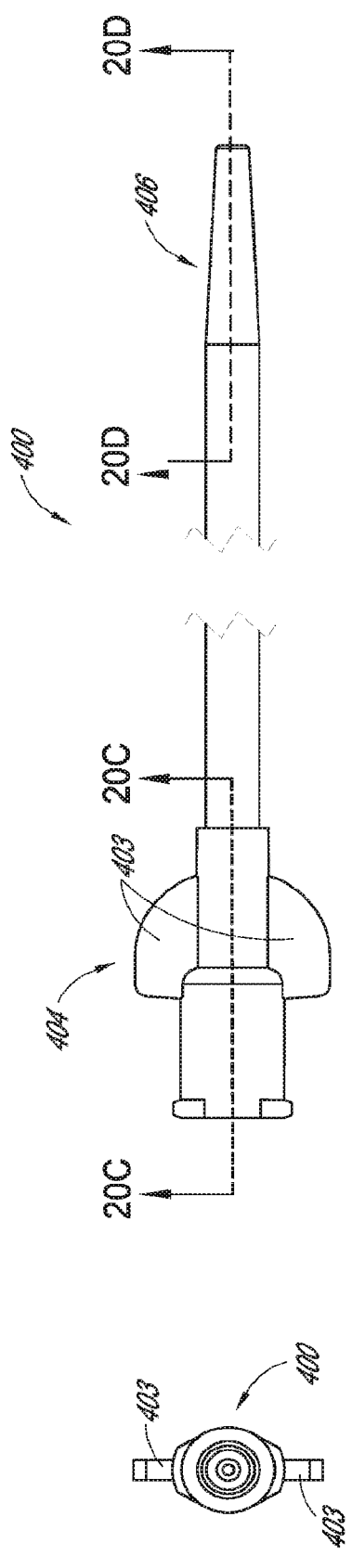

DEVICES AND METHODS FOR MINIMALLY INVASIVE KIDNEY STONE REMOVAL BY COMBINED ASPIRATION AND IRRIGATION

CROSS-REFERENCE

The present application is a continuation of U.S. patent application Ser. No. 16/966,856 filed on Jul. 31, 2020, as the 35 USC 371 National Stage filing of PCT/US2019/016172 filed on Jan. 31, 2019, which claims the benefit of and priority to U.S. Provisional Patent Application No. 62/649,430 filed on Mar. 28, 2018, and further to U.S. Provisional Patent Application No. 62/625,766 filed on Feb. 2, 2018, all of these applications are incorporated herein by reference in their entirety.

BACKGROUND

The present invention relates to systems and methods for the guided removal of objects in vivo. In particular, the invention is directed to a removal device adapted to traverse compact areas utilizing a navigation mechanism, and more specifically, to capture and/or remove debris through a vacuum tube that is in communication with a suction source.

Kidney stones are a common medical problem that negatively impact millions of individuals worldwide. Kidney stones include one or more solid masses of material that are usually made of crystals and form in parts of the urinary tract including in the ureter, the kidney, and/or the bladder of the individual. Kidney stones range in size from smaller (less than about 1 cm) to very large (more than 4 cm) and may cause significant pain to the individual and damage to the kidney. The overwhelming majority of stones that are treated by surgeons are less than 1 cm.

The recommended treatment for removal of the kidney stones varies according to numerous factors including the size of the kidney stones, the number of kidney stones, and the location of the kidney stones. The most common treatments for kidney stones are shock wave lithotripsy (ultrasound waves used to fracture the stones), ureteroscopy (fracture and removal of the stones using an endoscope that is introduced through the bladder), and percutaneous nephrolithotomy (fracture and removal of the stones using an endoscope that is introduced through a sheath placed through the patient's back into the kidney).

The largest kidney stones are usually removed through percutaneous nephrolithotomy or nephrolithotripsy, or through other similar procedures. In these procedures, a small incision is made through the patient's back adjacent the kidney and a sheath is passed into the kidney to accommodate a larger endoscope used to fracture and remove stones. The stone may be removed directly through the tube or may be broken up into small fragments while still in the patient's body and then removed via a vacuum or other known methods (nephrolithotripsy).

There are numerous drawbacks associated with nephrolithotomy, nephrolithotripsy, and other invasive surgeries requiring an incision in the skin. Namely, such surgical techniques may require significantly more anesthesia administered to the patient, the surgeries are more complicated and pose a higher risk of infection and complications for the patient, and the surgeries require a substantial incision in the patient, which may leave a scar. Additionally, given the invasiveness of the procedure, percutaneous procedures are usually not preferred for smaller kidney stones (e.g., less than 1 cm) depending on the size and location of the stones.

In contrast, traditionally, smaller kidney stones have been treated using other, less invasive techniques including through ureteroscopy. In ureteroscopy, the surgeon typically inserts a ureteroscope into the urethra through the bladder and the ureter to provide the surgeon with a direct visualization of the kidney stone(s) which may reside in the ureter or kidney. The surgeon then removes the kidney stone directly using a basketing device if the kidney stone is small enough to pass through the urinary tract without difficulty, or the surgeon fractures the kidney stone into smaller pieces using a laser or other breaking device. After breaking the kidney stone into smaller pieces, the surgeon removes the laser or breaking device and inserts a basket or other object to capture the kidney stone fragments under the direct visualization of the ureteroscope. Upon retrieving some of the kidney stone fragments, the surgeon removes the basket from the patient and empties the kidney stone fragments therefrom. This process is repeated until clinically significant kidney stones and kidney stone fragments are broken up and removed from the body.

It should be apparent that this process is extremely time consuming, costly, and inefficient because the surgeon is required to insert and remove the scope and basket into and out of the patient many times to completely remove the kidney stones and kidney stone fragments therefrom. Using a basket removal device to capture kidney stones or kidney stone fragments suffers from other drawbacks in that the basket is difficult to position adjacent the kidney stone fragments and maneuver in a manner that effectively retrieves the fragments. The training required for such a procedure is not insignificant and the aforementioned basket removal technique is difficult for even the most skilled surgeons. Additionally, the surgeon is susceptible to hand fatigue due to the extended amount of time required to operate the kidney stone retrieval baskets. Further, the patient is required to be under local anesthesia and/or remain immobile over an extended amount of time. Still further, the basket retrieval devices cause irritation to the urinary tract due to the repeated insertion and removal therefrom. Thus, there is an unmet need for new devices and methods that permit minimally invasive removal of kidney stones.

SUMMARY

Disclosed herein is a method of removing a kidney stone from a kidney of a patient. The method comprises inserting a catheter into the urethra of the patient and advancing the catheter to a location within the kidney proximate to the kidney stone. The catheter has a distal portion steerable in one or more directions. The distal portion includes an aspiration port for providing suction and an irrigation port for providing irrigation fluid. The method further comprises steering the distal steerable portion so that the steerable portion is bent into a configuration in which the kidney stone is aligned with the aspiration port, providing irrigation through the irrigation port, and providing suction through the catheter to aspirate the kidney stone from the kidney without removing the catheter from the kidney.

In some implementations, suction and irrigation may not be provided during the steering of the distal steerable portion. The catheter may be rotated during the steering. Suction and irrigation may be halted after the kidney stone is aspirated. After the kidney stone is aspirated, the distal steerable portion can be bent into a configuration in which a second kidney stone is aligned with the aspiration port. Irrigation may be provided continuously and suction provided intermittently during a period. Suction may be provided continuously and irrigation provided intermittently during a period. Suction and irrigation may both be provided continuously during a period. Suction and irrigation may both be provided intermittently during a period. When provided intermittently, suction and irrigation may be provided simultaneously. When provided intermittently, suction may be applied continuously during any interval in which irrigation is not applied, and irrigation may be applied continuously during any interval in which suction is not provided.

The catheter may have a handle configured to be positioned outside the body of the patient. The handle may have a control for a user to stop and/or start the suctioning. The handle may have a control for a user to stop and/or start the irrigation. The handle may have a control for a user to stop and/or start the suction and the irrigation. The control can be a hole configured to be covered by a single finger of the user. Covering the hole may cause suction to be provided.

The method may comprise adjusting the curvature of the distal steerable portion. Adjusting the curvature of the distal steerable portion may comprise pulling and/or pushing a lever on a handle of the catheter positioned outside of the body. The lever may be coupled to the distal steerable portion by one or more pull wires. The method may comprise positioning the distal steerable portion in a calyx of the kidney after adjusting the curvature of the distal steerable portion. The method may comprise rotating the catheter after applying a curvature to the distal steerable portion of the catheter during suctioning. The method may comprise adjusting the curvature of the steerable distal portion to sweep laterally in a side-to-side motion during suctioning. The method may comprise retracting the catheter in a proximal direction within the kidney during suctioning. The method may comprise advancing the catheter in a distal direction within the kidney during suctioning. The method may comprise reciprocating the catheter in a distal and proximal direction within the kidney during suctioning.

The catheter may have a lateral aspiration port positioned on a first side of the catheter and an irrigation port positioned on a distal face of the catheter. The method may comprise bending the distal end of the catheter in the direction of the lateral aspiration port such that irrigation fluid is directed toward the lateral aspiration port during suction. Providing irrigation may comprise directing an irrigation fluid from a distal end of the catheter in a direction substantially parallel to a distal facing direction of the catheter. Providing irrigation may comprise directing an irrigation fluid from a distal end of the catheter in a direction substantially away from an axis of a distal-facing aspiration port. Providing irrigation may comprise directing an irrigation fluid from a distal end of the catheter in a direction substantially toward an axis of a distal-facing aspiration port. Providing irrigation may comprise directing irrigation fluid in a radially outward direction from a distal end of the catheter. Providing irrigation may comprise directing irrigation fluid in a radially inward direction from a distal end of the catheter. Providing irrigation may comprise directing irrigation fluid from an irrigation port on a distal face of the catheter and from a lateral irrigation port on a side of the catheter.

Providing suction may comprise aspirating through a lateral-facing aspiration port on a side of the catheter and providing irrigation may comprise directing irrigation fluid from a lateral-facing irrigation port. The lateral-facing aspiration port may be positioned distally of the lateral-facing irrigation port or proximally of the lateral-facing irrigation port. The lateral-facing irrigation port may direct irrigation fluid in an axial direction toward the lateral-facing aspiration port. Providing irrigation may comprise steering a distal face of the catheter to curve in a direction toward an aspiration port. The distal face may have an irrigation port.

The method may comprise inserting an ancillary device laterally adjacent the catheter. The ancillary device may be a guidewire. The method may further comprise axially translating the ancillary device with respect to the catheter. The ancillary device may have a steerable distal portion and the method may further comprise steering the distal portion. The ancillary device may be an irrigation tube and the method may further comprise providing irrigation from the ancillary device. The method may comprise positioning the irrigation tube to direct irrigation fluid toward a lateral-facing aspiration port on a side of the catheter. The method may comprise guiding kidney stones toward an aspiration port on the catheter using a shield on the ancillary device. The shield may have a collapsed configuration and an expanded configuration and the method may comprise expanding the shield after insertion of the ancillary device into the bladder or kidney.

Steering the distal steerable portion may comprise bending the distal steerable portion in more than one direction. Providing irrigation may comprise providing an irrigation stream selected from the group consisting of: a flat stream, a fanned stream, and a conical stream. The catheter may have a plurality of irrigation ports, and providing irrigation may comprise producing a single jet stream of irrigation from the plurality of irrigation ports or producing a shower effect of irrigation streams. Providing irrigation may comprise producing an irrigation stream having a vortex effect.

The location within the kidney may be a first pole of the kidney. The method may comprise steering the distal steerable portion to sweep the first pole of the kidney, then repositioning the catheter in a second pole of the kidney and steering the distal steerable portion to sweep the second pole of the kidney, and then repositioning the catheter in a third pole of the kidney and steering the distal steerable portion to sweep the third pole of the kidney. The first pole may be the upper pole of the kidney, the second pole may be the middle pole of the kidney, and the third pole may be the lower pole of the kidney. The sweep may comprise incremental movements and suctioning and/or irrigation may be performed only while the catheter is stationary between incremental movements, during incremental movements, or a combination of both. Providing irrigation may comprise flushing the upper pole and the middle pole of the kidney with irrigation fluid. Flushing may fill, or at least partially fill the calyx, which may advantageously prevent suctioning of kidney tissue as described elsewhere herein. Flushing may be used to attempt to move any kidney stones to another pole, such as from the upper and middle poles into the lower pole, in some embodiments. Providing suction may comprise aspirating kidney stones from the lower pole of the kidney.

The method may comprise providing a non-suctioning period of time during which no suction is provided through the aspiration port. During the non-suctioning period, the aspiration port may be in fluid communication with the ambient atmosphere outside of the patient, thereby equilibrating the pressure between the inside of the kidney and the ambient atmosphere.

Providing irrigation may comprise providing a pulsatile flow of irrigation fluid. The pulsatile flow may be provided at a frequency of at least about 1 Hz. The pulsatile flow may comprise stopping and starting irrigation. The pulsatile flow may comprise increasing and decreasing the irrigation pressure while maintaining a delivery of irrigation fluid. Providing suction may comprise providing pulsatile suctioning.

Pulsatile suctioning may be provided at a frequency of at least about 1 Hz. The pulsatile suctioning may comprise stopping and starting suctioning. The pulsatile suctioning may comprise increasing and decreasing the suction pressure while maintaining at least some suctioning. Providing irrigation and providing suction may comprise providing synchronized pulsatile irrigation and pulsatile suctioning. Irrigation pressure may be increased as suction pressure is decreased and irrigation pressure may be decreased as suction pressure is increased. Irrigation pressure may be increased as suction pressure is increased and irrigation pressure may be decreased as suction pressure is decreased. Providing irrigation and providing suction may comprise suspending the kidney stone in the irrigation fluid. Providing irrigation and providing suction may comprise fluidizing the kidney stone with the irrigation fluid.

In a further aspect of the invention, disclosed herein is a method of removing a kidney stone from a kidney of a patient. The method comprises inserting a catheter into the urethra of the patient and advancing the catheter to a location within the kidney proximate to the kidney stone. The catheter has a distal portion steerable in one or more directions. The distal portion has an aspiration port for providing suction and an irrigation port for providing irrigation fluid. The method further comprises guiding the kidney stone from a first location in the kidney to a second location in the kidney and positioning the aspiration port proximate to the kidney stone. The method further comprises providing irrigation through the irrigation port and providing suction through the catheter to aspirate the kidney stone from the kidney without removal of the catheter from the kidney.

In some implementations, suction and irrigation may not be provided from the catheter during the guiding of the kidney stone. Guiding the kidney stone from the first location to the second location may comprise moving the kidney stone using an ancillary device. The kidney stone may be guided using a shield or basket device. The kidney stone may be guided using irrigation provided by an ancillary irrigation tube. The kidney stone may be guided using the distal portion of the catheter. The kidney stone may be guided using irrigation provided by the irrigation port. Suction and irrigation may be halted after the kidney stone is aspirated. After the kidney stone is aspirated, a second kidney stone may be guided from a third location in the kidney to the first location in the kidney or a fourth location in the kidney.

Irrigation may be provided continuously and suction provided intermittently during a period. Suction may be provided continuously and irrigation provided intermittently during a period. Suction and irrigation may be provided continuously during a period. Suction and irrigation may both be provided intermittently during a period. When provided intermittently, suction and irrigation may be provided simultaneously. When provided intermittently, suction may be applied continuously during any interval in which irrigation is not applied, and irrigation may be applied continuously during any interval in which suction is not provided.

The catheter may have a handle configured to be positioned outside the body of the patient. The handle may have a control for a user to stop and/or start the suctioning. The handle may have a control for a user to stop and/or start the irrigation. The handle may have a control for a user to stop and/or start the suction and the irrigation. The control may be a hole configured to be covered by a single finger of the user. Covering the hole may cause the suction to be provided.

The catheter may have a distal steerable portion and the method may comprise adjusting the curvature of the distal steerable portion in one or more directions. Adjusting the curvature of the distal steerable portion may comprise pulling, turning, and/or pushing a lever on a handle of the catheter positioned outside of the body. The lever may be coupled to the distal steerable portion by one or more pull wires. The method may comprise positioning the distal steerable portion in a calyx of the kidney after adjusting the curvature of the distal steerable portion. The method may comprise rotating the catheter after applying a curvature to the distal steerable portion of the catheter during suctioning. The method may comprise adjusting the curvature of the distal steerable portion to sweep laterally in a side-to-side motion during suctioning. The method may comprise retracting the catheter in a proximal direction within the kidney during suctioning. The method may comprise advancing the catheter in a distal direction within the kidney during suctioning. The method may comprise reciprocating the catheter in a distal and proximal direction within the kidney during suctioning.

The catheter may have a lateral aspiration port positioned on a first side of the catheter and an irrigation port positioned on a distal face of the catheter. The method may comprise bending the distal end of the catheter in the direction of the lateral aspiration port such that irrigation fluid is directed toward the lateral aspiration port during suction. Providing irrigation may comprise directing an irrigation fluid from a distal end of the catheter in a direction substantially parallel to a distal facing direction of the catheter. Providing irrigation may comprise directing an irrigation fluid from a distal end of the catheter in a direction substantially away from an axis of a distal-facing aspiration port. Providing irrigation may comprise directing an irrigation fluid from a distal end of the catheter in a direction substantially toward an axis of a distal-facing aspiration port. Providing irrigation may comprise directing irrigation fluid in a radially outward direction from a distal end of the catheter. Providing irrigation may comprise directing irrigation fluid in a radially inward direction from a distal end of the catheter. Providing irrigation may comprise directing irrigation fluid from an irrigation port on a distal face of the catheter and from a lateral irrigation port on a side of the catheter.

Providing suction may comprise aspirating through a lateral-facing aspiration port on a side of the catheter and providing irrigation may comprise directing irrigation fluid from a lateral-facing irrigation port. The lateral-facing aspiration port may be positioned distally of the lateral-facing irrigation port or proximally of the lateral-facing irrigation port. The lateral-facing irrigation port may direct irrigation fluid in an axial direction toward the lateral-facing aspiration port. Providing irrigation may comprise steering a distal face of the catheter to curve in a direction toward an aspiration port. The distal face may have an irrigation port.

The method may comprise inserting an ancillary device laterally adjacent the catheter. The ancillary device may be a guidewire. The method may comprise axially translating the ancillary device with respect to the catheter. The ancillary device may have a steerable distal portion, and the method may comprise steering the distal portion. The ancillary device may be an irrigation tube, and the method may comprise providing irrigation from the ancillary device. The method may comprise positioning the irrigation tube to direct irrigation fluid toward a lateral-facing aspiration port on a side of the catheter. The method may comprise guiding kidney stones toward an aspiration port on the catheter using a shield on the ancillary device. The shield may have a collapsed configuration and an expanded configuration, and the method may comprise expanding the shield after insertion of the ancillary device into the bladder or kidney.

Steering the distal steerable portion may comprise bending the distal steerable portion in more than one direction. Providing irrigation may comprise providing an irrigation stream selected from the group consisting of: a flat stream, a fanned stream, and a conical stream. The catheter may have a plurality of irrigation ports, and providing irrigation may comprise producing a single jet stream of irrigation from the plurality of irrigation ports or producing a shower effect of irrigation streams. Providing irrigation may comprise producing an irrigation stream having a vortex effect.

The first location within the kidney may be a first pole of the kidney. The method may comprise steering the distal steerable portion to sweep the first pole of the kidney, then repositioning the catheter in a second pole of the kidney and steering the distal steerable portion to sweep the second pole of the kidney, and then repositioning the catheter in a third pole of the kidney and steering the distal steerable portion to sweep the third pole of the kidney. The first pole may be the upper pole of the kidney, the second pole may be the middle pole of the kidney, and the third pole may be the lower pole of the kidney. The sweep may comprise incremental movements and suctioning and irrigation may be performed only while the catheter is stationary between incremental movements. Providing irrigation may comprise flushing the upper pole and the middle pole of the kidney with irrigation fluid to move kidney stones from the upper and middle poles into the lower pole, and providing suction may comprise aspirating kidney stones from the lower pole of the kidney.

The method may comprise providing a non-suctioning period of time during which no suction is provided through the aspiration port. During the non-suctioning period, the aspiration port may be in fluid communication with the ambient atmosphere outside of the patient, thereby equilibrating the pressure between the inside of the kidney and the ambient atmosphere.

Providing irrigation may comprise providing a pulsatile flow of irrigation fluid. The pulsatile flow may be provided at a frequency of at least about 1 Hz. The pulsatile flow may comprise stopping and starting irrigation. The pulsatile flow may comprise increasing and decreasing the irrigation pressure while maintaining a delivery of irrigation fluid. Providing suction may comprise providing pulsatile suctioning. Pulsatile suctioning may be provided at a frequency of at least about 1 Hz. The pulsatile suctioning may comprise stopping and starting suctioning. The pulsatile suctioning may comprise increasing and decreasing the suction pressure while maintaining at least some suctioning. Providing irrigation and providing suction may comprise providing synchronized pulsatile irrigation and pulsatile suctioning. Irrigation pressure may be increased as suction pressure is decreased and irrigation pressure may be decreased as suction pressure is increased. Irrigation pressure may be increased as suction pressure is increased and irrigation pressure may be decreased as suction pressure is decreased. Providing irrigation and providing suction may comprise suspending the kidney stone in the irrigation fluid. Providing irrigation and providing suction may comprise fluidizing the kidney stone with the irrigation fluid.

In a further aspect of the invention, disclosed herein is a removal device for removal of kidney stones from a patient. The removal device includes a catheter having a distal steerable portion steerable in one or more directions. The distal portion includes an aspiration port and an irrigation port. The catheter further includes a vacuum lumen in fluid communication with the aspiration port for providing suction to the aspiration port and an irrigation lumen in fluid communication with the irrigation port for providing irrigation to the irrigation port.

The aspiration port and the irrigation port may be distal facing. The distal-facing irrigation port may be configured to direct the irrigation fluid in a direction substantially parallel to the distal facing direction. The distal-facing irrigation port may be configured to direct the irrigation fluid in a direction away from the distal-facing aspiration port. The distal-facing irrigation port may be configured to direct the irrigation fluid in a direction substantially toward the distal-facing aspiration port. The distal-facing irrigation port may be configured to direct irrigation fluid in a radially outward direction. The distal-facing irrigation port may be configured to direct irrigation fluid in a radially inward direction.

The irrigation port may be distal facing and the aspiration port may be lateral facing. The distal-facing irrigation port may be positioned on a side of the catheter substantially opposite the lateral aspiration port.

The aspiration port may be lateral facing and the irrigation port may be lateral facing. The lateral-facing aspiration port may be positioned distally of the lateral-facing irrigation port or proximally of the lateral-facing irrigation port. The lateral-facing aspiration port may be configured to direct irrigation fluid in an axial direction toward the lateral-facing aspiration port.

The catheter may haves an irrigation tube in fluid communication with the irrigation lumen extending through and distally beyond a distal-facing aspiration port of the vacuum tube. The irrigation tube may have a lateral-facing irrigation port on a side of the irrigation tube closest to a center of the distal-facing aspiration port. A distal face of the irrigation tube may be configured to curve in a direction toward a center of the distal-facing aspiration port.

The aspiration port may be lateral facing and the irrigation port may be distal facing. The distal portion of the catheter may be curved or configured to be bent along a side of the catheter such that irrigation fluid from the irrigation port is directed at least partially in a proximal direction toward the lateral-facing aspiration port.

The distal steerable portion of the catheter may have a first steerable portion configured to bend in a first direction and a second steerable portion configured to bend in a second direction. The first steerable portion may be positioned at least partially distally of the second steerable portion. The first direction and the second direction may be the same or may be different. The first direction and the second direction may lie in the same plane or in different planes. The aspiration port may be within the first steerable portion, within the second steerable portion, or within a transition between the first steerable portion and the second steerable portion.

The removal device may include an ancillary device configured to be positioned laterally adjacent the catheter. The ancillary device may be a guidewire. The ancillary device may be axially translatable with respect to the catheter. The ancillary device may have a steerable distal portion. The ancillary device may be an irrigation tube. The irrigation tube may be configured to direct irrigation fluid toward a lateral-facing aspiration port on a side of the catheter. The removal device may have a shield configured to guide kidney stones toward an aspiration port on the catheter. The shield may have a mesh allowing fluid flow therethrough. The mesh may be sized to prevent passage of kidney stones through the shield. The shield may have a distal face positioned near or at a proximal edge of a lateral-facing aspiration port on the catheter. The shield may have a proximal face positioned near or at a distal edge of a lateral-facing aspiration port on the catheter. The shield may increase in width as it extends radially outward away from the catheter. The shield may be configured to wrap at least partially around a circumference of the catheter. The shield may have a collapsed configuration configured for insertion into the urethra and an expanded configuration configured for use within the bladder or kidney.

The removal device may have a handle attached to the proximal end of the catheter. The handle may have a port configured to prevent the delivery of suction pressure to a distal end of the catheter when the port is occluded and to allow the delivery of suction pressure to a distal end of the catheter when the port is unoccluded. The port may be further configured to prevent the delivery of irrigation fluid to a distal end of the catheter when the port is occluded and to allow the delivery of irrigation fluid to a distal end of the catheter when the port is unoccluded. Alternatively, the port may be further configured to prevent the delivery of irrigation fluid to a distal end of the catheter when the port is unoccluded and to allow the delivery of irrigation fluid to a distal end of the catheter when the port is occluded. The port may provide an open fluid communication between the distal end of the catheter and the ambient atmosphere outside of the body.

The removal device may have a lever configured to be pivoted in a first direction around a pivot point. The lever may be attached to a first pull wire, wherein pivoting the lever in the first direction retracts the first pull wire to cause a steerable portion of the catheter to bend toward a first side of the catheter along which the first pull wire extends. The lever may be attached to a second pull wire on an opposite side of the pivot point as the first pull wire, wherein pivoting the lever in a second direction, opposite the first direction, retracts the second pull wire to cause a steerable portion of the catheter to bend toward a second side of the catheter along which the second pull wire extends. The second side may be substantially opposite the first side.

The catheter may be configured to create an irrigation stream selected from the group consisting of: a flat stream, a fanned stream, and a conical stream. The catheter may have a plurality of irrigation ports. The irrigation ports may be configured to produce a single jet irrigation stream or to produce a shower effect of irrigation streams. The catheter may be configured to produce a vortex in an irrigation stream. The catheter may be configured to provide pulsatile irrigation. The catheter may be configured to provide pulsatile suctioning.

In a further aspect of the invention, disclosed herein is a method of removing a kidney stone from a kidney of a patient. The method comprises inserting a catheter into the urethra of the patient and advancing the catheter to a location within the kidney proximate to the kidney stone. The catheter has a distal portion having an aspiration port for providing suction and an irrigation port for providing irrigation fluid. The method further comprises moving the kidney stone such that it is aligned with the aspiration port, providing suction through the catheter to aspirate the kidney stone from the kidney without removal of the catheter from the kidney, and providing irrigation through the irrigation port.

Moving the kidney stone may comprise moving the kidney stone with the irrigation, moving the kidney stone using an ancillary device, and/or moving the kidney stone by contacting it with the catheter. The method may comprise contacting the kidney stone with the distal portion of the catheter. The distal portion of the catheter may be steerable.

In a further aspect of the invention, disclosed herein is a catheter for removal of kidney stones. The catheter has a tube portion, a handle portion coupled to the tube portion, and a plurality of pull wires. The tube portion has a vacuum lumen and an irrigation lumen. The vacuum lumen may have an inner diameter greater than 2 mm. The tube portion has a distal section and a proximal section. The distal section may have a length between 1 inch and 5 inches and a durometer of less than 40 D, and the proximal section may have a length greater than 15 inches and a durometer of greater than 50 D. The handle portion has a vacuum lumen having first and second openings and an irrigation lumen having first and second openings. The handle portion vacuum lumen first opening is in fluid communication with the tube portion vacuum lumen and the handle portion irrigation lumen first opening is in fluid communication with the tube portion irrigation lumen. The vacuum lumen second opening is configured to connect to a vacuum source and the irrigation lumen second opening is configured to connect to an irrigation source. The handle portion has an additional opening into the handle portion vacuum lumen such that the handle portion vacuum lumen is in fluid communication with ambient air outside of the handle through the side opening. The plurality of pull wires run from the tube portion distal section to one or more wire pull members on the handle portion. Pulling on one or more the pull wires using the wire pull members causes the tube portion distal section to bend in one or more directions.

In some embodiments, the vacuum lumen may have a diameter greater than 2.5 mm, a diameter between 2.5 mm and 3 mm, and/or a diameter of about 2.7 mm. The tube portion distal section may have a length from 1.5 to 3.5 inches, and/or a length from 2 to 3 inches. The tube portion distal section may have a durometer between about 30 D to 39 D and/or a durometer of about 35 D. In some embodiments, the tube portion distal section may have a durometer between about 30D and 55D. In some embodiments, the durometer may be less than 30D. The tube portion proximal section may have a length of 20 inches to 30 inches. The tube portion proximal section may have a durometer of 55 D to 70 D, a durometer of 60 D to 65 D, and/or a durometer of about 63 D. The tube portion may have a middle section between the proximal and distal sections. The middle section may have a length between 2 inches and 5 inches and a durometer between 40 D and 60 D. The tube portion middle section may have a length from 3 inches to 4 inches. The tube portion middle section may have a durometer between 50 D and 60 D and/or a durometer of about 55 D.

The tube portion vacuum lumen may be formed by an inner tube and the tube portion irrigation lumen may be formed by an outer tube surrounding the inner tube. The inner tube may have an outer liner, an inner liner, and a wire braid. In some embodiments, the outer liner may comprise PEBAX®, nylon, and/or other plastics. In some embodiments, higher durometer regions (e.g., more proximal regions) may comprise nylon and lower durometer regions (e.g., more distal regions) may comprise PEBAX®. The inner liner may comprise PEBAX®, PTFE, polypropylene, polyurethane, nylon, and/or other plastics. The wire braid may be encapsulated within the outer and inner liners. The catheter may comprise a plurality of tubes through which the pull wires extend. The tubes may comprise PTFE. The catheter may comprise a plurality of tubes extending through the wire braid, wherein the pull wires extend through the tubes. The side opening may be coverable by a human finger.

The one or more wire pull members may each include a lever pivotably coupled to the handle portion. The one or more wire pull members may include two wire pull members having a first lever and a second lever. The first lever and second lever may be positioned on substantially opposite sides of the handle portion. The plurality of pull wires may include a first pull wire and a second pull wire, the first pull wire being attached to the first lever and the second pull wire being attached to the second lever. The first lever may be coupled to the second lever such that extending the first lever in a distal direction retracts the second lever in a proximal direction and extending the second lever in the distal direction retracts the first lever in the proximal direction. The catheter may not include a visualization member or lumen capable of receiving an endoscope. The catheter may include a stone trap in-line between the vacuum lumen of the handle portion and the vacuum source, the stone trap configured to collect stones removed via the vacuum lumen of the tube portion. The catheter may have a diameter of a distal opening in the vacuum lumen is smaller than a maximum inner diameter of the vacuum lumen. The catheter may have an inner diameter of the vacuum lumen tapers from proximal to distal over at least a portion of the vacuum lumen's length.

In a further aspect of the invention, disclosed herein is a method of removing kidney stones from a kidney of a patient. The method includes inserting a steerable catheter through the urethra, bladder, and ureter and into the kidney of the patient and inserting a distal portion of the catheter into a first calyx of the kidney. The catheter has a vacuum lumen and an irrigation lumen. The vacuum lumen may have a diameter greater than 2 mm. The vacuum lumen and irrigation lumen have openings at a distal end of the catheter. The irrigation lumen is in fluid communication with a fluid source and the vacuum lumen is in fluid communication with a vacuum source. The method further includes providing fluid communication between the vacuum lumen and ambient air outside of the patient. While fluid communication is provided between the vacuum lumen and ambient air outside of the patient, irrigation fluid is continuously provided through the irrigation lumen and out of the irrigation lumen distal end into the first calyx until irrigation fluid returns through the vacuum lumen to outside of the patient. After the irrigation fluid returns through the vacuum lumen to outside of the patient, the fluid communication between the vacuum lumen and ambient air outside of the patient is terminated such that the vacuum source provides negative pressure to the vacuum lumen. The method further comprises bending the distal portion of the catheter within the first calyx in a first bending direction by manipulating a steering member outside of the patient and removing one or more kidney stones from the first calyx to outside of the patient by aspiration of the kidney stone through the vacuum lumen. After removing the one or more kidney stones from the first calyx, fluid communication between the vacuum lumen and ambient air outside of the patient is reestablished. The method further includes removing the distal portion of the catheter from the first calyx and inserting it into a second calyx of the kidney without use of a guidewire or endoscope. The method further includes providing irrigation fluid through the irrigation lumen and out of the irrigation lumen distal end into the second calyx. The fluid communication between the vacuum lumen and ambient air outside of the patient is terminated such that the vacuum source provides negative pressure to the vacuum lumen while the distal portion of the catheter is in the second calyx. The method further includes bending the distal portion of the catheter within the second calyx by manipulating the steering member outside of the patient. All of the steps of the method are conducted without any direct visualization from within the kidney.

One or more of the steps may be conducted with indirect visualization from outside the patient. The indirect visualization may be fluoroscopy.

In some embodiments, irrigation fluid may be continuously provided through the irrigation lumen while the distal portion of the catheter is removed from the first calyx and inserted into the second calyx. After inserting the distal portion of the catheter into the second calyx, the method may include continuously providing irrigation fluid through the irrigation lumen and out of the irrigation lumen distal end into the second calyx until irrigation fluid returns through the vacuum lumen to outside of the patient. The step of terminating the fluid communication between the vacuum lumen and ambient air outside of the patient when the distal portion of the catheter is in the second calyx may be performed after the irrigation fluid returns from the second calyx through the vacuum lumen to outside of the patient. The method may further include inserting the distal portion of the catheter into one or more additional calyces and providing irrigation fluid through the irrigation lumen and out of the irrigation lumen distal end into the one or more additional calyces. The fluid communication between the vacuum lumen and ambient air outside of the patient may be terminated such that the vacuum source provides negative pressure to the vacuum lumen while the distal portion of the catheter is in the one or more additional calyces. The method may further include bending the distal portion of the catheter within the one or more additional calyces by manipulating the steering member outside of the patient. The first calyx, second calyx, or one or more additional calyces may include a calyx within the lower pole of the kidney.

After bending the distal portion of the catheter within the first calyx and while the vacuum source provides negative pressure to the vacuum lumen, the method may include rotating the catheter in a first rotation direction, bending the distal portion of the catheter within the first calyx in a second bending direction opposite the first bending direction, and rotating the catheter in a second rotation direction opposite the first rotation direction. Rotating the catheter in the first direction may include rotating the catheter approximately 180 degrees in the first direction. Bending the distal portion of the catheter in the second bending direction may include bending the catheter such that a distal tip of the catheter is returned to approximately the same position it was in before rotating the catheter in the first direction. Rotating the catheter in the second direction may include rotating the catheter approximately 180 degrees in the second direction such that the distal tip of the catheter has traced a substantially circular trajectory.

The method may further include removing one or more kidney stones from the second calyx to outside of the patient by aspiration of the kidney stone through the vacuum lumen. Removing the distal portion of the catheter from the first calyx may be performed while terminating the fluid communication between the vacuum lumen and ambient air outside of the patient such that the vacuum source provides negative pressure to the vacuum lumen.

BRIEF DESCRIPTION OF THE DRAWINGS

FIG. 3A depicts a cross section taken along the longitudinal axis. FIG. 3B depicts a cross section intersecting the longitudinal axis.

FIGS. 4A-4G schematically depict various examples of lateral aspiration ports.

FIGS. 6A-6C schematically depict various examples a cross section of a catheter comprising a vacuum tube and an irrigation tube.

FIGS. 7A-7B schematically depict examples of the dimensions, durometers, and other parameters of a vacuum tube used as the main body of a removal device catheter.

FIGS. 8A-8B schematically depict an example of a removal device handle. FIG. 8A illustrates a side view. FIG. 8B illustrates a cross section of the side view illustrated in FIG. 8A.

FIGS. 10A-10B schematically illustrate device components that may be used with pull wires for steering a steerable portion of the catheter. FIG. 10A illustrates an example of a handle comprising levers for manipulating two pull wires. FIG. 10B illustrates a pull wire ring used to introduce pull wires to the catheter.

FIGS. 11A-11F schematically illustrate another example of a device handle configured to operate pull wires. FIG. 11A illustrates a perspective view of the handle. FIG. 11B illustrates a side view of the handle. FIG. 11C illustrates a cross section of the side view depicted in FIG. 11B. FIG. 11D illustrates a top view of the handle. FIG. 11E illustrates a front view of the lever used to control the pull wires. FIG. 11E illustrates a cross section of a distal portion of the device handle including pull wires.

FIG. 12 schematically illustrates another example of a handle which comprises three fluid ports.

FIGS. 17A-17E schematically depict various examples of a removal device comprising a catheter comprising at least aspiration and a secondary device positioned alongside the catheter on a safety guidewire. FIG. 17A illustrates the catheter and safety guidewire. FIG. 17B illustrates the catheter and an ancillary irrigation tube. FIG. 17C illustrates the catheter and a shield device in an expanded configuration. FIG. 17D depicts the catheter and a shield device configured to wrap around the catheter. FIG. 17E depicts the catheter and a shield device in a collapsed configuration.

FIG. 18A depicts a perspective view of the distal end. FIG. 18B depicts a side view of the distal end adjacent a ruler.

FIGS. 20A-20D schematically illustrates the dimensions and configuration of an example of an obturator configured to be used with the removal device. FIG. 20A illustrates a side view of the obturator. FIG. 20B illustrates a distal end view of the obturator. FIG. 20C illustrates a cross section of a proximal end of the obturator/introducer. FIG. 20D illustrates a cross section of a distal end of the obturator/introducer.

FIG. 21A illustrates a side view. FIG. 21B illustrates a cross section of the side view illustrated in FIG. 21A.

DETAILED DESCRIPTION

Disclosed herein are systems, devices, and methods for the guided removal of objects in vivo. In particular, the systems, devices, and methods may be adapted to traverse compact areas, such as the urinary tract, and to remove debris, such as kidney stones or fragments of kidney stones, via aspiration through a vacuum tube. As used herein, the term "kidney stones" may refer to fragments of kidney stones, including fragments that have been created by therapeutic fracturing of kidney stones, such as with the device described herein or by another device.

Figure 1:
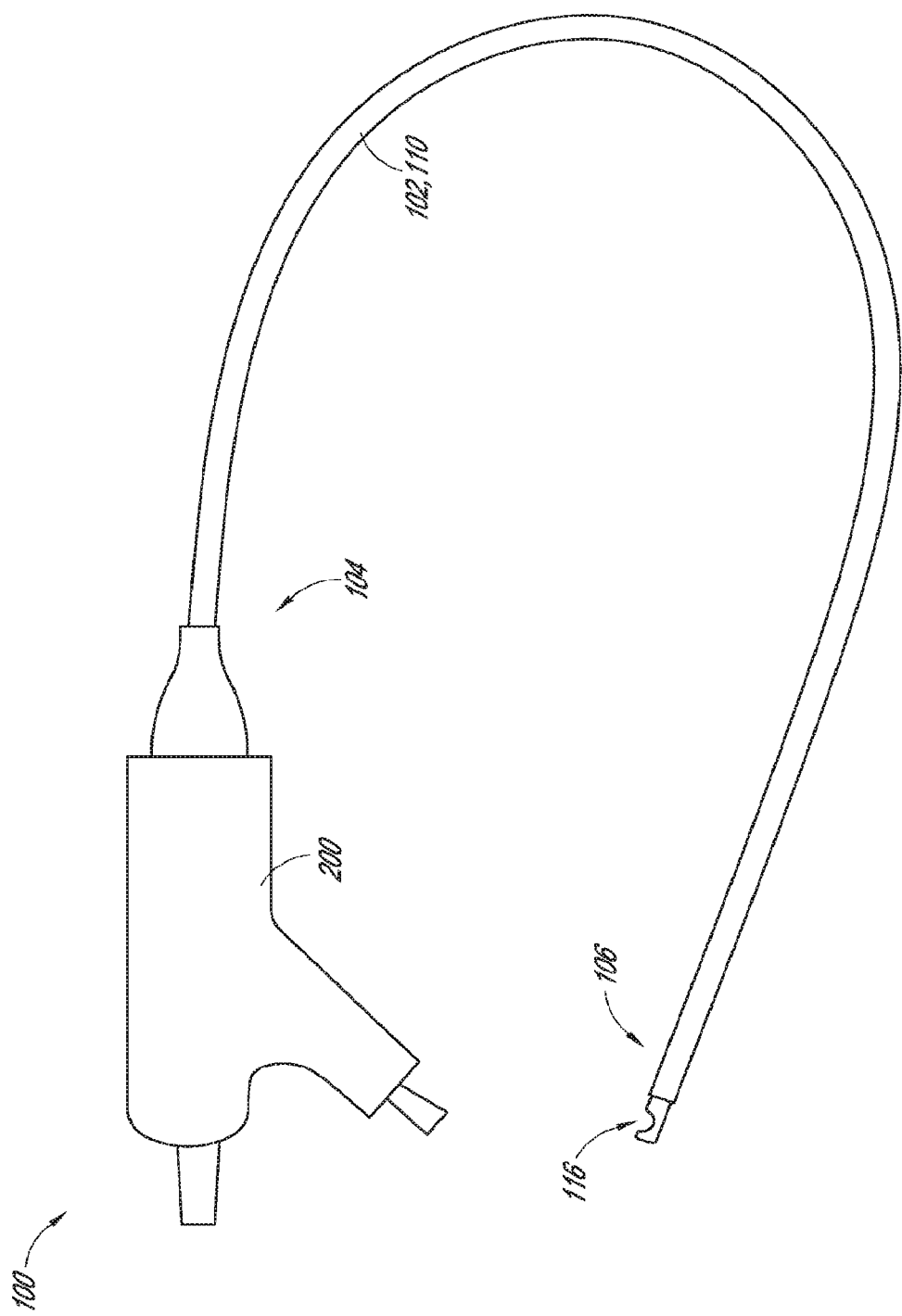
FIG. 1 illustrates an example of a kidney stone removal device.
Figure 2A:
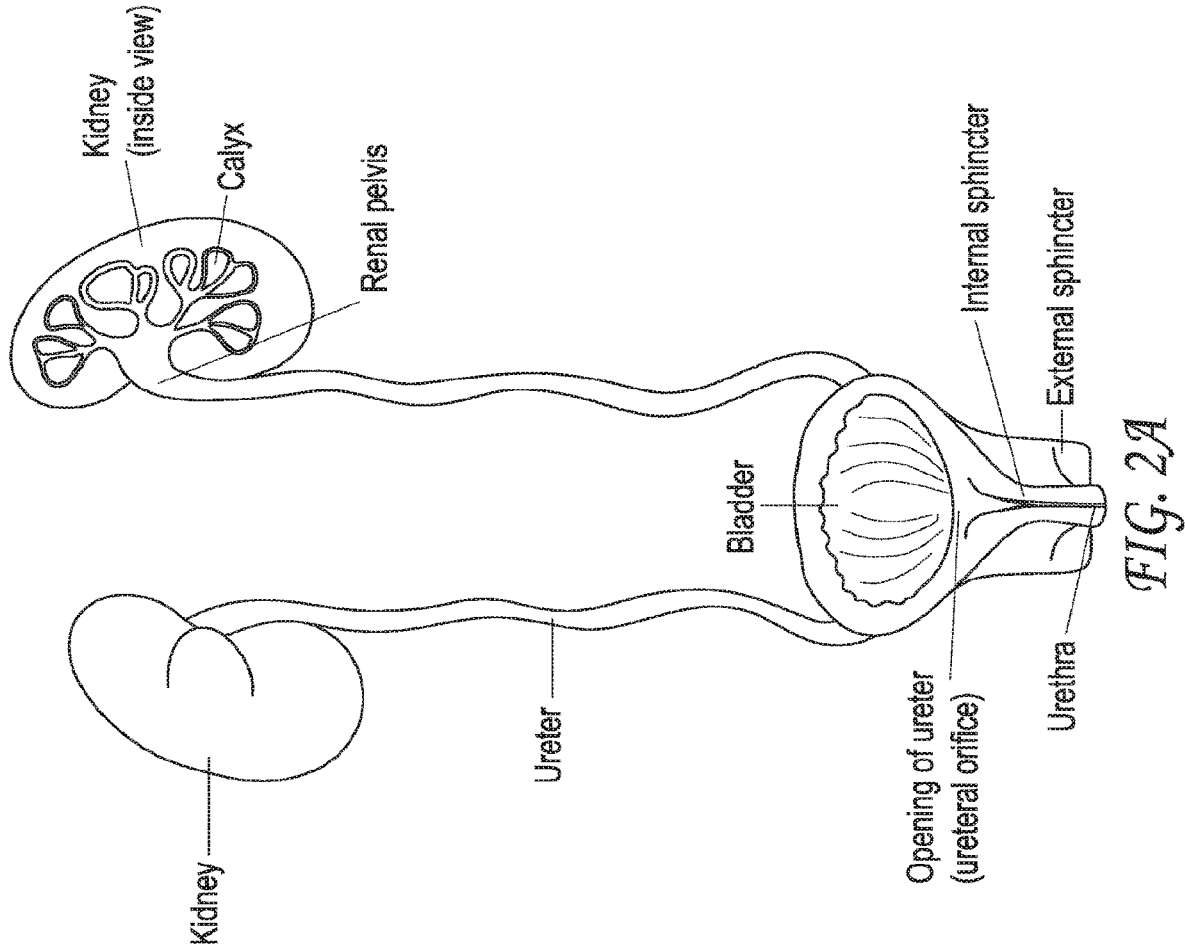
FIG. 2A schematically depicts the anatomy of the human urinary tract.
Figure 2B:
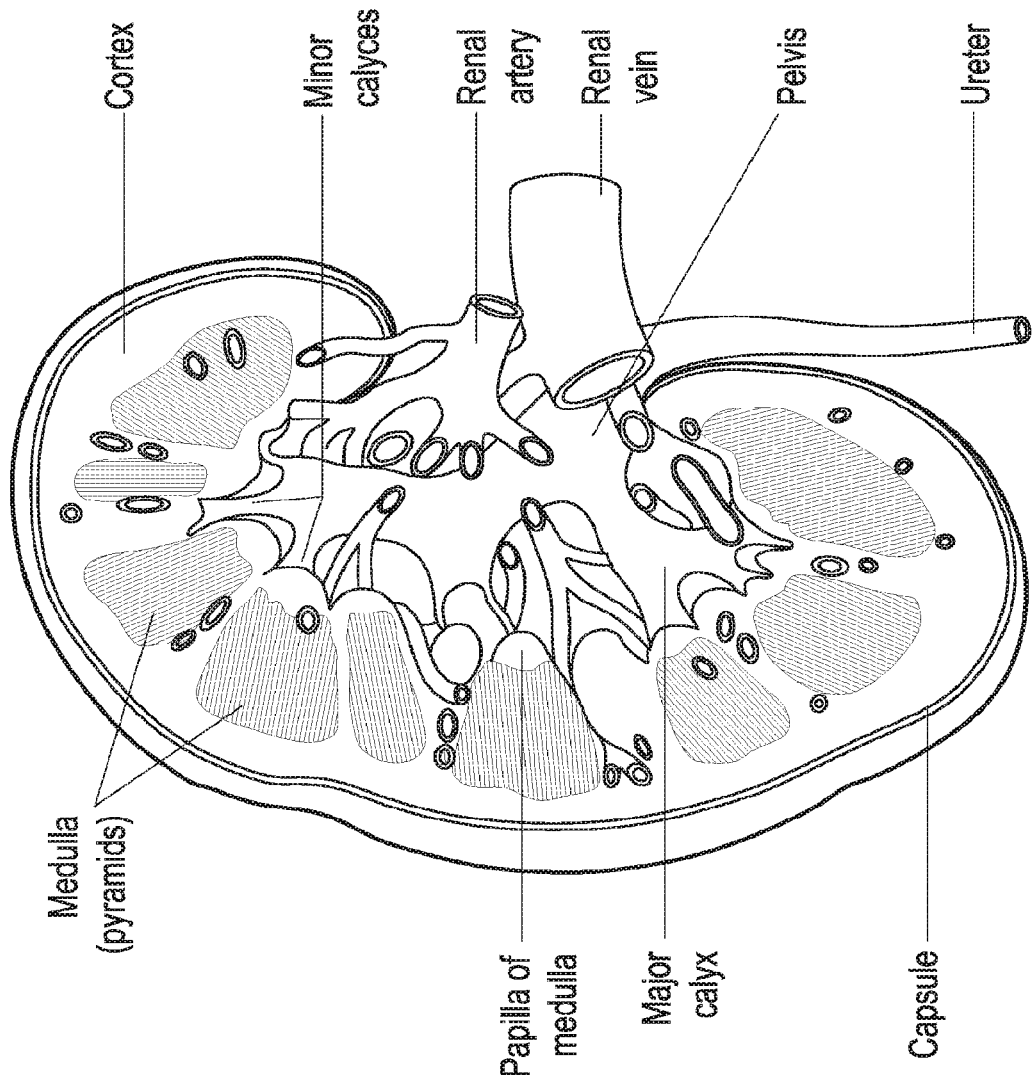
FIG. 2B schematically depicts the anatomy of the human kidney.

FIG. 1 illustrates an image of an example of a removal device 100. In some embodiments, a removal device 100 comprises a catheter 102 configured to navigate the urinary tract. FIG. 2A schematically depicts anatomical structures of the urinary tract. FIG. 2B schematically depicts the anatomy of the kidney. The catheter 102 may be configured for introduction through the urethra and may be configured to extend through the bladder, through the ureter, and into the kidney. The kidney may be comprised of three poles —an upper pole, middle pole, and lower pole—that approximately correspond to three major calyces. The catheter may have a proximal end 104 and a distal end 106. The catheter may define a longitudinal axis extending form the proximal end 104 to the distal end 106. The distal end 106 may be configured to extend into the kidney as far as the major or minor calyces of the kidney. The proximal end 104 may be configured to remain outside the body. The proximal end 104 may comprise a handle 200 for a user to hold the catheter 102. The handle 200 may comprise one or more grips for facilitating the holding and manipulation of the catheter 102 by the user. The handle 200 may be used to advance and/or retract the catheter 102 through the urinary tract or other physiological tract. The handle 200 may comprise one or more controls for controlling the operation of the catheter, such as irrigation, suction/aspiration, and/or movement, such as rotation, advancement, retraction, and/or lateral movement of the catheter (e.g., a distal portion), which may be steerable.

Figure 3B:
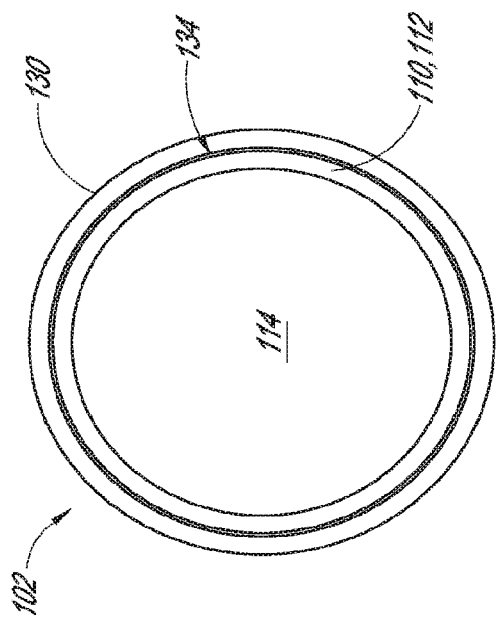
FIGS. 3A-3B schematically depict an example of a distal end of a catheter comprising a vacuum tube and an irrigation tube.
Figure 3A:
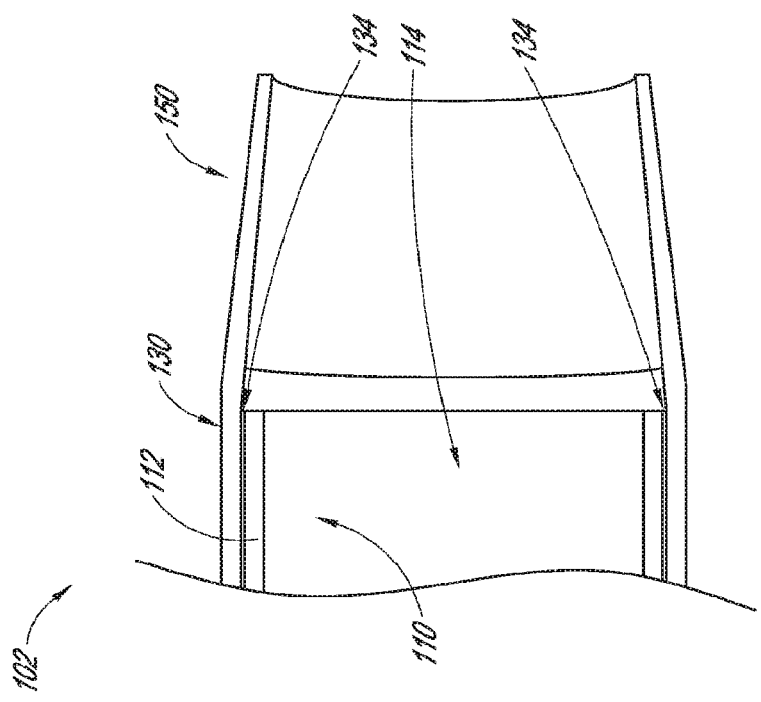

FIGS. 3A-3B schematically illustrates an example of a distal end 106 of the catheter 102. FIG. 3A depicts a side view of a cross-section of the distal end 106 of the catheter 102 along the longitudinal axis. FIG. 3B depicts a cross-section orthogonal to the longitudinal axis of the catheter 102 near the distal end 106, but proximal to a nozzle, described elsewhere herein. The catheter 102 may comprise a vacuum tube 110. In some embodiments, the vacuum tube 110 may constitute the main body of the catheter 102. The vacuum tube 110 may comprise a sidewall 112 and a vacuum lumen 114 formed within the inner diameter of the sidewall 112. The sidewall 112 may be substantially cylindrical in shape. The size and shape of the vacuum lumen 114 may be configured for aspiration of debris, such as kidney stones. In some embodiments, the size (e.g., diameter) of the vacuum lumen may be maximized, as described elsewhere herein, to optimize the removal of larger kidney stones or other debris. The vacuum lumen 114 may extend to the proximal end 104 of the catheter 102 or at least to a proximal portion of the catheter 102 configured to be positioned outside of the body, such that debris may be removed from the body through the vacuum lumen 114.

The vacuum tube 110 may comprise an open distal face, such that the distal face of the vacuum tube 110 forms an aspiration port 116 in fluid communication with the vacuum lumen 114 through which debris may enter the vacuum lumen 114. Suction may be provided to the vacuum lumen 114 by coupling a proximal end of the vacuum lumen 114 to a source of negative pressure (e.g., a wall suction outlet, a negative pressure pump, or any other suitable means known in the art). In some embodiments, the distal face may be partially closed and/or a nozzle 150 may be formed at and/or on the distal end of the vacuum tube 110. In some embodiments, the nozzle 150 may form one or more apertures or aspiration ports 116 on the distal face of the vacuum tube 110 that are smaller in cross-sectional area than the area formed by the inner diameter of the sidewall 112 along the length of the catheter 102. Maximizing the size (e.g., the cross-sectional area) of the one or more aspiration ports 116 may facilitate removal of larger debris from the body within a physiological space, such as the urinary tract, which may restrict the overall diameter of the catheter 102.

One or more aspiration ports 116 may, additionally or alternatively, be formed by lateral apertures in the sidewall 112 of the vacuum tube 110. FIGS. 4A-4G schematically depict various examples of possible arrangements of aspiration ports. Aspiration ports 116 formed in the sidewall 112 may face a lateral direction, substantially orthogonal to the longitudinal direction of the catheter 102 over the length in which the ports are formed. Any of the examples depicted may also include one or more distal-facing aspiration ports 116 formed in the distal face of the catheter 102 or may comprise no distal facing aspiration ports 116. In some embodiments, one or more lateral aspiration ports 116 may be formed in the sidewall 112 along a distal length of the vacuum tube 110 (e.g., the last 50 mm, the last 30 mm, the last 25 mm, the last 20 mm, the last 15 mm, the last 10 mm, the last 5 mm, more than the last 50 mm, or less than the last 5 mm of the vacuum tube 110). In some embodiments, the catheter 102 may only comprise lateral aspiration ports 116 and the distal face of the catheter may be closed. In some embodiments, the distal face may be substantially rounded, domed, bullet-shaped, and/or comprise another atraumatic configuration. Aspiration ports 116 may be formed in a non-flat (e.g., rounded) distal face and may face a distal direction, a lateral direction, or a direction there between.

In some embodiments, the aspiration ports 116 may be substantially circular in shape. In some embodiments, the aspiration ports 116 may be other shapes (e.g., ovoid, rectangular, etc.). In some embodiments, the diameter of an aspiration port 116 may be 1 mm, 2 mm, 3 mm, 4 mm, 5 mm, 6 mm, 7 mm, 8 mm, 9 mm, 10 mm, or more than 10 mm. The removal device 100 may be sized to remove stones or other debris as large as 0.5 mm, 0.6 mm, 0.7 mm, 0.8 mm, 0.9 mm, 1 mm, 1.25 mm, 1.5 mm, 1.75 mm, 2 mm, 3 mm, 4 mm, 5 mm, or more than 5 mm. The circumferential span of an aspiration port 116 may comprise approximately less than 5%, 5%, 10%, 20%, 25%, 30%, 40%, 50%, or more than 50% of the circumference of the vacuum tube 110. In embodiments comprising a plurality of lateral aspiration ports 116, one or more aspiration ports 116 may be spaced along a length of the vacuum tube 110 and/or one or more aspiration ports 116 may be axially aligned and spaced across the circumference of the vacuum tube 110 (e.g., offset by 45 degrees, 90 degrees, 180 degrees, etc.). One or more aspiration ports 116 which are axially spaced may be circumferentially aligned or they may be circumferentially offset (e.g., offset by 45 degrees, 90 degrees, 180 degrees, etc.). Circumferentially offset aspiration ports 116 may somewhat overlap in the circumferential direction or may not overlap at all. In embodiments comprising multiple aspiration ports 116, the aspiration ports 116 may comprise the same or different shapes and/or dimensions. One or more aspiration ports may be positioned at a distal corner of the catheter 102 such that it opens in both a distal-facing and lateral-facing direction (e.g., FIG. 4G).

In some embodiments, as described elsewhere herein, an external component may surround the vacuum tube 110 (e.g., an irrigation tube 130). In some embodiments comprising an external component, lateral aspiration ports 116 may be positioned distally of a distal end of the external component or the lateral aspiration ports 116 may extend through the external component. For example, the external component may comprise an aperture of the same size as the aperture formed in the vacuum tube 110 and the external component may be sealed to vacuum tube 110 around the aperture such that the aspiration port 116 extends through the sidewall of the vacuum tube 110 and the sidewall of the external component.

In some embodiments, the catheter 102 may comprise more than one vacuum tube 110 and/or a single vacuum tube 110 may be formed with more than one vacuum lumens 114. For example, the sidewall 112 may branch and extend inward to internally divide the vacuum tube 110 into multiple lumens of the same or different shape and/or cross-sectional areas). FIGS. 5A-5H schematically depict various examples of a multi-lumen vacuum tube 110 formed by the sidewall 112. The sidewall 112 may extend into the vacuum lumen 114 to form one or more vacuum lumens 114 adjacent the inner diameter of the vacuum tube 110 or the sidewall 112 may extend outward to form one or more vacuum lumens 114 adjacent the outer diameter of the vacuum tube 110. In some embodiments, the thickness of the sidewall 112 may be sufficient such that vacuum lumens 114 may be formed in the sidewall, extending axially along the length of the vacuum tube 110, without altering the shape (e.g., cylindrical) of the vacuum tube 110 and central vacuum lumen 114. In some implementations, one or more vacuum lumens 114 may be too small in size (e.g., cross-sectional area or diameter) to allow passage of a kidney stone, but may generate suction which is useful for moving a kidney stone or other debris toward an aspiration port 116 which is configured to remove matter from the physiological space. A vacuum lumen 114 may be cylindrical or otherwise substantially round in shape. A vacuum lumen 114 may be non-cylindrical in shape. In some embodiments, one or more vacuum lumens 114 are elongate in shape. In some embodiments, the vacuum lumen includes a taper of its inner diameter from proximal to distal along a portion or the entire length of the vacuum lumen. For example, in some embodiments, the vacuum lumen includes a tapered distal tip such that the diameter of the aspiration port is smaller than the inner diameter of the vacuum lumen. This feature can advantageously reduce clogging of the vacuum lumen with debris (e.g., by reducing the size of the kidney stones that can enter the vacuum lumen). In other embodiments, the vacuum lumen includes a longer taper from proximal to distal, for example, along substantially the entire length of the vacuum lumen. In some embodiments, the diameter of the aspiration port is from 0.05 mm to 0.5 mm, 0.05 mm to 0.3 mm, 0.05 mm to 0.2 mm, 0.05 to 0.1 mm, or 0.08 mm to 0.2 mm smaller than the maximum inner diameter of the vacuum lumen. In some embodiments, the inner diameter of the vacuum lumen increases continually from the distal end to the proximal end. In some embodiments, the inner diameter of a vacuum lumen within a handle to which the vacuum lumen is coupled also increases from distal to proximal within the handle. Thus, in some embodiments, the inner diameter of the combined catheter and handle vacuum lumens continuously increases from distal to proximal such that the minimum inner diameter is at the distal tip of the catheter, and the maximum inner diameter is at a fluid port on the handle, which is to be coupled to a vacuum source.

The catheter 102 may comprise one or more irrigation lumens 134 for providing irrigation at or near the distal end 106 of the catheter 102. Irrigation may be particularly beneficial for use in the kidney (e.g., for removing kidney stones). Irrigation may dislodge kidney stones from tissue and/or may provide enough buffer/cushion/barrier to prevent the suction from sucking tissue into the aspiration port 116, which may occlude the vacuum lumen 114 and inhibit aspiration of kidney stones. Suction of delicate kidney tissue into contact with the catheter 102 may pose a safety hazard, as the suctioning may cause damage or irritation of the tissue (e.g., may cause bleeding). For this reason, it is conventional not to use suctioning within the kidney without ureteroscope or direct visualization, especially within the calyces, to remove kidney stones. Providing a sufficient level of irrigation (relative to the level of suctioning) which inhibits, reduces, and/or prevents suctioning of kidney tissue may improve the safety and/or efficacy of the removal device 100. This safety feature may be particularly advantageous for blind procedures which do not utilize direct visualization. Providing too much irrigation may, in some embodiments, result in over-pressurization of the kidney which can have adverse consequences. Providing a valve or port establishing fluid communication between the ambient atmosphere and the kidney may reduce the chance of or prevent the risk of overpressurization. Each irrigation lumen 134 may terminate in one or more openings, which serve as irrigation ports 136 in fluid communication with the irrigation lumen 134 through which an irrigation fluid may be delivered from the irrigation lumen 134 into the body. In some embodiments, the distal end face of the irrigation lumen 134 may be open such that the opening forms an irrigation port 136. In some embodiments, the distal end of the irrigation lumen 134 may be partially closed but may comprise one or more apertures forming one or more irrigation ports 136 and/or a nozzle may be incorporated into the opening, as described elsewhere herein, or at the opening, such as the nozzle 150 depicted in FIG. 3A.

In some embodiments, the one or more irrigation lumens 134 may be formed by one or more irrigation tubes 130, which may be separate structures from the vacuum tube 110. FIGS. 6A-6C schematically depict various examples of arrangements of vacuum tubes 110 and irrigation tubes 130 within the catheter 102. The irrigation tubes 130 may be positioned internally within the vacuum tube 110 (FIG. 6A), externally adjacent to the vacuum tube 110 (FIG. 6B), and/or externally surrounding the vacuum tube 110 (FIG. 6C as well as FIGS. 3A and 3B). The irrigation tubes 130 may be rigidly affixed to the vacuum tube at one or more points (e.g., along the entire length of the catheter 102), may be coupled to the vacuum tube 110 by the handle 200, or may be uncoupled. In some embodiments, the one or more irrigation lumens 134 may be formed within the sidewall of the vacuum tube 110. Any of the lumens depicted in FIGS. 5A-5H may be used alternatively as irrigation lumens 114. In some embodiments, lumens of smaller size (e.g., cross-sectional area) may be more suited for providing irrigation than for aspiration, depending on the size of the debris being removed. For example, a plurality of irrigation lumens 134 may be formed in a cylindrical sidewall of the vacuum tube 110 such that a plurality of irrigation ports 136 circumferentially surrounds the aspiration port 116 (e.g., FIG. 5E).

In some embodiments, lateral irrigation ports 136 may be formed along an irrigation lumen 134, in addition to or alternatively to a distal opening irrigation port 136, in the same manner in which lateral aspiration ports 116 may be formed (FIGS. 4A-4G). An irrigation lumen 134 may be substantially cylindrical in shape. An irrigation lumen 134 may be non-cylindrical in cross-sectional shape. In some embodiments, the irrigation lumen 134 may run parallel with the longitudinal axis of the catheter 102. In some embodiments, the irrigation lumen 134 may not run parallel with the longitudinal axis of the catheter 102 and/or may run parallel along lengths of the catheter 102 but experience curves or other changes in direction, such as near the irrigation port 136. In some embodiments, one or more irrigation lumens 134 are elongate in cross-sectional shape. For example, the sidewall of the vacuum tube 110 may comprise thin irrigation lumens 134 that form arcs expanding approximately less than 5%, 5%, 10%, 20%, 25%, 33%, 50%, or greater than 50% of the circumference of the vacuum tube 110 (e.g., FIGS. 5F and 5G). The one or more irrigation lumens 134 may be coupled at their proximal ends to a source of pressurized irrigation fluid for forcing irrigation fluid through the irrigation lumens 134, such as a syringe, a wash bottle, a positive displacement pump, an IV bag, or any other suitable fluid irrigation source known in the art (e.g., a single action pump system such as provided by Boston Scientific). In embodiments comprising an electronic pump, a controller comprising appropriate software may be used to control the operation of the pump. In some embodiments, the irrigation fluid may comprise water, saline, or any other physiologically suitable fluid.

In some embodiments, additional lumens may be formed along the length of the catheter 102. For example, lumens may be configured for receiving an introducer or obturator, a visualization device such as an endoscope (e.g., a ureteroscope), and/or a navigation mechanism such as a guidewire. In some embodiments, a specific lumen may be formed for the introduction of each additional device from a separate tube structure or from the sidewall of an existing lumen as described with respect to the vacuum lumens 114 and/or irrigation lumens 134. In some embodiments, a vacuum lumen 114 and or an irrigation lumen 134 may be configured to receive one or more of these devices (e.g., configured in size and/or shape). For example, the vacuum lumen 114 may be configured to receive an introducer and/or an irrigation lumen 134 may be configured to receive a guidewire. The ancillary devices may be configured to be used with the catheter 102 disclosed herein. For instance, an introducer may be sized and shaped to be received in and to fill the cross-sectional area of a vacuum lumen 114 in which an irrigation lumen 134 extends into the otherwise cylindrical lumen. These devices may be removed from the lumen prior to starting aspiration and/or irrigation, such as after the catheter 102 has been properly positioned in the ureter or kidney. In some embodiments, the catheter 102 comprising one or more vacuum lumens 114 and optionally one or more irrigation lumens 134, may be configured to be received in an outer sheath, such as a delivery sheath. The outer sheath may be optimized for introduction of the catheter 102 and/or other devices into the urinary tract. For example, the outer sheath may comprise a hydrophilic and/or lubricious coating, which facilitates insertion of the sheath into the urethra. The outer sheath may partially dilate the urethra. The outer sheath may protect the urethra and other portions of the urinary tract or other body lumen from damage as instruments are advanced within and/or retracted through the outer sheath. In some embodiments, the outer sheath may help navigate internal instruments through the body lumen, particularly if the internal instrument is relatively more flexible than the outer sheath. The outer sheath may comprise a coil and/or wire braid, as described elsewhere herein with respect to catheter 102, for providing enhanced structural integrity. The outer sheath may comprise a radiopaque marker or be fabricated from radiopaque materials for visualization during fluoroscopy. The catheter 102 may also be radiopaque or comprise radiopaque materials, such that it may be visualized under fluoroscopy.

Embodiments of the catheter 102 disclosed herein may comprise and/or may be used with any of the components disclosed in U.S. Patent Publication No. 2017/0319776 to Eisner et al., entitled "System and Method for Guided Removal from an In Vivo Subject," and filed Jul. 13, 2017, which is hereby incorporated by reference in its entirety. Also, the various components disclosed herein may be arranged in the same or similar fashion to the components in U.S. Patent Publication No. 2017/0319776. For example, the irrigation lumens 134 and vacuum lumens 114 may comprise any of the configurations disclosed therein.

In some embodiments, the vacuum tube 110 may form the main body of the catheter 102. The vacuum tube 110 may comprise a wire braid and/or coil as is known in the art. The braid and/or coil may help preserve the structural integrity of the catheter 102 under pressure (e.g., prevent kinking and/or collapsing of the lumen) and/or may help tailor the flexibility/rigidity of the catheter 102. The braid and/or coil may extend the entire length of the catheter 102 or may extend only a partial length of the catheter 102. For example, the vacuum tube 110 may comprise a wire ribbon. The wire ribbon may be stainless steel (e.g., 300 series stainless steel wire ribbon). The wire ribbon may be approximately 0.001 in by 0.005 inch. The wire ribbon may have a 0.010 inch pitch. The wire ribbon may be at least a 16 carrier, 24 carrier, or 28 carrier braid. The wire ribbon may be braided 1 over 2 under 2. The wire ribbon may comprise approximately 80 ppi. The wire ribbon may be braided 2 over 2 with 2 to 3 ends per carrier. The wire ribbon may be braided 2 over 1. The wire ribbon may be braided in a tri-axial pattern. The braid and/or coil may be sandwiched between an inner layer (e.g., Propel® or polytetrafluoroethylene (PTFE) inner liner) and an outer layer (e.g., polyether block amide such as PEBAX®) of the vacuum tube 110 sidewall 112. The outer layer may comprise barium sulfate ($BaSO_4$), in amounts such as about 40%. In some embodiments, the inner layer may be between about 0.012 to about 0.016 inches thick. The braid or coil may extend substantially from the proximal end 104 to the distal end 106 of the catheter 102, substantially along a proximal portion of the catheter 102, substantially along a distal portion of the catheter 102, or along an intermediate section of the catheter 102. In some embodiments, the inner layer and/or the outer layer may be formed of segments comprising variable durometers. The durometer may decrease in a distal direction such that the catheter 102 becomes progressively more flexible toward the distal end, which may be advantageous for navigating more tortuous pathways, such as the calyces of the kidney (e.g., bending the distal end 106 of the catheter 102 to reach into the lower pole of the kidney). In some embodiments, the braid may transition into a coil or vice-versa. The density of the wire braid (e.g., picks/length) or coil (e.g., pitch) may be used to modulate the flexibility/rigidity of the catheter 102 along its length. In some embodiments, the durometers of the various segments may be configured for providing specific amounts of curvature in steerable portions of the catheter 102, as described elsewhere herein. For example, the catheter 102 may comprise one or more curvable portions capable of achieving a radius of curvature of about 5.0 cm, 4.75 cm, 4.5 cm, 4.25 cm, 4.0 cm, 3.75 cm, 3.5 cm, 3.25 cm, 3.0 cm, 2.75 cm, 2.5 cm, 2.25 cm, 2.0 cm, 1.75 cm, 1.5 cm, 1.25 cm, 1.0 cm, 0.75 cm, 0.5 cm, less than 0.5 cm, or a value in a range defined therebetween. For instance, a distal portion of the catheter 102 may be capable of achieving a curvature such that the distal tip may be positioned within the lower calyx. In some embodiments, the catheter 102 may comprise a durometer of about 50D, 55D, 60D, 63D, 65D, 70D, 72D, 75D, 80D, 90D, 100D, less than 50D, greater than 100D, or a durometer selected from any range there between at the proximal end 104. In some embodiments, the catheter 102 may comprise a durometer of about 10D, 15D, 20D, 25D, 30D, 35D, 40D, 45D, 50D, less than 10D, greater than 50D, or a durometer selected from any range there between at the distal end 106. In some embodiments, the catheter 102 may comprise one or more intermediate durometers, such as durometers of about 35D, 40D, 45D, 50D, 55D, less than 35D, greater than 55D, or a durometer selected from any range there between. The intermediate durometer or durometers may be an amount or amounts between the proximal durometer and the distal durometer. The changes in durometer may be accomplished by material selection and/or thickness of one or more layers of the catheter (e.g., the outer layer), wherein thicker layers of the same material are generally stiffer than thinner layers of the same material. The catheter 102 may be configured to prevent kinking over its entire length or at least along a distal portion of the length. For example, the catheter 102 may be kink-free along at least the distal 50 mm of the length when forming a bend with a radius of curvature of 13 mm.

FIGS. 7A-7B schematically depict dimensions and other parameters of a vacuum tube 110 used to form the catheter 102. The catheter 102 may comprise three or more segments with decreasing durometer from a proximal to distal direction. For example, as shown in FIG. 7A, the catheter 102 may comprise a proximal 63D segment 105, an intermediate 35D segment 107, and a distal 25D segment 109. In another example, as shown in FIG. 7B, the catheter 102 may comprise a proximal 63D segment 105, an intermediate 55D segment 107, and a distal 35D segment 109. In some embodiments, the intermediate segment 107 may be omitted. In some embodiments, primarily for kidney stone removal, the total length of the catheter 102 may be at least about 30 cm, 35 cm, 40 cm, or longer than 40 cm. The length may be longer for male subjects than for female, subjects, by approximately 6-8 inches. In some embodiments, the length of the proximal segment 105 may be substantially greater than the length of the intermediate segment 107 and/or the length of distal segment 109, or even the length of the intermediate segment 107 and the distal segment 109 combined. For instance, the length of the proximal segment 105 may be about 25 inches and the length of the intermediate segment 107 and distal segment 109 may be about 6 inches combined (e.g., 5 inches and 1 inch, 4.5 inches and 1.5 inches, 4 inches and 2 inches, 3 inches and 3 inches, 2 inches and 4 inches, 1 inch and 5 inches, etc.). In some embodiments, the intermediate segment 107 may correspond to a generally flexible segment configured to bend for navigation into the kidney. In some embodiments, the distal segment 109 may correspond to a steerable segment configured to be articulated by pull wires 230 or other steering means. The pull wires 230 described elsewhere herein may be attached, for example, to either the distal section 109, the intermediate section 107, or both. The pull wires 230 may extend from the distal section 109 along the length of the vacuum tube to extend beyond the proximal end of the vacuum tube for engagement with a control feature. In some embodiments, the pull wires 230 are embedded within the wall of the vacuum tube. In some embodiments, the pull wires 230 extend through tubes 111, which are embedded within the wall of the vacuum tube. In some embodiments, the tubes 111 comprise PTFE. In some embodiments, the intermediate section 107 may be omitted. The distal section 109 may be between about 1-3 inches long.

The steerable segment may be very flexible such that the steerable segment may be actively bent to form tight curves (e.g., 180 degree bends or more). In some embodiments, the steerable segment may be bent to form curves equal to or greater than about 90 degrees, greater than about 100 degrees, greater than about 110 degrees, 120 degrees, 130 degrees, 140 degrees, 150 degrees, 160 degrees, 170 degrees, 180 degrees, 200 degrees, 240 degrees, 270 degrees, or more than 270 degrees. The catheter 102 may be configured to allow efficient stone transport through the vacuum lumen 114 even under these degrees of bending (e.g., without kinking). The steep drop-off in durometer, such as between a distal 109 and proximal 105 segment (including or not including intermediate segments 107) may promote a high degree of bendability at the transition configured for forming tight bends having small radii of curvatures. In embodiments, in which the catheter 102 comprises an outer tube surrounding the vacuum tube 110, such as a concentric irrigation tube 130, described elsewhere herein, the outer tube may also have a drop-off in durometer. The drop-off in durometer of the outer tube may promote bending of the outer tube along with the controlled bending of the vacuum tube 110. The drop-off may be positioned along the length of the catheter at the same point as the drop off in the vacuum tube 110. In some embodiments, the durometers of the outer tube may match the durometers of the vacuum tube 110 along equivalent lengths. In some embodiments, the durometers of the outer tube may be generally less than that of the vacuum tube 110 along equivalent lengths. For instance, the outer tube may have a proximal section having a durometer of about 55D and a distal section having a durometer of about 35D. In some embodiments, the distal section 109 may have a durometer less than about 35D. In some embodiments, the steerable segment is about 0.5 inches to about 6 inches long, about 0.8 inches to about 5 inches long, about 1 inch to about 4 inches long, or about 1 inch to about 3 inches long. In some embodiments, the inner diameter of the catheter 102 and/or vacuum tube 110 may be about 0.07 inches, 0.075 inches, 0.08 inches, 0.085 inches, 0.09 inches, 0.095 inches, 0.096 inches, 0.097 inches, 0.098 inches, 0.099 inches, 0.1 inches, 0.105 inches, 0.11 inches, 0.12 inches, 0.13 inches, 0.14 inches 0.15 inches, 0.175 inches, 0.2 inches, less than 0.07 inches, greater than 0.2 inches, or a diameter in any range defined there between. In some embodiments, the inner diameter of the vacuum tube 110 is greater than 0.1 inches, greater than 0.13 inches, greater than 0.14 inches, or greater than 0.15 inches. In some embodiments, the inner diameter of the vacuum tube 110 is between 0.1 inches and 0.3 inches, between 0.13 inches and 0.25 inches, between 0.14 inches and 0.23 inches, or between 0.14 inches and 0.2 inches. The inner diameter may be at least about 5 Fr 6 Fr, 7 Fr, 8 Fr, 9 Fr, 10 Fr, 11 Fr, 12 Fr, 13 Fr, 14 Fr, 15 Fr, or more than 15 Fr. In some embodiments, the outer diameter of the catheter 102 and/or vacuum tube 110 may be about 0.09 inches, 0.095 inches, 0.096, inches, 0.097 inches, 0.098 inches, 0.099 inches, 0.1 inches, 0.11 inches, 0.12 inches, 0.13 inches, 0.133 inches, 0.14 inches, 0.15 inches, 0.175 inches, 0.2 inches, 0.25 inches, less than 0.095 inches, greater than 0.25 inches, or a diameter in any range defined there between. The wall thickness of the of the catheter 102 and/or vacuum tube 110 may be about less than 0.005 inches, 0.005 inches, 0.006 inches, 0.007 inches, 0.008 inches, 0.009 inches, 0.01 inches, 0.011 inches, 0.012 inches, 0.013 inches, 0.014 inches, 0.015 inches, 0.016 inches, 0.017 inches, 0.018 inches, 0.019 inches, 0.02 inches, 0.025 inches, 0.03 inches, 0.04 inches, 0.05 inches, more than 0.05 inches, or a thickness from any range defined there between. The outer diameter may be at least about 6 Fr, 7 Fr, 8 Fr, 9 Fr, 10 Fr, 11 Fr, 12 Fr, 13 Fr, 14 Fr, 15 Fr, 16 Fr, or more than 16 Fr. In some embodiments, the wall thickness is about 0.432 inches. In some embodiments, the wall thickness is about 0.356 inches. In some embodiments, the wall thickness may be relatively thin or minimized in order to maximize the cross-sectional area and diameter of the vacuum lumen 114. The wall thickness may be as thin as possible while maintaining structural integrity sufficient to resist collapsing under vacuum pressure and/or kinking.

The example of the distal end 106 of the catheter 102 depicted in FIGS. 3A-3B illustrates one possible configuration of a vacuum tube 110 and an irrigation tube 130. The vacuum tube 110 may comprise a cylindrical sidewall 112 and may terminate in a distal open face forming an aspiration port 116. The irrigation tube 130 may be configured to receive the vacuum tube 110 as shown, forming an annular irrigation lumen 134 and an annular irrigation port 136 surrounding the vacuum tube 110. The distal end of the irrigation tube 130 may extend distally beyond the distal end of the vacuum tube 110 forming a nozzle 150, as described elsewhere herein. The nozzle 150 may decrease in thickness as it extends distally. The nozzle 150 may comprise a decreasing outer diameter and/or a decreasing inner diameter as it extends distally. The nozzle may be relatively more flexible than the remaining length of the irrigation tube 130. In some embodiments, the irrigation tube 130 may be relatively more flexible and/or compressible than the vacuum tube 110. The irrigation tube 130 (i.e. the inner diameter or the inner and outer diameter) may comprise a somewhat expandable diameter. For example, the irrigation tube 130 may comprise an unexpanded diameter when irrigation fluid is not forced through the irrigation lumen 134 and the pressurized irrigation fluid may slightly expand the diameter of the irrigation lumen 134 or the diameter of the irrigation tube 130 altogether when irrigation fluid is forced through the irrigation lumen 134. The unexpanded diameter may be configured to fit closely around the outer diameter of the vacuum tube 110. The unexpanded diameter may facilitate insertion of the catheter 102 in the urethra or other constricted space of the body. The distal end of the vacuum tube 110 may be positioned further back in the proximal direction from the distal end of the irrigation tube 130 than as shown in FIG. 3A.

In some embodiments, the distal end of the vacuum tube 110 may be approximately aligned with the distal end of the irrigation tube. In other embodiments, the distal end of the vacuum tube 110 may be positioned distally beyond the distal end of the irrigation tube 130. The irrigation tube 130 may be relatively soft (e.g., 35D) and may be softer than the vacuum tube 110. Positioning the distal end of the irrigation tube 130 proximally to the distal end of the vacuum tube 110 may prevent or reduce the likelihood or degree of the irrigation tube 130 buckling, collapsing, stretching, and/or sliding forward or backward over the vacuum tube 110 when the vacuum tube 110 is bent. In some embodiments, the distal end of the irrigation tube 130 may be positioned at least approximately 1 mm from the distal end of the vacuum tube 110 in an unbiased configuration. The distal end of the irrigation tube 130 may be positioned at least distally enough such that it positioned beyond a curve in the catheter and the irrigation is aligned in the same direction as the aspiration. In some embodiments, the distal end of the irrigation tube 130 may be configured such that it does not advance within at least approximately 1 mm of the distal end of the vacuum tube 110 upon bending the catheter 102. In some embodiments, the distal end of the irrigation tube 130 may be configured such that it does not advance any further than approximately 1 mm from the distal end of the vacuum tube 130 upon bending of the catheter 102. In some embodiments, the distal end of the irrigation tube 130 may be configured such that it sits somewhere between approximately the distal end of the vacuum tube 110 and approximately 1 mm proximally back from the distal end of the vacuum tube 110 during use. In some embodiments, the distal end of the irrigation tube 130 may be configured such that it sits somewhere between approximately 1 mm back proximally from the distal end of the vacuum tube 110 and approximately 1 mm forward distally from the distal end of the vacuum tube 110 during use.

FIGS. 8A-8B schematically illustrate an example of a handle 202 attached to a proximal end of the catheter 102. The handle 202 may include the same or similar features as other handles described elsewhere herein. FIG. 8A depicts a side view of the handle 202. FIG. 8B depicts a cross section of the side view depicted in FIG. 8A. The handle 202 may be configured for use with a catheter 102 such as that depicted in FIGS. 3A-3B. The handle 202 may comprise a Y-shaped coupling 220 having two fluid ports 222. The fluid ports 222 may comprise hemostasis valves. The fluid ports 222 may be configured to couple to luer-type connectors. One of the fluid ports 222 may be configured to be in fluid communication with the one or more vacuum lumens 114. One of the fluid ports 222 may be configured to be in fluid communication with the one or more irrigation lumens 134. The proximal end 138 of the irrigation tube 130 may be positioned distally of the proximal end 118 of the vacuum tube 110 within the handle 202. The handle 202 may include a shell or casing 224. The shell or casing 224 may include a grip for grasping by the user. The handle 202 may include a strain relief 226 for facilitating transfer of forces from the handle 202 to the catheter 102. The strain relief 226 may extend partially into the shell or casing 224. The strain relief 226 may tightly fit around an outer diameter of the catheter 102 along a portion of the length of the catheter 102. In some implementations, the catheter 102 may be axially translated in a proximal or distal direction by translating the handle 202 in a corresponding axial direction. In some implementations, the catheter 102 may be rotated by rotating the handle 202. In some embodiments, the fluid port 222 into the vacuum lumen within the handle is positioned on the proximal end of the handle 202 and the fluid port 222 into the irrigation lumen within the handle is position on the Y-branch of the handle. In some embodiments, the vacuum lumen within the handle extends substantially straight from a distal portion of the handle 202 to the proximal end of the handle 202, for example from the coupling to the catheter vacuum tube 110 to the proximal end of the handle. In some embodiments, the inner diameter of the vacuum lumen within the handle tapers from proximal to distal, such that the inner diameter at the proximal end fluid port 222 is greater than the inner diameter at the coupling to the catheter vacuum tube 110.

Figure 9:
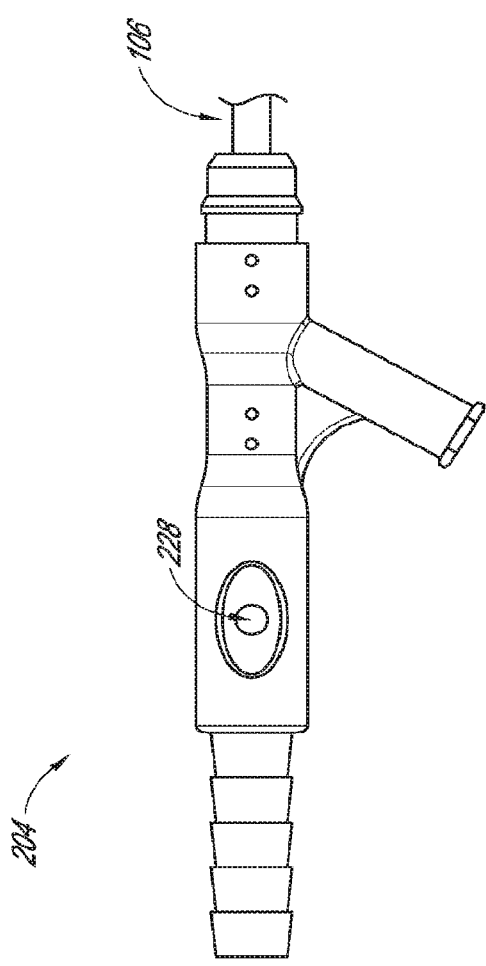
FIG. 9 schematically depicts a side view of another example of a device handle comprising a finger port.

FIG. 9 schematically illustrates a side view of another example of a handle 204. The handle 204 may include the same or similar features as other handles described elsewhere herein. In some embodiments, the handle 204 may comprise a side opening or finger port 228. The finger port 228 may be in fluid communication with the vacuum tube 110. The finger port 228 may be positioned anywhere along the length of the handle. For example, the finger port 228 may be positioned 1 cm, 5 cm, 10 cm, 15 cm, 20 cm, 25 cm, 30 cm, 40 cm, 50 cm, more than 50 cm from either the proximal or distal end of the handle 204. In some embodiments, the finger port 228 may be positioned/formed on the catheter 102 (within the sidewall 112). In some embodiments, the finger port may be positioned/formed on a suction line connected to the outlet of the handle 204 (e.g., connected to a proximal end of the handle). In some embodiments, the finger port 228 may be positioned on a lever or knob for manipulating a pull wire, as described elsewhere herein. The lever or knob may comprise an internal passage joining the vacuum lumen 114 and finger port 228 in fluid communication. When not occluded (e.g., by a finger), the finger port 228 may also be in fluid communication with the ambient atmosphere such that any suction generated by the negative pressure source does not provide a significant suction force at the distal end of the vacuum tube 110. The finger port 228 may advantageously provide fluid communication between the kidney or other physiological area of interest via one or more aspiration ports 116 and the ambient atmosphere. Doing so may effectively prevent over-pressurization of the kidney, even when irrigation is applied. The finger port 228 may act as a pressure release valve, which may release pressure from the kidney or equilibrate pressure within the kidney. For example, excess irrigation fluid may flow down the aspiration lumen 114 and exit via the finger port 228 even absent the negative pressure of suction. Thus, in some embodiments, pressure between the inside of the kidney and the ambient atmosphere may be equilibrated during a non-suctioning period during which no suction is provided through the one or more aspiration ports 116 in fluid communication with the finger port. In embodiments comprising multiple aspiration ports 116, some or all of the aspiration ports 116 may be in fluid communication with the finger port 228. In some embodiments comprising multiple aspiration ports 116, the aspiration ports 116 may be in fluid communication with multiple finger ports 228. When a user wishes to provide suction through the catheter 102, the user may place a finger over the finger port 228, occluding the negative pressure source's fluid coupling with the ambient atmosphere and causing a suction force to be generated at the distal end of the vacuum tube 110. Removal of the user's finger may cause suction to cease again. The finger port 228 may advantageously allow the user to quickly stop and start suction with a single finger on-demand (e.g., instantaneously or virtually instantaneously), without having to let go of or rearrange his or her grip on the handle 204.

In some embodiments, a finger port 228 may similarly be used for providing on-demand control over irrigation. In some embodiments, a single finger port 228 may provide control over both suction and irrigation. For example, in one embodiment, occluding the finger port 228 may begin suctioning and temporarily stop an otherwise continuous irrigation or vice-versa. In another embodiment, occluding the finger port 228 may instantaneously begin suctioning and irrigation. A mechanical and/or hydrodynamic coupling between the vacuum tube and/or a fluid port 222 in communication with the vacuum tube 110 and the irrigation tube 130 and/or a fluid port 222 in communication with the irrigation tube 130 may be used to synchronize the suction and irrigation in an appropriate manner. For example, in one embodiment the suction provided by the negative pressure source when the finger port 228 is occluded may collapse a collapsible portion of the irrigation tube 130 or a collapsible segment of a fluid port 222 proximal to the irrigation tube 130, thereby preventing the transfer of irrigation fluid to a distal end of the catheter 102. In another embodiment, the suction provided by the negative pressure source when the finger port 228 is occluded may force open a valve (e.g., a one-way valve) which is blocking the flow of irrigation fluid. In some embodiments, the finger port may comprise a pressable button. The pressable button may allow air flow through the finger port 228 and prevent suction when left unpressed and may either occlude (e.g., pinch) the irrigation passage when pressed or cause a valve to open within the irrigation passage when pressed. Other various mechanical arrangements are possible to suit any desired configuration of control over aspiration and irrigation. In some implementations, actuation of the finger port 228 or other control may not start and stop suction and/or irrigation but may modulate the level of suction and/or irrigation. For instance, a basal level of suction and/or irrigation may be provided and the level may be transiently increased (e.g., pulsed) or transiently decreased (e.g., dampened) by actuation of the finger port 228.

In some embodiments, a portion of the length of the catheter 102, such as a distal portion, may be steerable or articulable. Specifically, the curvature of one or more portions of the steerable length may be controllable such that a user is able to control, at least to an extent, the shape or curvature of the steerable portion as it extends from the handle 200 or a non-steerable portion of the catheter 102. By adjusting the curvature of a distal portion of the catheter 102, a user may effectively move the distal tip of the catheter 102 with some precision through a prescribed volume of space without repositioning the proximal portion of the catheter 102. In some embodiments, the vacuum tube 110 is configured to be steerable. Steering the vacuum tube 110 may simultaneously steer or control the configuration of portions of any irrigation tubes 130 or surrounding sheaths that are coupled to the vacuum tube 110 and overlap the length of the steerable portion of the vacuum tube 110. In other embodiments, an irrigation tube 130 or both the vacuum tube 110 and an irrigation tube 130 may be steerable. In various embodiments, steerable portion of the catheter 102 is steerable at angles greater than about 90 degrees, greater than about 100 degrees, greater than about 110 degrees, greater than about 120 degrees, greater than about 130 degrees, greater than about 140 degrees, greater than about 150 degrees, greater than about 160 degrees, greater than about 170 degrees, or greater than about 180 degrees. In some embodiments, the steerable portion of the catheter is steerable at angles up to about 90 degrees, up to about 100 degrees, up to about 110 degrees, up to about 120 degrees, up to about 130 degrees, up to about 140 degrees, up to about 150 degrees, up to about 160 degrees, up to about 170 degrees, or up to about 180 degrees.

Figure 10A:
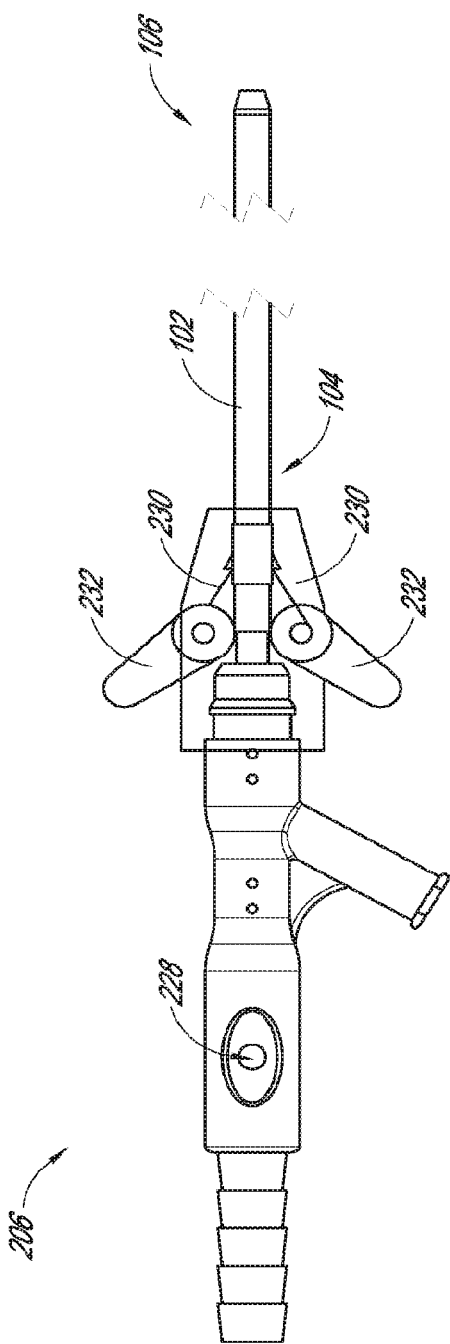

FIGS. 10A-10B schematically illustrate examples of components that may be used for steering the catheter 102. FIG. 10A depicts a handle 206 connected to the catheter 102 including two levers 232, each of which is configured to control a pull wire 230 attached to the steerable portion of the catheter 102. FIG. 10B depicts an example of a pull wire ring 234 which may be attached to an outer circumference of the catheter 102 and is configured to introduce the pull wires 230 extending from the levers to the catheter 102.

One or more pull wires 230 may be used to control the steering or articulation of the steerable portion of the catheter 102. In some embodiments, the pull wires 230 may be about 0.001 inch to about 0.005 inch. In some embodiments, the pull wires 230 may be about 0.001 inch to about 0.01 inch. For example, the pull wires 230 may be about 0.006 inches. The pull wires may comprise stainless steel. In some embodiments, the pull wires 230 may have a circular cross-section. In some embodiments, the pull wires 230 may have an oblong cross section (e.g., about 0.001 inch by 0.005 inch). A pull wire 230 may be rigidly attached at one or more points along a section of the catheter 102 in which the pull wire 230 is configured to articulate. Proximal to the attachment point or points the pull wire 230 may be coupled to the catheter 102 in a non-fixed manner such that the pull wire 230 is able to glide or otherwise advance proximally and/or distally over the length of the catheter 102. In some embodiments, the pull wires 230 may be encased in an outer liner 111 (see FIG. 7B), such as a polytetrafluoroethylene (PTFE) tube. The PTFE tubes may comprise a wall thickness of about 0.001 to about 0.002 inches, in some embodiments. The outer liner 111 may improve the gliding of the pull wire 230 along the adjacent length of the catheter 102. In some embodiments, the pull wires 230 may extend along the outside of the vacuum tube 110. In some embodiments, the pull wires 230 may extend along an inside of the vacuum tube 110 (e.g., along a surface of the vacuum lumen 114). In some embodiments, the pull wires 230 may extend within the sidewall 112 of the vacuum tube 110. For instance, the pull wires 230 may extend in the space between an inner layer and an outer layer of the vacuum tube 110, such as either inside of or outside of the braid or coil or within the braid or coil (e.g., triaxially within the braid). In embodiments using outer liner 111, the liner 11 may extend in the space between an inner layer and an outer layer of the vacuum tube 111. In some embodiments, the pull wires 230 may extend all the way to the distal end of the catheter 102 and/or to the distal end of the steerable portion of the catheter 102. The pull wire 230 may be fixedly attached to the catheter 102 at the distal end of the pull wire 230 or at one or more points proximal to the distal end of the pull wire 230. The pull wires 230 may be coupled at a distal end to a pull ring formed in the sidewall 112 or coupled to the sidewall 112. The pull ring may comprise stainless steel. In some embodiments, the pull ring may be positioned back from the distal edge of the catheter 102. For example, the pull ring may be about 0.5 mm, 1 mm, 1.5 mm, 2 mm, 2.5 mm, 3 mm, 3.5 mm, 4 mm, 4.5 mm, 5 mm, less than 0.5 mm, more than 5 mm from the distal end of the catheter 102, or some value in a range defined there between.

Placing tension on a pull wire 230 may cause the length of the pull wire 230 aligned along the catheter 102 to shorten and may thereby cause the catheter 102 to bend along the side of the catheter 102 to which the pull wire 230 is attached. The catheter 102 may bend along a portion of the length or the entire length proximal to the attachment point of the pull wire 230 (the steerable portion). The flexibility and/or gradient of flexibility of the catheter 102 along the steerable portion may determine the amount of curvature experienced along a particular length of the catheter 102 for a given amount of tension/contraction. In some embodiments, more than one pull wire 230 may be positioned along the same side and may be fixedly attached to the catheter 102 at different axial points. Multiple pull wires 230 positioned along a single side may fine-tune the curvature of bending. In some embodiments, multiple pull wires 230 may be positioned on different sides of the catheter 102 (e.g., two pull wires positioned approximately 180 degrees from each other relative to the circumference of the catheter). In embodiments comprising multiple pull wires 230 on different sides of the catheter 102, the attachment points may be positioned at same axial length along the longitudinal axis of the catheter 102 and/or may be positioned at different axial lengths along the longitudinal axis of the catheter 102.

As shown in FIG. 10A, each pull wire 230 may diverge at an angle from the catheter 102 at a proximal end 104 or proximal portion of the catheter 102 configured to be positioned outside of the body (e.g., near or at the handle 206) and may be joined to a lever 232 or other control. The lever 232 may be pivotably joined to the handle 206 or to an attachment coupled to the handle 206 or to a proximal end 104 of the catheter 102. The pull wire 230 may be joined to the lever 232 a distance away from the pivot point 238 such that the lever 232 acts as a fulcrum. Adjusting the orientation of the lever 232 around the pivot point 238 may modulate the length of the pull wire 230 that diverges from the catheter 102 and correspondingly the length of the pull wire 230 aligned along the catheter 102 to run parallel to the catheter 102, as the total length of the pull wire 230 will remain constant. For example, by pulling the lever 232 in a proximal direction, the length of the pull wire 230 that extends from the catheter 102 to the lever 232 may be increased, thereby decreasing the length of the pull wire 230 that runs parallel to the catheter 102. By shortening the length of the pull wire 230 that runs parallel to the catheter 102, the pull wire 230 may cause the catheter 102 to effectively shorten its length along the side, which the pull wire 230 extends by bending the catheter 102 to curve inward along the length of the pull wire 230. One or more levers 232 may be connected to the handle 206. Each lever 232 may effectively control the length of one or more pull wires 230. Any suitable mechanism may be used for modulating the effective length of the pull wire 230 along the catheter 102. For example, in some embodiments, the proximal end of the pull wire 230 may be attached to a sliding mechanism that slides, or is otherwise axially translatable, along an axial length of the handle 206 and/or catheter 102. In some embodiments, as illustrated in FIG. 10A, the control feature on the handle 206 used to control the pull wires 230 (e.g., the levers 232) may actuate within a plane that is parallel to the longitudinal axis of the handle 206. For example, as illustrated, the levers 232 pivot within a plane that is parallel to the longitudinal axis of the handle 206.

A pull wire 230 may extend from a lever 232 or other control and be coupled to the length of the catheter 102 via a component such as the pull wire ring 234 depicted in FIG. 10B, or a similar mechanism. The pull wire ring 234 may be a ring configured to be secured to the outer circumference of a proximal portion of the catheter 102 configured to be positioned outside of the body. The pull wire ring 234 may include one or more apertures 235 for introducing one or more pull wires 230 to the catheter 102. An aperture 235 may position a distal portion of the pull wire 230 adjacent the catheter 102 so that the distal portion runs parallel to the catheter 102, such as by creating an access point where the pull wire meets, enters, and/or passes through the catheter 102. As described elsewhere herein, the pull wire 230 may run inside of the catheter 102, outside of the catheter 102, or internally within a sidewall 112 of the catheter 102 (e.g., the sidewall of the vacuum tube 110). Portions of the catheter 102 may comprise one or more guides (e.g., rings, loops, notches, etc.) or other structures which allow axial motion to the pull wire 230 relative to the catheter 102 but confine the pull wire 230 to remain parallel to the catheter 102 along a distal length. The one or more apertures 235 may form guide paths which define angles at which the pull wires 230 diverge away from the catheter 102, for at least a portion of its length, as the pull wires 230 extend from the catheter 102 to the lever 232 or other control mechanism.

Figure 11A:
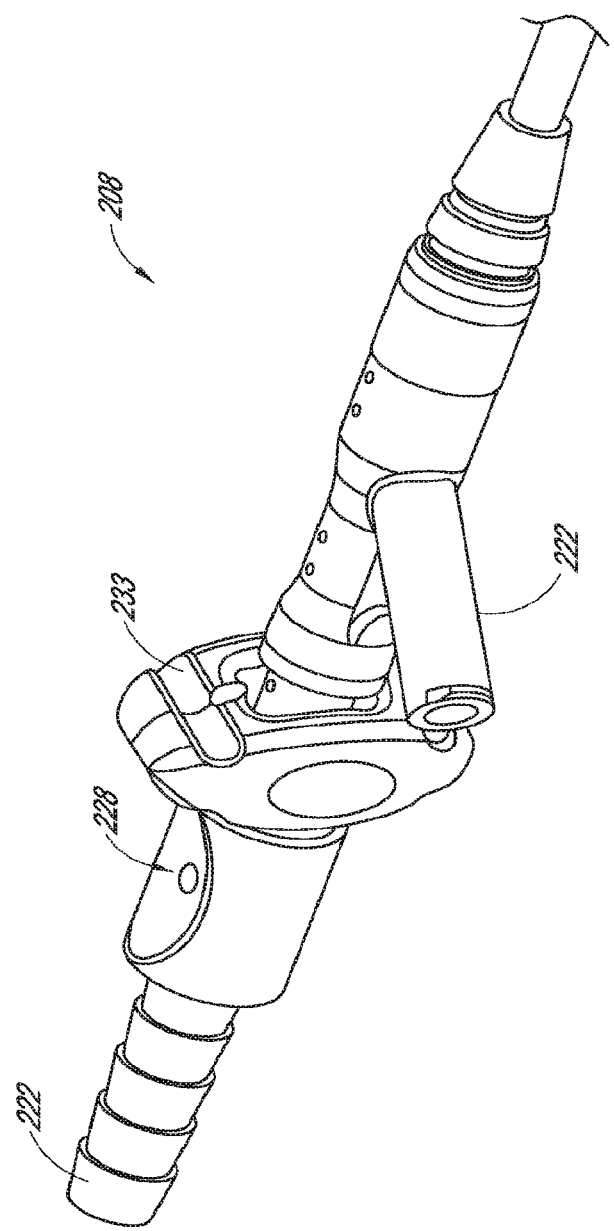

FIGS. 11A-11F schematically illustrate another example of a handle 208 configured to manipulate pull wires 230. The handle 208 may include the same or similar features as other handles described elsewhere herein. FIG. 11A depicts a perspective view of the handle 208. FIG. 11B depicts a top view of the handle 208. FIG. 11C depicts a top view of a cross section of the handle 208. FIG. 11D depicts a side view of the handle 208. The handle 208 may include a lever 233 for pulling or otherwise manipulating one or more pull wires 230. FIG. 11E depicts a front view of the lever 233. The lever 233 may comprise two halves configured to be fixedly joined together around a circumference of portion of a shaft of the handle 208. The lever 233 may be pivotably joined to the handle shaft and create a fulcrum for modulating the length of the pull wire 230 along the catheter 102, as described elsewhere herein. In some embodiments, the lever 233 may extend in one direction from the pivot point 238, similar to the embodiment illustrated in FIG. 10A. In some embodiments, the lever 233 pivots within a plane that is parallel to the longitudinal axis of the handle 208.

In some embodiments, as illustrated in FIGS. 11A-11F, the lever 233 may include two interconnected lever arms 233a, 233b positioned on opposite sides of the lever 233 (approximately 180 degrees from each other around the circumference of the shaft) for controlling two pull wires 230. The pull wires 230 may extend along substantially opposite sides of the catheter 102 (approximately 180 degrees from each other). The lever 233 may include proximal attachment points 236 (e.g., channels, or apertures) for attaching to the pull wires 230. The pull wires 230 may be fixedly secured to the proximal attachment points 236 by any suitable means. In some embodiments, rotation of the lever 233 around the pivot point 238 causes retraction of the pull wire 230 on one side of the catheter 102 and allows extension of the pull wire 230 on the opposite side of the lever 233, in some proportionate manner. The two pull wires 230 may be attached to the lever 233 at the same or at different distances from the pivot point 238. The distal ends of the two pull wires 230 may be fixed to the catheter 102 at the same or at different axial points of the catheter 102. In some embodiments, rotating the lever 233 in one direction (e.g., clockwise) may cause a steerable portion of the catheter 102 to bend in a first direction, while rotating the lever 233 in the opposite direction (e.g., counterclockwise) may cause a steerable portion of the catheter 102 to bend in a second direction, substantially opposite the first direction. Other arrangements of levers 233, including levers 233 attached to more than two pull wires 230, are also possible.

As shown in FIG. 11C, the handle shaft may include one or more apertures 235 for receiving a pull wire 230. The aperture 235 may position the pull wire 230 proximal to the catheter 102 (e.g., the vacuum tube 110) and the pull wire 230 may be introduced to the catheter 102 at a proximal end 104 of the catheter 102. The aperture 235 may introduce the pull wire 230 along a proximal portion of the catheter 102. In some embodiments, the catheter 102 may include an aperture through its sidewall 112 for allowing a pull wire 230 to extend into or through the sidewall of the catheter 102. In some embodiments, as seen in FIG. 11C, one or more of the fluid ports 222 of the handle 208 may vary in diameter (e.g., decrease) as the fluid port 222 lumen extends inward toward the catheter 102. The lumens may comprise step changes 223 in diameter, which may be configured to abut and properly seat a proximal end of the catheter 102 or one of the catheter 102 components (e.g., a vacuum tube 110 or irrigation tube 130). In some embodiments, the variable diameter of the fluid passage may facilitate forming a fluid-tight seal with an inserted hose (e.g., a suction tube).

Figure 11F:
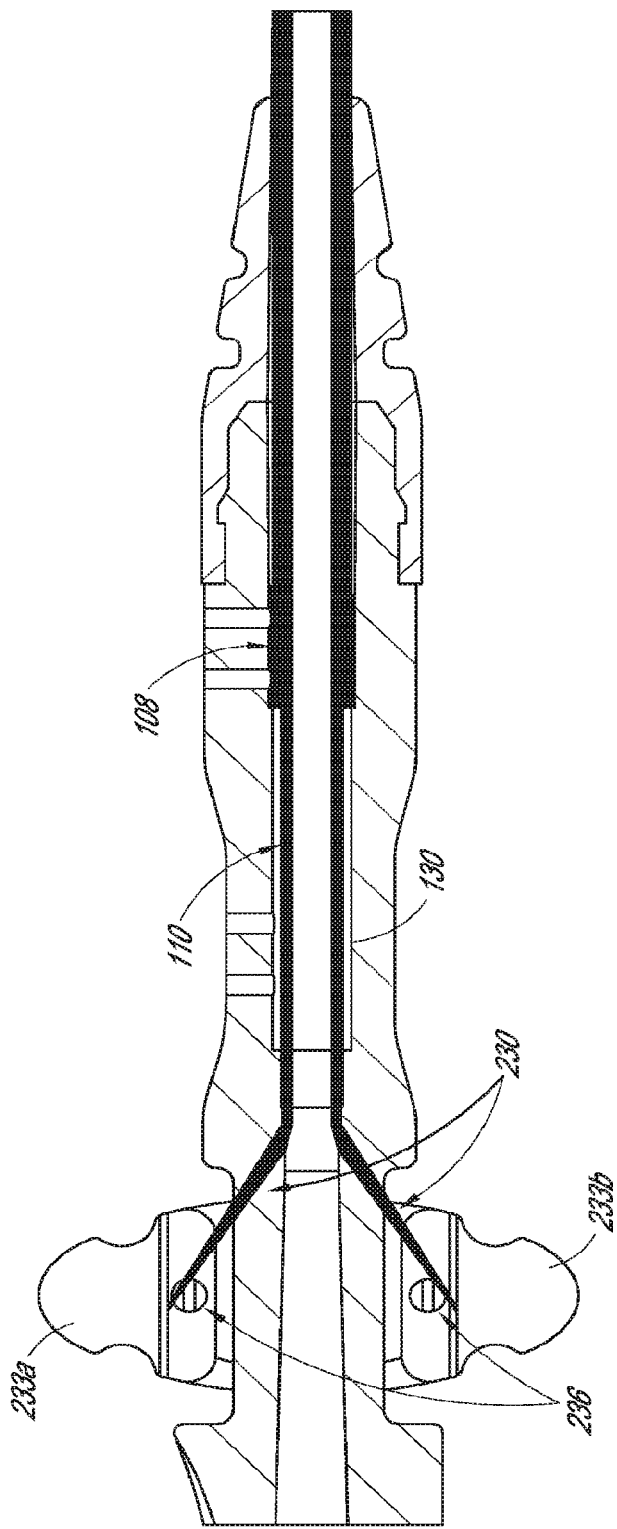

FIG. 11F schematically illustrates an example of a cross section of a portion of a handle 208 comprising two pull wires 230 coupled via support pins at proximal attachment points 236 to interconnected lever arms 233a, 233b. The pull wires may extend over, under, or into the vacuum tube 110, as described elsewhere herein. FIG. 11F illustrates an example of a proximal end 104 of a catheter 102 as configured in FIGS. 3A-3B. The vacuum tube 110 may be coupled to the irrigation tube 130 by an adhesive (e.g., a UV curable adhesive) applied between the outer circumference of the vacuum tube 110 and the inner circumference of the irrigation tube.

Figure 21A:
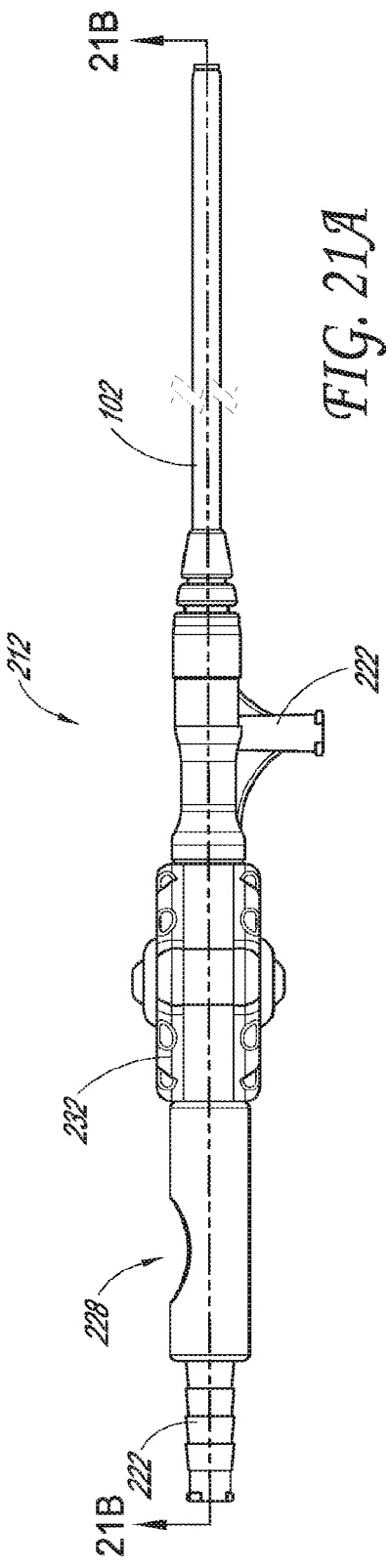
FIGS. 21A and 21B schematically depict another example of a removal device handle.
Figure 21B:
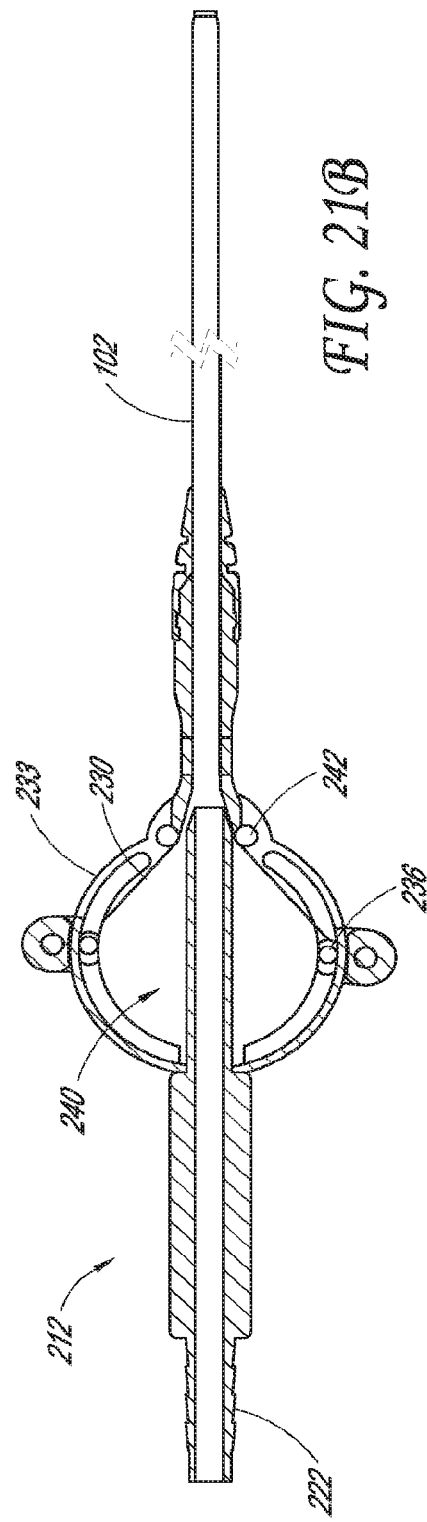

FIGS. 21A and 21B schematically illustrate another example of a handle 212. FIG. 21A illustrates a side view of the handle 212 and FIG. 21B illustrates section A-A of handle 212 depicted in FIG. 21A. The handle 212 may comprise the same or similar features as other handles described elsewhere herein, particularly handle 208. The handle 212 may comprise a lever 232 which comprises a generally circularly configuration. The lever 232 may be centered so that a pivot point of the lever 232 is positioned along a longitudinal axis of the handle 212 and/or catheter 102. The lever 232 may be actuatable from either of two opposite sides, similar to the lever 232 of handle 208. Pull wires 230 may be coupled to proximal attachment points 236 (e.g., pins), as described elsewhere herein, which may be rotatable generally around a circumference of the circular lever 232. The lever 232 may comprise a void space 240 through which the pull wires extend from the catheter 102 to the proximal attachment points 236. The lever 232 may form a casing which surrounds and encloses the pull wires 230. The casing may protect the pull wires 230 from the external environment. The lever 323 may comprise spacing elements such as rods 242, each of which may be configured to reorient a pull wire 230 between the catheter 102 and the pull wire's proximal attachment point 236. The one or more spacing elements may prevent or inhibit the pull wire 230 from contacting (e.g., rubbing against) surfaces or edges of the lever 232 between the catheter 102 and the proximal attachment point 236 which may advantageously prevent damage to the pull wire 232. The spacing elements may comprise smooth round surfaces, at least where the spacing elements contact a pull wire 230, in order to promote efficient translation of the pull wire 232 over the surface of the spacing element when the lever 232 is actuated. In some embodiments, the lever 230 may comprise a central fulcrum or spacing element across which one or more pull wires 230 may be translated (e.g., slide). For instance, the lever 232 may comprise a cylindrical shaped spacing element located around the pivot point of the lever. In some embodiments, the spacing element may only correspond to a sector of a cylinder. In some implementations, the spacing element may extend the distance of the pull wire 230 path between the catheter 102 and the proximal attachment point 236. In some embodiments, one pull wire may extend around the central spacing element to the opposite side of the lever 232. The two pull wires 230 may accordingly be coupled to the same proximal attachment point 236 (one approaching from a distal side and one approaching from a proximal side) which may simply the manufacturing of the lever 232.

In some embodiments, the lever 233 may comprise only one lever arm 233a extending from only one side of the handle. The finger port 228 may be positioned opposite the lever arm 233a on the opposite side of the handle at approximately the same length along the longitudinal axis of the handle. Such a configuration may conveniently allow for a user to operate both the pull wires 230 and suctioning (and/or irrigation) via the finger port 228 with a single hand. In some implementations, the lever 233 may be laterally offset from the central longitudinal axis of the handle, such that the pull wire 230 that runs on the opposite side of the lever 233a may attach to the an attachment point 236 without interfering with or obstructing the user's access to the finger port 228.

FIG. 12 schematically illustrates another example of a handle 210. The handle 210 may include the same or similar features as other handles described elsewhere herein. In some embodiments, the handle 210 may be configured with more than two fluid ports 222 (e.g., three ports, four ports, five ports, etc.). FIG. 12 depicts a handle 210 comprising three fluid ports 222. Each fluid port 222 may be in fluid communication with a different lumen of the catheter 102 (e.g., the vacuum lumen 114 and two different irrigation lumens 134). In some embodiments, different fluid ports 222 may be configured for introducing different ancillary devices, such as an introducer, a guidewire, and/or a visualization device.

In some embodiments, the irrigation lumen 134 or lumens may be configured to define an irrigation stream or streams of a specific size, shape, fluid velocity, and/or direction. The number, size, shape, and/or arrangement of irrigation lumens 134, for example, may influence the irrigation stream. The size, shape, velocity, and/or direction of the irrigation stream with respect to the one or more aspiration ports 116 may be used to optimize the capture and removal of kidney stones or other debris. The shape and direction of an irrigation stream provided by an irrigation lumen 134 may be influenced or altered by a nozzle.

Figures 13A, 13B, 13C:
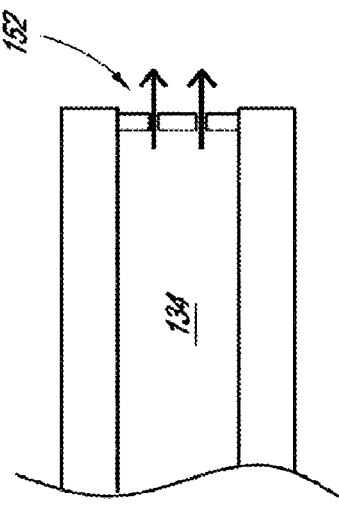
FIGS. 13A-13W schematically depicts cross sections and distal end views of irrigation lumens and catheters comprising irrigation lumens, which may include nozzles for altering irrigation streams.
Figure 13E:
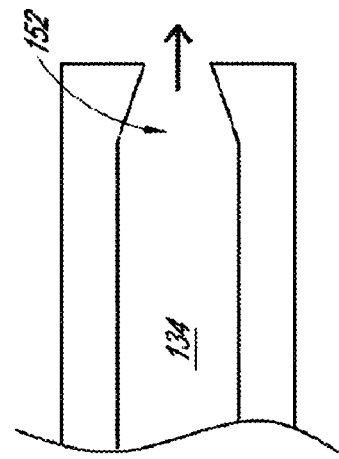
Figure 13D:
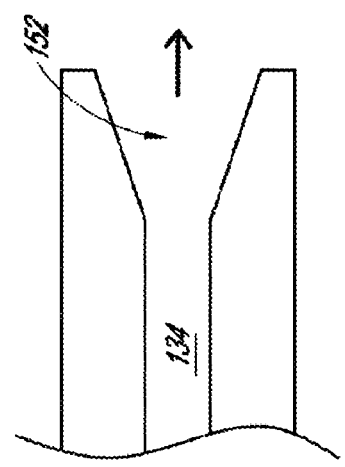
Figures 13F, 13G:
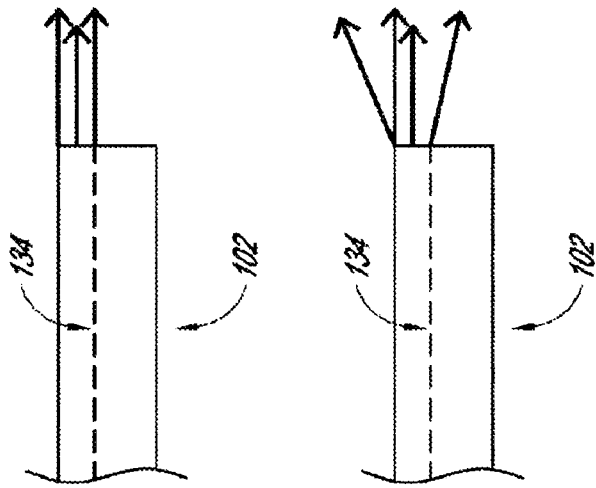
Figure 13J:
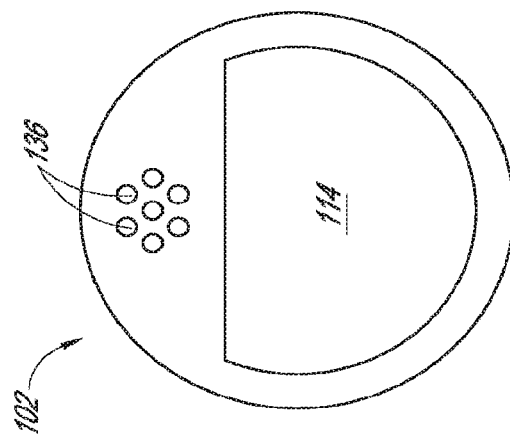
Figure 13M:
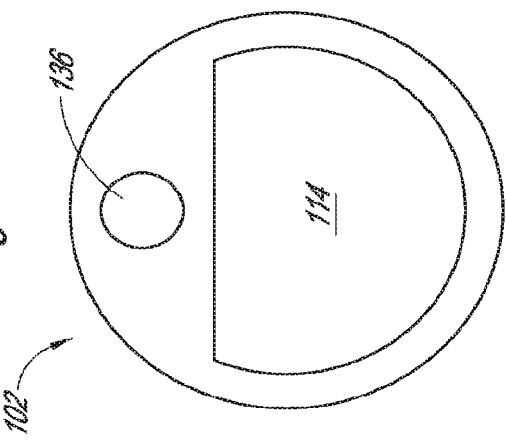
Figure 13I:
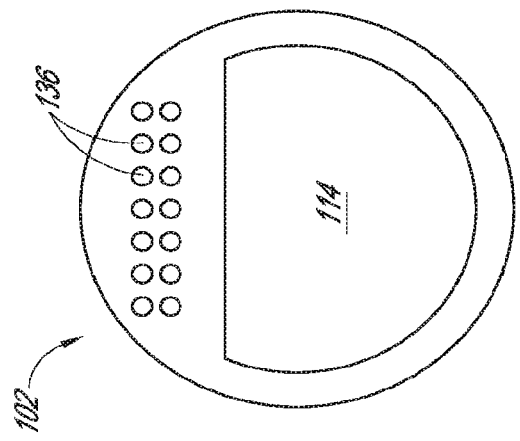
Figure 13L:
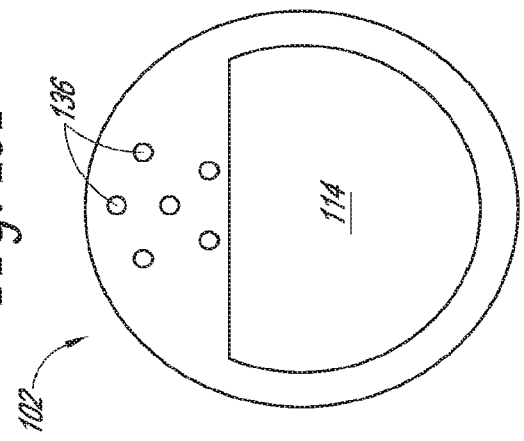
Figure 13H:
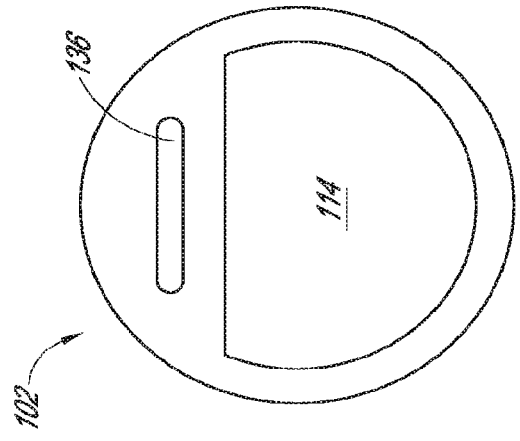
Figure 13K:
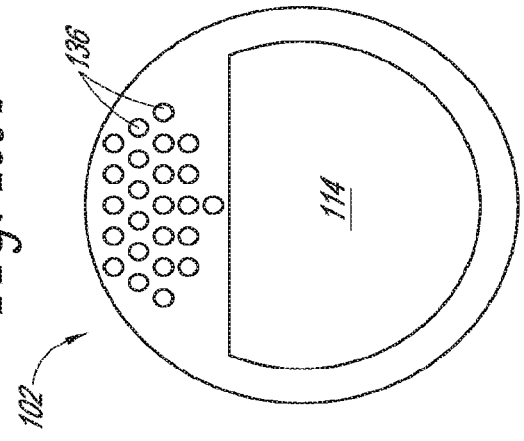
Figure 13W:
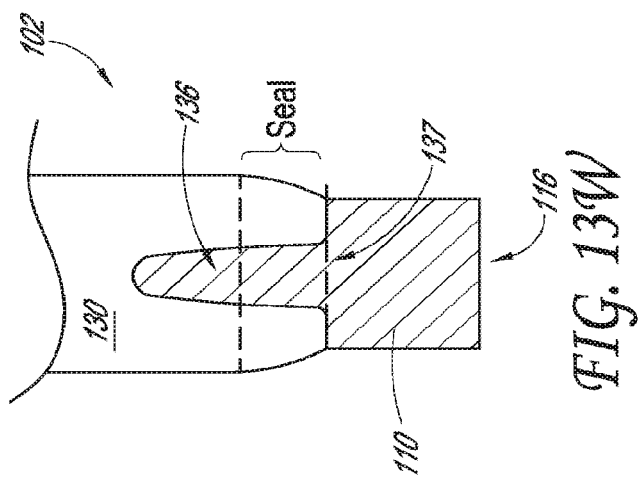
Figure 13V:
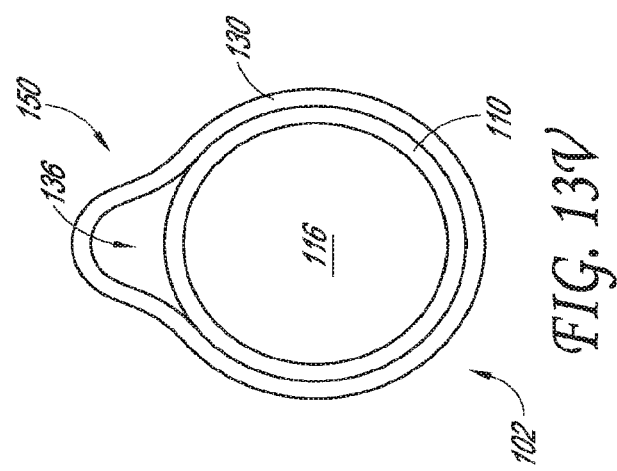
Figure 13N:
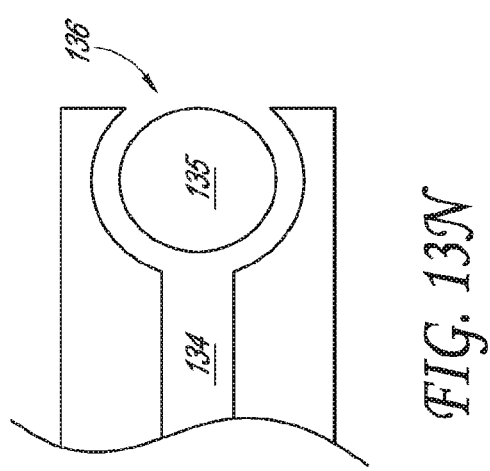
Figure 13O:
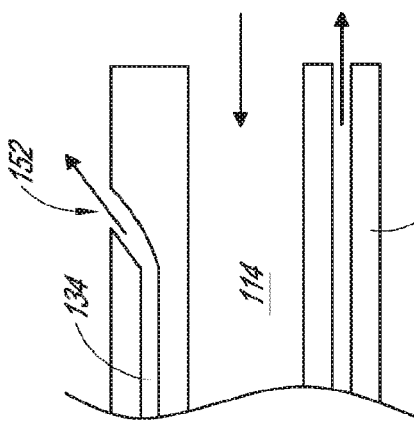
Figure 13P:
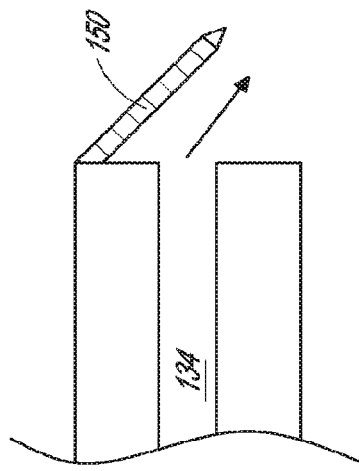
Figure 13Q:
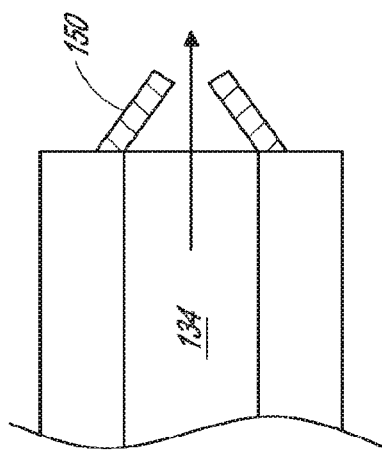
Figure 13R:
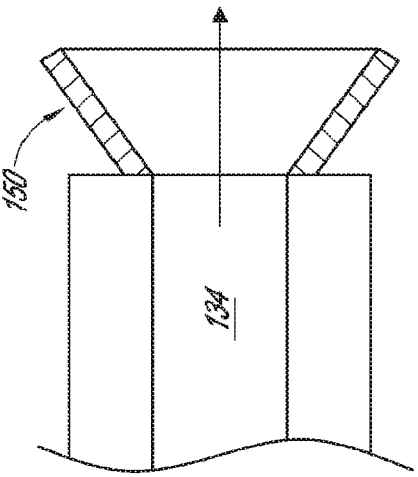
Figure 13S:
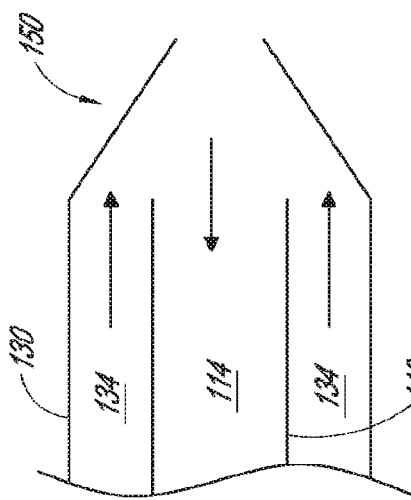
Figure 13T:
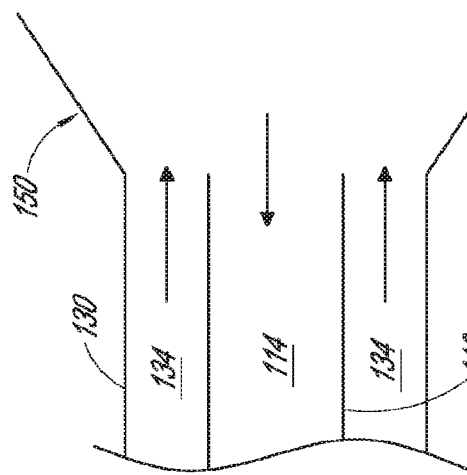
Figure 13U:
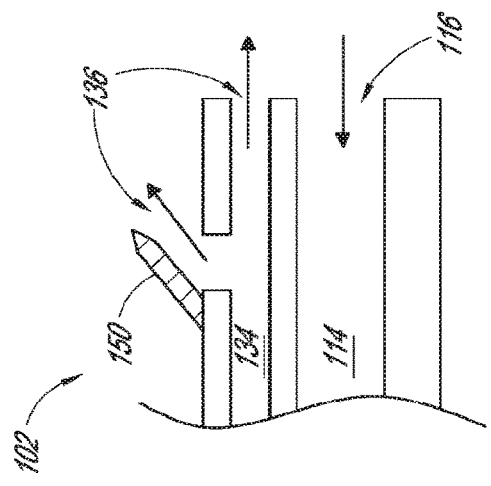

FIGS. 13A-13U schematically illustrate various examples of irrigation lumens and/or irrigation nozzles. An irrigation nozzle may be built-in to the irrigation lumen 134 such that it is formed by a distal end of the irrigation lumen 134 opening into the irrigation port 136. For example, the shape of the distal portion of the irrigation lumen 134 may form a nozzle 152. The irrigation nozzle 152 may, for example, be shaped as a cone having an expanding diameter as the lumen extends to meet the irrigation port 136, as shown in FIG. 13A. An irrigation nozzle 152 with an expanding diameter may increase the spread of the irrigation stream (the angle of the irrigation stream relative to the axis of the irrigation lumen 134) as the irrigation fluid exits the irrigation port 136. The irrigation nozzle 152 may be shaped with a decreasing diameter as the irrigation lumen 134 extends to the irrigation port 136, as shown in FIG. 13B. The irrigation stream may at least partially converge as it exits the irrigation port 136. The irrigation nozzle 152 may be shaped with a constant diameter. The irrigation nozzle 152 may reduce the cross-sectional area of the irrigation port 136 and may create multiple irrigation ports 136. For example, the nozzle may comprise a wall positioned at a distal end of the irrigation lumen 134 having a number of apertures forming a number irrigation ports 136, as shown in FIG. 13C. The irrigation lumen 134 may change directions along a distal portion of the lumen extending to the irrigation port 136. For example, the irrigation lumen 134 may be angled to extend radially outward from the longitudinal axis of the catheter 102, as shown in FIG. 13D. The irrigation lumen 134 may be angled to extend radially inward from the longitudinal axis of the catheter 102, as shown in FIG. 13E. Angling of the irrigation lumen 134 adjacent the irrigation port 136 may alter the direction of the irrigation stream, particularly with respect to the suction stream extending into the aspiration port 116. The irrigation nozzle 152 may be configured to align the irrigation stream substantially parallel to the suction stream, away from the suction stream, or toward the suction stream. The irrigation stream may be configured to extend from the irrigation port 136 as a substantially uniform stream, as depicted in FIG. 13F, experiencing little divergence in the spread or span of the stream directly adjacent to the irrigation port 136. The irrigation stream may be configured to extend as a substantially conical irrigation stream, as depicted in FIG. 13G, experiencing immediate divergence in the spread or span of the stream directly adjacent to the irrigation port 136.

In some embodiments, the irrigation stream may be shaped by the nozzle 152 and/or irrigation port 136. For example, the irrigation stream may be relatively oblong or flat, having a first dimension substantially longer than a second dimension (e.g., a dimension transverse to the first dimension). FIG. 13H depicts the distal face of a catheter 102 comprising an oblong irrigation port 136. The irrigation stream may be fanned (e.g., flat with a divergent dimension). The flat irrigation stream may diverge along the shorter direction, the longer direction, or both. The flat irrigation stream may be oriented in any direction with respect to the catheter 102 (e.g., horizontally, vertically, diagonally, etc.) The irrigation stream may be annular (e.g., ring shaped). The irrigation stream may be emitted in any shape (e.g., circular, triangular square, arced, etc.) and configured to converge, diverge, or extend substantially parallel to the irrigation port 136 as it is emitted from the irrigation lumen 134. FIG. 13I depicts another example of a catheter 102 configured to produce a flat irrigation stream via a plurality of linearly arranged irrigation ports 136. The size of the irrigation port 136 and/or the spacing of a plurality of adjacent irrigation ports 136 may also influence the resulting irrigation stream. In some embodiments, a plurality of adjacent irrigation ports 136 may be formed at the end of one or more irrigation lumens 134, such as by a nozzle 152 (e.g., an irrigation lumen 134 comprising multiple irrigation ports 136). In some embodiments, a plurality of adjacent irrigation ports 136 may be formed from a plurality of adjacent irrigation lumens (e.g., each irrigation port 136 is in fluid connection with a different irrigation lumen 134). For a given applied fluid pressure, the size of the irrigation port 136 (e.g., the cross-sectional area or diameter) may affect the fluid velocity of the irrigation stream as it exits the irrigation port 136. Smaller openings can be used to generate high fluid velocities and larger openings can be used to generate lower fluid velocities. Similarly, the cumulative cross-sectional area of the irrigation ports 136 for a given irrigation lumen 134 may be used to modulate the fluid velocity through the irrigation ports 136. The total number of irrigation ports 136 per irrigation lumen 134 may affect the cumulative cross-sectional area. For example, FIG. 13J depicts a distal face of a catheter 102 comprising a plurality of closely positioned irrigation ports 136, while FIG. 13K depicts a distal face of a catheter 102 comprising a larger plurality of closely positioned irrigation ports spanning a larger area than that of FIG. 13J. In some implementations, the same number of irrigation lumens 134 (e.g., one irrigation lumen) may join the irrigation ports 136 in FIGS. 13J and 13K to pressurized fluid sources. The irrigation stream or streams in FIG. 13J may have higher fluid velocity than the irrigation stream or streams in FIG. 13K. The irrigation stream in FIG. 13J may be more jet-like than the irrigation stream in FIG. 13K, which may be more shower-like.

The arrangement (e.g., proximity) of adjacent irrigation ports 136 may also affect the irrigation stream. FIG. 13L depicts the distal face of a catheter 102 having the same number of similarly sized irrigation ports as in FIG. 13J, but spaced further apart. In some implementations, the irrigation streams from the irrigation ports 136 in FIG. 13J may be more likely to converge into a single jet stream than the further spaced irrigation streams emanating from the irrigation ports 136 in FIG. 13L. FIG. 13M depicts the distal face of a catheter 102 comprising a single irrigation port 136 having a larger cross-sectional area than the irrigation ports 136 depicted in FIGS. 13I-13L. The larger cross-sectional area of the irrigation port 136 may result in an irrigation stream with a heavier flow mass (a higher volumetric flow rate). The heavier flow mass may be particularly advantageous in moving (e.g., dislodging) kidney stones. FIG. 13N depicts an example of a nozzle 152 comprising a rotatable ball 135 positioned within the nozzle 152. The rotatable ball 135 may cause a swirling or vortex effect on the irrigation stream as pressurized irrigation fluid is applied and forced to move across the rotatable ball 135 to reach the irrigation port 136. The fluid velocity may also affect the tendency of the irrigation stream to vortex. In general, larger fluid velocities may more readily create a vortex effect in the irrigation stream. In some embodiments, larger fluid velocities may be promoted by using smaller syringes (e.g., 10 cc). The nozzle may include any other conventional feature, such as those used on garden hoses, for creating a variety of irrigation stream features or patterns. In some embodiments, the diameter of an irrigation port 136 may be about 0.001 inches, 0.025 inches, 0.005 inches, 0.0075 inches, 0.01 inches, 0.02 inches, 0.03 inches, 0.04 inches, 0.05 inches, 0.06 inches, 0.07 inches, 0.08 inches, 0.09 inches, 0.1 inches, less than 0.0001 inches, more than 0.1 inches, or a diameter selected from any range defined there between. In some embodiments, two or more irrigation ports 136 may be spaced apart (e.g., from center-to-center) by about 0.001 inches, 0.025 inches, 0.005 inches, 0.0075 inches, 0.01 inches, 0.02 inches, 0.03 inches, 0.04 inches, 0.05 inches, less than 0.001 inches, more than 0.005 inches, or any length from a range defined there between.

The nozzle 152 may be configured to direct the irrigation stream from a lateral irrigation port 136, such as in a lateral direction, somewhat proximal direction, or somewhat distal direction, as shown in FIG. 13O. In some embodiments, the nozzle may direct the irrigation stream in a lateral direction that is not normal to the surface of the catheter, such as toward a circumferentially adjacent aspiration port 116.

An irrigation nozzle 150 may be formed externally to the irrigation port 136. In some embodiments, the nozzle 150 may be a flange that directs the irrigation flow in a certain direction (e.g., toward or away from the suction stream), as depicted in FIG. 13P. In some embodiments, the nozzle 150 may surround the irrigation port 136 and may comprise a decreasing diameter as it extends distally, as depicted in FIG. 13Q. In some embodiments, the nozzle 150 may surround the irrigation port and may comprise an increasing diameter, as depicted in FIG. 13R. In some embodiments, the nozzle 150 may be formed around the distal end of the catheter 102. For example, as described elsewhere herein, an irrigation tube 130 may extend concentrically around a vacuum tube 110 forming one or more irrigation ports 136 between the outer diameter of the vacuum tube 110 and the inner diameter of the irrigation tube 130, as shown in FIG. 3A and as depicted in FIG. 13S. The portion of the irrigation tube 130 that extends distally of the vacuum tube 110 may form a nozzle 150. The nozzle 150 may alter the shape and/or direction of the irrigation stream or streams provided from the one or more irrigation ports 136. In some embodiments, the nozzle 150 may have an increasing diameter, as depicted in FIG. 13T. In some embodiments, nozzles may be formed adjacent lateral irrigation ports, as depicted in FIG. 13U.

In some embodiments, the irrigation nozzle 150 may be formed from an irrigation tube 130 that is positioned concentrically around a vacuum tube 110, as shown in FIGS. 3A-3B, but in which the distal end of the irrigation tube 130 is positioned proximally behind the distal end of the vacuum tube 110. The inner diameter of irrigation tube 130 may be adhered to the outer diameter of the vacuum tube 110 around a portion of the circumference of the vacuum tube 110 such that the resulting irrigation port 136 formed between the vacuum tube 110 and the irrigation tube 130 is not annular, but only extends around a portion of the circumference of the catheter 102. For instance, a distal portion of the irrigation tube 130 may be heat melted to the vacuum tube 110 forming a fluid seal there between. FIG. 13V schematically illustrates a distal end view of a catheter 102 comprising a vacuum tube 110 and a concentric irrigation tube 130 which is sealed around a portion of its circumference to the vacuum tube 110. The adherence of the irrigation tube 130 to the vacuum tube 110 may form a more continuous taper or smoother transition between the outer diameter of the vacuum tube 110 and the outer diameter of the irrigation tube 130 at the distal end of the catheter 102. The taper may be advantageous for advancing or tracking the catheter 102 through an access sheath, the urethra, ureter, and/or other anatomical lumen and may help prevent the irrigation tube 130 from being forced proximally backward from the distal end of the vacuum tube 110. The seal between the irrigation tube 130 and the vacuum tube 110 may prevent the distal end of the irrigation tube 130 from being displaced relative to the distal end of the vacuum tube 110.

The formation of a fluid seal between the irrigation tube 130 and the vacuum tube 110 around a portion of the circumference of the catheter 102 may form a nozzle 150 which alters the irrigation stream. The irrigation port 136 formed in such an embodiment may be formed over a radial sector of the catheter 102 of approximately 270 degrees, 180 degrees, 90 degrees, 60 degrees, 50 degrees, 40 degrees, 30 degrees, 20 degrees 10 degrees, more than 270 degrees, less than 10 degrees, or some angle defined in a range there between. In some implementations, the sealing of the irrigation tube 130 to the vacuum tube 110 around a portion of the circumference may form a nozzle 150 which alters the irrigation stream. The nozzle 150 may have altered dimensions relative to the remainder of the irrigation tube 110 resulting from the sealing. For example, the nozzle 150 may have a slightly expanded outer diameter resulting from the excess material accumulating along the nozzle 150 when the irrigation tube 130 is drawn radially inward toward the vacuum tube 110 to be sealed. In some embodiments, a lateral hole 137 may be formed along a distal edge of the irrigation tube 110 to help shape the nozzle. The lateral hole 137 may be formed by cutting back a distal edge of the irrigation tube 110. A portion of the edges of the hole may be sealed to the irrigation tube 110 as schematically depicted in FIG. 13W, leaving the remaining portion of the hole to form the irrigation lumen 136. The incorporation of the nozzle 150 from partially sealing the irrigation tube 130 to the vacuum tube 110 may increase the fluid velocity of the irrigation stream for a constant applied volumetric flow rate. The nozzle 150 may result in a more focused, jet-like irrigation stream than the irrigation stream emitted from an unsealed irrigation tube 110. For instance, the irrigation stream may have less of a transverse spread than in an unsealed embodiment. The use of the nozzle 150 as described in relation to FIGS. 13V and 13W may allow more directed irrigation. In some embodiments, the irrigation stream may be directed in a distal direction and, in other embodiments, the irrigation stream may be directed in an off-angled direction. In some implementations, the catheter 102 may be rotated by the user to alter the relative positioning of the irrigation stream relative to the aspiration port 116. A marking, or other fiduciary feature, such as a pull wire lever as described elsewhere herein, may be used to track the circumferential positioning of the irrigation port 136. Rapid rotation of the catheter 102 may create a fluid swirling effect. In some embodiments, the nozzle 150 may create a relatively flatter jet stream. The shape of the lateral hole 137 may be used to alter the resulting irrigation stream.

Figure 5A:
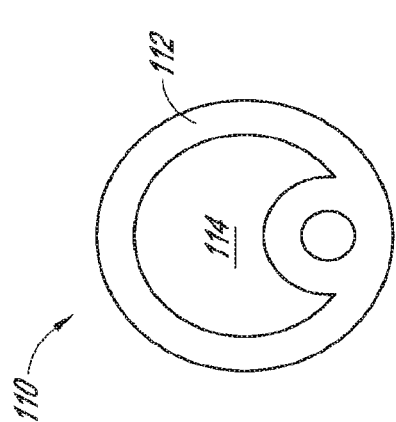
FIGS. 5A-5H schematically depict various cross sections of a multi-lumen vacuum tube in which the various lumens may be used for aspiration, irrigation, and/or delivery of other devices.
Figure 5B:
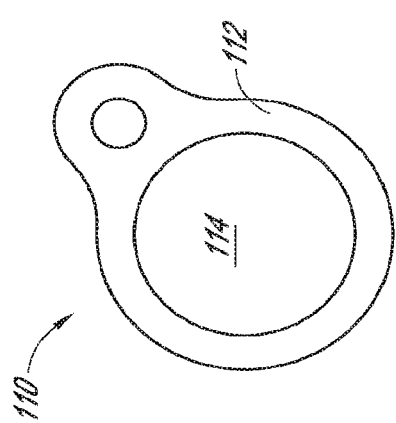
Figure 5C:
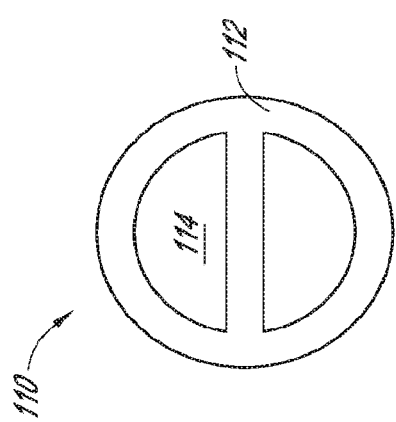
Figure 5D:
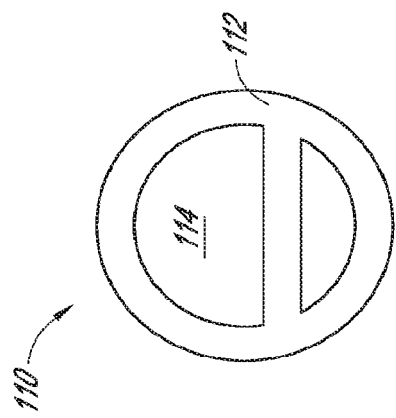
Figure 5E:
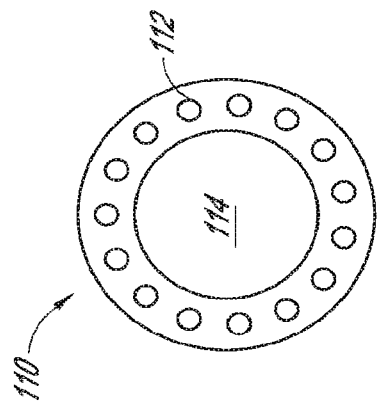
Figure 5F:
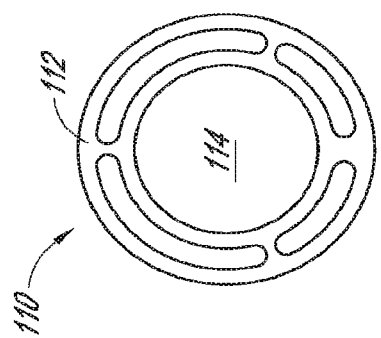
Figure 5G:
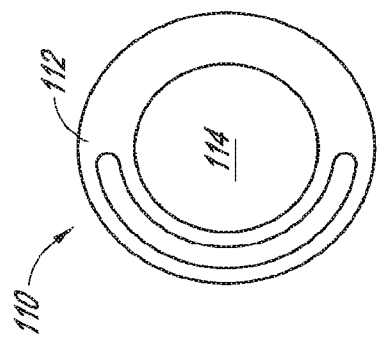
Figure 5H:
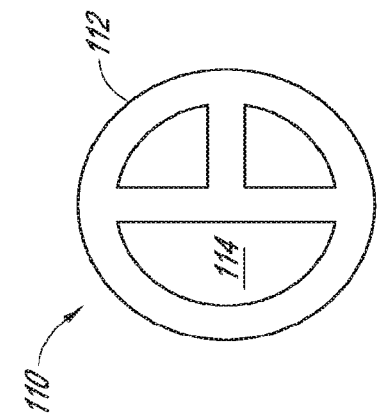
Figure 14A:
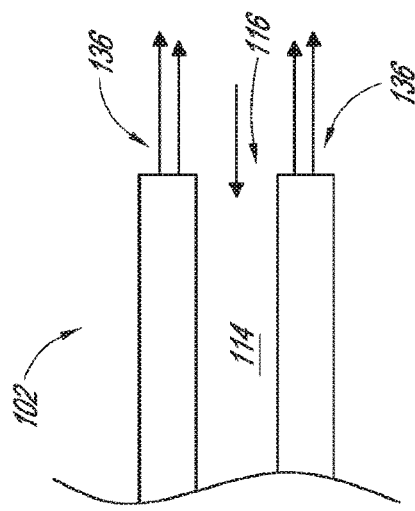
FIGS. 14A-14C schematically depicts various arrangements of irrigation streams relative to the direction of suction at the distal end of a catheter.
Figure 14C:
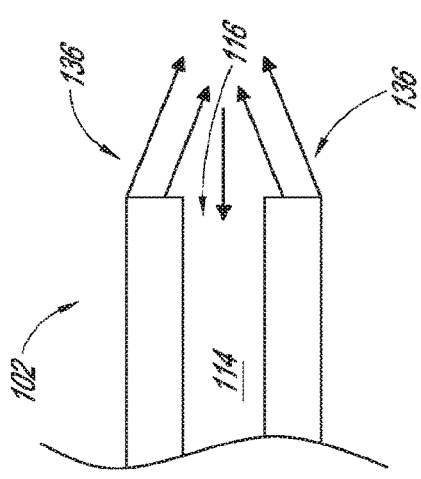
Figure 14B:
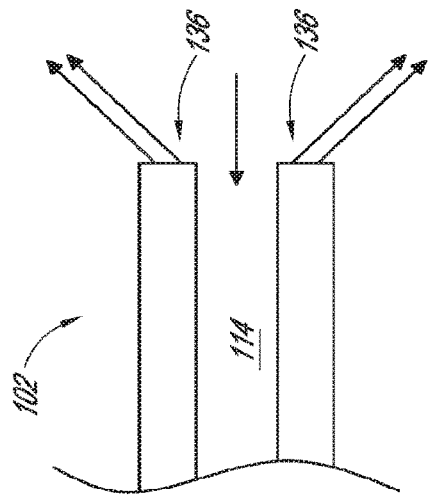

The arrangement of the one or more irrigation streams with respect to the one or more aspiration ports 116 may be configured to optimize removal of kidney stones or other debris. FIGS. 14A-14C schematically depict various examples of the direction of irrigation streams relative to the suction stream. In some embodiments, the one or more irrigation streams may be configured to extend in a direction substantially parallel to the longitudinal axis of the catheter 102. Depending on the positioning of the one or more aspiration ports 116, the irrigation streams may extend in a direction substantially parallel to a suction stream as well, as depicted in FIG. 14A. The irrigation stream or streams may be arranged concentrically surrounding or partially surrounding an aspiration port 116. For example, an irrigation lumen 134 may be formed by an irrigation tube 130 positioned around the outer circumference of a vacuum tube 110, as depicted in FIGS. 3A-3B or one or more irrigation lumens 134 may be formed in a sidewall of the vacuum tube 110, as depicted in FIG. 5E or FIG. 5F. In some embodiments, the one or more irrigation streams may be configured to extend radially outward away from the longitudinal axis of the catheter 102. The irrigation stream or streams may form an irrigation cone surrounding the aspiration port 116, in which irrigation fluid is expelled distally and radially outward around the aspiration port 116, as depicted in FIG. 14B. In some embodiments, the irrigation stream or streams may form an irrigation cone surrounding the aspiration port 116, in which irrigation fluid is expelled distally and radially inward around the aspiration port 116, such that the direction of the irrigation stream or streams intersects the longitudinal axis of the catheter 102, as depicted in FIG. 14C.

Figure 15A:
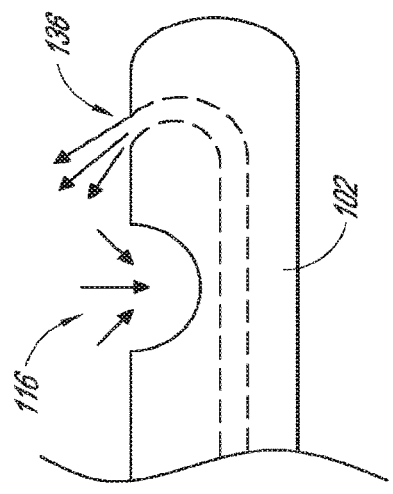
FIGS. 15A-15F schematically depict various examples of configurations of catheters comprising irrigation and aspiration.
Figure 15B:
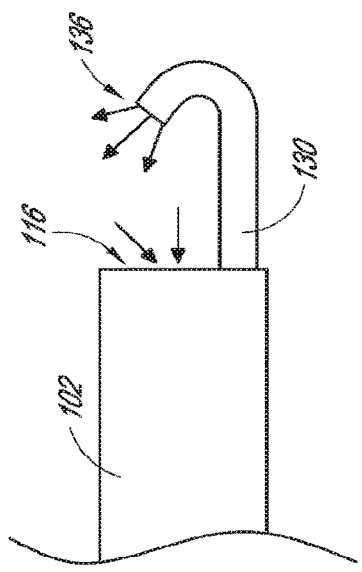
Figure 15C:
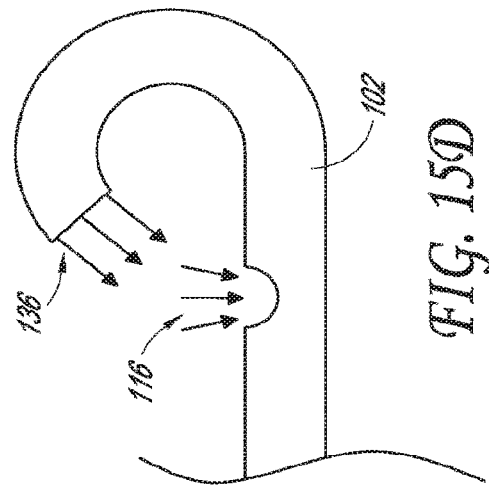
Figure 15D:
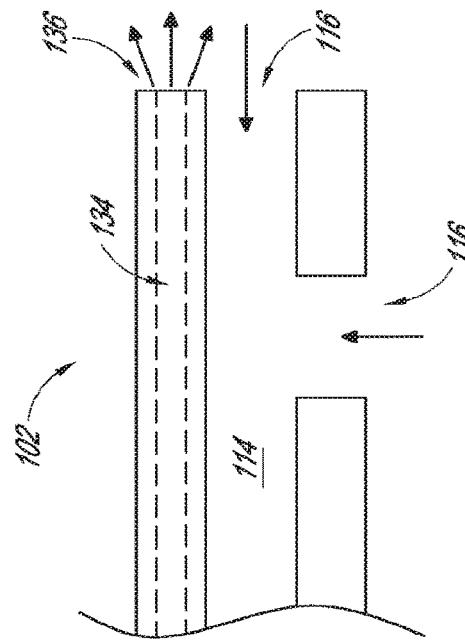
Figure 15E:
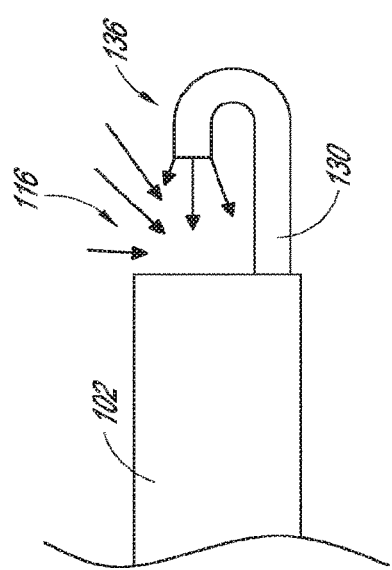
Figure 15F:
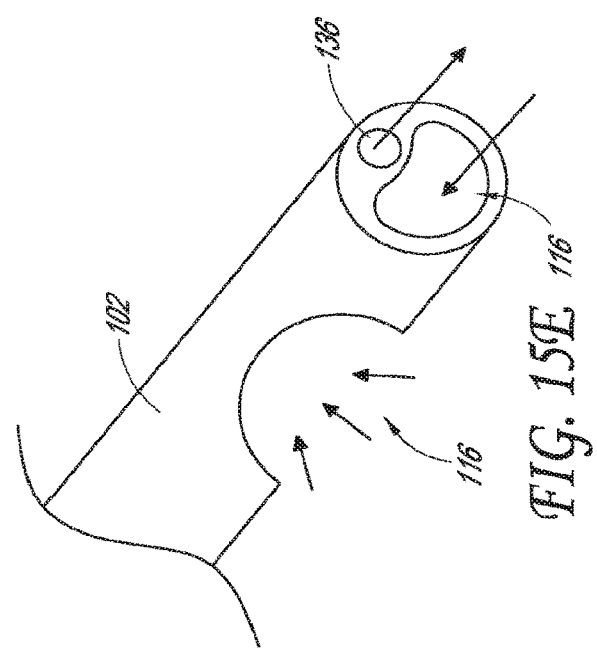

FIGS. 15A-15F schematically illustrate various examples of catheters comprising different arrangements of suction and irrigation. In some embodiments, an irrigation port 136 may be provided along the length of the catheter 102 at a position distally of an aspiration port 116, as shown in FIG. 15A. The irrigation stream may help direct kidney stones toward the aspiration port 116. The aspiration port 116 may be formed in a sidewall of the catheter 102 as a lateral port. In some embodiments, the aspiration port 116 may face a distal direction and the irrigation lumen 134 may extend distally beyond the aspiration port 116, as depicted in FIG. 15B. For example, the irrigation lumen 134 may extend through the aspiration lumen and beyond the aspiration port 116. The irrigation port 136 may face a distal direction (aligned along the longitudinal axis of the catheter 102). A distal portion of the irrigation lumen 134 beyond the aspiration port 116 may be curved such that the irrigation stream is directed in a direction offset from the distal direction. For example, the irrigation stream may be directed along an angle relative to the longitudinal axis less than 45 degrees, 45 degrees, 90 degrees, 135 degrees, 180 degrees, 225 degrees, more than 225 degrees, or any angle in ranges there between. FIG. 15B depicts an irrigation tube 130 bent between 90 degrees and 180 degrees (about 235 degrees) to direct irrigation fluid in a proximal and lateral direction. FIG. 15C depicts an irrigation tube 130 bent 180 degrees to direct irrigation fluid in a proximal direction. In some embodiments, as shown in FIG. 15C, irrigation fluid may be directly straight toward an aspiration port 116. As described elsewhere herein, directing irrigation fluid into or toward an aspiration port can increase the effective pressure difference across the irrigation port 136 and facilitate suctioning of kidney stones or other debris. In some implementations, the irrigation may be optimized such that suctioning can be eliminated or not used altogether, or at least such that the amount of negative pressure applied to the vacuum lumen 114 can be reduced. The curved distal portion of the irrigation lumen 134 may be formed such that the curve is a permanent part of the shape of the catheter 102. In some embodiments, the distal portion may be steerable, as described elsewhere herein, and the curved portion may be implemented by steering the distal end to assume the curved shape described herein. In some embodiments, the distal portion may be steerable and formed such that it is biased to assume the curved shape, such as when no force is applied. The shape of the curve may be altered (e.g., the angle of the distal end relative to the longitudinal axis may be increased or decreased), such as by manipulation of pull wires 230, as described elsewhere herein, or by any other suitable means. For example, the curved distal portion may be straightened or even curved in an opposite direction (e.g., away from the aspiration port 116). Providing irrigation in the direction of the aspiration port 116 (e.g., by curving the distal end having the irrigation port 136 toward the aspiration port 116) may advantageously increase the suction pressure experienced at the aspiration port 116, which may facilitate the removal of kidney stones. Additionally or alternatively, the irrigation tube 130 may include a lateral irrigation port 136. The irrigation port 136 may be positioned on the side of the irrigation tube 130 facing toward the path of suction leading into the aspiration port 116. In some embodiments, the distal end 106 of the catheter 102 or the distal end of an irrigation tube 130 may be curved toward a proximal direction so as to face at least partially toward a lateral aspiration port 116, as depicted in FIG. 15D. In some embodiments, the catheter 102 may include both distal-facing and lateral-facing aspiration ports 116. FIGS. 15E and 15F depict a perspective view and cross section, respectively, of an example of a catheter 102 comprising a distal-facing aspiration port 116 and a lateral-facing aspiration port 116 in addition to a distally facing irrigation port 136. In some embodiments, the irrigation port 136 may be positioned on a substantially opposite side of the catheter 102 as the lateral-facing aspiration port 116 (approximately 180 degrees circumferentially offset).

The shape of the one or more irrigation streams ejected from the one or more irrigation ports 136 may also depend on other hydrodynamic properties, including the flow rate or pressure of the irrigation fluid, the viscosity of the irrigation fluid, the pressure of the external environment, the viscosity of fluid within the external environment, etc. In some embodiments, irrigation may be provided at a flow rate of about 1, 5, 10, 20, 25, 30, 40, 50, 60, 70, 80, 90, 100, 125, 150, 200, 300, 500, less than 1, or greater than 500 ml/min, or a flow rate selected from a range there between. In some embodiments, negative pressure may be applied to provide suction or positive pressure may be applied to drive irrigation at a pressure of about 5, 10, 20, 25, 30, 40, 50, 60, 70, 80, 90, 100, 125, 150, 200, 300, 500, 1000, 2000, 5000, less than 1, or greater than 5000 mmHg, or a pressure selected from a range there between. In some implementations, the vacuum may be maintained below a maximum pressure (e.g., 150 mmHg) for safety reasons. The irrigation stream may be configured to provide laminar flow or turbulent flow for a particular application (e.g., use within the ureter or kidney). The dimensions of the irrigation lumen 134 and nozzle as well as the amount of pressure applied to the irrigation fluid may be used to configure the type of fluid flow from the irrigation port 136. The pressure applied to the irrigation fluid may be dynamic, even during periods when irrigation fluid is continuously delivered. For example, the pressure may be oscillated (e.g., via a sinusoidal waveform) providing a pulsed pressure effect. The shape, spread, flow rate, and/or type of flow of the irrigation stream may oscillate or otherwise vary along with the differential pressure applied to the irrigation fluid. The catheter 102 may be configured to expel pulses of irrigation fluid or higher pressurized pulses of irrigation fluid at a certain frequency (e.g., less than 0.1 Hz, 1 Hz, 10 Hz, 50 Hz, 100 Hz, more than 100 Hz, etc., or a frequency selected from a range there between). The dynamic irrigation stream may be configured to optimize removal of kidney stones. The positive pressure source which pressurizes the irrigation fluid may be coupled to and controlled by a controller. The controller may have means for adjusting the parameters of the irrigation, such as the frequency of pulsing and/or pressure of pulsing. In some implementations, the levels of suctioning and irrigation may be matched to provide constant pressure or volumetric flow within the physiological lumen or cavity (e.g., the kidney). For instance, the matching may maintain a substantially constant level of irrigation fluid within a space such as a calyx. In some implementations, irrigation may provide more pressure or volumetric flow than suctioning. In some implementations, irrigation may provide less pressure or volumetric flow than suctioning. Over-pressurization may be prevented such as by finger port 228 as described elsewhere herein which may equilibrate the pressure with the ambient atmosphere. Too little irrigation may not dislodge a kidney stone and/or may not prevent suctioning of adjacent tissue. Too much irrigation, particularly relative to the amount of suction, may dislocate the kidney stone away from the catheter 102 before it is caught up in the suctioning of the catheter 102.

In some embodiments, the catheter 102 may comprise more than one irrigation lumen 134, as described elsewhere herein. In embodiments, comprising a plurality of irrigation lumens 134, each lumen may be connected to the same or to different sources of positive pressure. In embodiments where a plurality of pressure sources are connected to a plurality of irrigation lumens 134, the same pressure profile may be applied to each lumen or the irrigation through each lumen may be separately controlled according to different pressure profiles. In some embodiments, the irrigation flow through a plurality of irrigation lumens 134 may be configured to create a particular flow pattern at the distal end of the catheter 102. Pressurized irrigation fluid may be provided to the plurality of irrigation lumens 134 such that irrigation fluid is expelled at different times, for different durations, and/or at different pressures and flow rates from the plurality of irrigation ports 136. For example, the catheter 102 may comprise a plurality of irrigation ports 136 positioned around a circumference of the distal end 106 of the catheter 102 (e.g., around an aspiration port 116) and irrigation fluid may be expelled from the plurality of irrigation ports 136 in a sequential pattern travelling clockwise or counterclockwise. The period of positive flow from each irrigation port 136 may overlap with an adjacent irrigation port 136 or may not overlap. In some embodiments, irrigation fluid may be continuously expelled from each irrigation port 136 over a period of time, but a wave of high pressurization may travel along the circumference of the distal end of the catheter 102, alternatively applying a pulse of high pressure to one or more of the plurality of irrigation ports 136. A number of combinations and various patterns are possible. In some embodiments, the controller may comprise a number of pre-set programs for applying particular pressure profiles or irrigation sequences to the catheter 102 that a user may select from for the procedure. Providing dynamic irrigation, in terms of the spatial and/or temporal distribution of the irrigation flow from a stationary catheter, may create flow patterns that are configured to dislodge debris, such as kidney stones from physiological tissue.

Various combinations and patterns of aspiration (suction) and irrigation may be applied by the catheter 102 during a procedure, such as a procedure to remove kidney stones from the kidney, ureter, or other portion of the urinary tract. In some embodiments, both suction and irrigation may be provided continuously. In some embodiments, suction may be provided continuously and irrigation may be provided intermittently. In some embodiments, irrigation may be provided continuously and suction may be provided intermittently. In some embodiments, both suction and irrigation may be provided intermittently. In embodiments where suction and/or irrigation is provided intermittently, the intermittent application of suction and/or irrigation may be provided automatically based on a predetermined profile or may be provided manually by the spontaneous control of a user (e.g., during a period for which the user actuates a control, such as a button or finger port 228 on the handle 200 of the catheter 102). In some embodiments, the user may use a control to transiently override a predetermined profile. In some embodiments, the irrigation and/or aspiration, as well as any other function that may be included in the removal device 100, can be controlled by a controller. The controller may include memory and/or a processor. The controller may store programs or algorithms for operating irrigation and/or aspiration of the removal device 100. The controller may be an integral part of the device (e.g., part of the handle 200) or may be a stand-alone device. The stand-alone device may be connected to the vacuum source and pressurized fluid source electronically (e.g., through one or more cables or wirelessly) or may be part integral with the vacuum source and pressurized fluid source. The vacuum source and pressurized fluid source may be connected to the handle 200 through one or more vacuum tubes and one or more irrigation lines. The tubes and lines may be combined into single cables. In some embodiments, the controller may be intermediately positioned along the vacuum tubes and irrigation lines, such that they run through the controller. The controller may include and/or control pumps and/or valves, which it uses to create or modulate the pressure of aspiration and irrigation applied to the removal device 100 and/or to selectively apply pressure to various tubes or lines. The controller may include an interface for receiving input or commands from a user (e.g., buttons, dials, sliders, keyboards, a mouse, a stylus, touchscreens, etc.). A user may set values of aspiration pressure and/or irrigation pressure or flow rate via the controller. The values may be incremental or continuous (e.g., analog). In some embodiments, the user may be able to select which vacuum lumen 114 and/or irrigation lumen 134 is activated (provided pressure). In some embodiments, the removal device may be operatively connected to a computer, laptop, tablet, which may serve as the controller. The device may include a display (e.g., a display screen or a digital numerical indicator). A collection container may be placed downstream of the vacuum lumen 114 for collecting debris. In some embodiments, the device may include a safety shut-off feature, such as an automatic pressure release valve, if a measure pressure (such as in the vacuum lumen 114) exceeds a predetermined threshold.

In some embodiments, intermittent suction may be provided simultaneously with intermittent irrigation. In some embodiments, intermittent suction and intermittent irrigation may be provided alternatively to one another. That is, suction may be provided during any period in which irrigation is not provided and irrigation may be provided during any period in which suction is not provided. For example, in some implementations, irrigation may be provided as a default, except during a period when suction is positively activated by a user in which case irrigation is temporarily stopped. In other implementations, suction may be provided as a default, except during a period when irrigation is positively activated by a user in which case suction is temporarily stopped. In some embodiments, periods of suction and irrigation may overlap partially but not entirely. In some embodiments, periods of suction and/or irrigation may be repeated at a regular interval. The periods of suction and/or irrigation may endure about 0.1 s, 1 s, 5 s, 10 s, 15 s, 20 s, 30 s, 45 s, 60 s, less than 0.1 s, more 60 s, or a duration in any range there between. The periods of rest (no suction and/or no irrigation) may be about 0.1 s, 1 s, 5 s, 10 s, 15 s, 20 s, 30 s, 45 s, 60 s, less than 0.1 s, more 60 s, or a duration in any range there between. In some embodiments, the periods of suction may be about 1×, 1.25×, 1.5×, 1.75×, 2×, 3×, 5×, 10×, 50×, 100×, less than 1×, more than 100×, or a multiple in any range there between longer than the period of irrigation. In some embodiments, the periods of irrigation may be about 1×, 1.25×, 1.5×, 1.75×, 2×, 3×, 5×, 10×, 50×, 100×, less than 1×, more than 100×, or a multiple in any range there between longer than the period of suction. There may be 1, 2, 3, 4, 5, 10, 20, 30, 50, 100, more than 100 pulses of irrigation, or a number in any range there between, for each pulse of suction. There may be 1, 2, 3, 4, 5, 10, 20, 30, 50, 100, more than 100 pulses of suction, or a number in any range there between, for each pulse of irrigation.

As described elsewhere herein, pulsatile irrigation and/or pulsatile suctioning may be provided as continuous or stepped reductions/increases in irrigation or suction pressure (e.g., comprising a sine wave profile or any other suitable profile), may be provided as switching pressure on and off altogether (e.g., a square wave profile or any other suitable profile), or may be provided as any combination thereof.

Pulsatile irrigation and pulsatile suctioning (aspiration) may be provided separately, simultaneously, or only one of irrigation and suctioning may be pulsed. When provided together, pulsatile irrigation and pulsatile suctioning may be synchronized. For example, suctioning may increase as irrigation decreases and vice versa. Alternatively, suctioning and irrigation may increase and decrease together. Pulsatile irrigation and pulsatile suctioning may be provided at the same or different frequencies. The removal device 100 may be configured to provide combinations of pulsatile, continuous, and/or on-demand suctioning and/or irrigation. In some implementations, kidney stone removal may be optimized by effectively placing the kidney stones in suspension within the kidney. Kidney stone removal may further be optimized by effectively fluidizing the suspended kidney stones. Breaking the kidney stone into smaller sized kidney stones may facilitate suspending and/or fluidizing the kidney stones. In some implementations, providing high frequency suctioning and/or high frequency irrigation may optimize kidney stone removal. Frequencies above, for example, about 1 Hz, 10 Hz, 50 Hz, 100 Hz, 500 Hz, 1 kHz, or more than 1 kHz may be considered high frequency pulsing. High frequency pulsing of suctioning and/or irrigation may help place kidney stones in suspension and/or may help fluidize the kidney stones such that they are more readily removed via the removal device 100.

In some implementations, it may be most effective to systematically load and unload a calyx containing stones with irrigation fluid. In other words, the calyx may be substantially filled with irrigation fluid and then suction may be initiated to aspirate the volume of irrigation fluid from the calyx. Irrigation may be halted during suctioning or the rate of irrigation may be slower than the rate of suctioning such that there is a net decrease in the volume of the irrigation fluid. In other embodiments, the rate of irrigation may be substantially equal to the rate of suctioning, in which case suctioning may not decrease the net volume of irrigation fluid within a space, but the volume may nonetheless be gradually replaced with fresh irrigation fluid. Some tests have shown that stones are more efficiently removed from the kidney using relatively longer durations of suctioning and/or less frequent applications of suctioning. For example, the suctioning may be at least 1 s, 2 s, 3 s, 4 s, 5 s, 6 s, 7 s, 8 s, 9 s, 10 s, 11 s, 12 s, 13 s, 14 s, 15 s, 20 s, 25 s, 30 s, or more than 30 s long. Similarly, periods of irrigation without suctioning may be at least 1 s, 2 s, 3 s, 4 s, 5 s, 6 s, 7 s, 8 s, 9 s, 10 s, 11 s, 12 s, 13 s, 14 s, 15 s, 20 s, 25 s, 30 s, or more than 30 s long. The application of suctioning to the volume of irrigation fluid may facilitate fluidizing the stones within the irrigation fluid. For instance, application of suctioning may impart momentum to the stones which makes them easier to remove. Pulses of aspiration less than a threshold duration may cease before the stones are optimally fluidized, hampering the removal of stones, yet, may decrease the total irrigation volume, making subsequent fluidization more difficult. Periods of irrigation without suctioning may serve to fill or refill a calyx or other space with irrigation fluid. Periods of net positive irrigation less than a threshold value may not adequately fill the space and may lead to sub-optimal fluidization of the stones within the space during subsequent periods of aspiration. Maintaining a minimum level of irrigation volume within a space during aspiration may decrease the chances of tissue damage from the suctioning as described elsewhere herein. Some embodiments include a period of irrigation in which from 1 cc to 20 cc, from 5 cc to 15 cc, from 8 cc to 12 cc, or about 10 cc of irrigation fluid is infused into a calyx followed by sustained aspiration lasting from 0.2 s to 10 s, from 0.5 s to 5 s, from 0.8 s to 3 s, or from 1 to 2 s. In such embodiments, irrigation fluid may continue to be infused during the aspiration period, or may be discontinued during the aspiration period.

In some implementations, a stone collection canister, as described elsewhere herein, or other fluid trap connected downstream of the aspiration lumen may be used to monitor user cycling of aspiration. For example, the fluid trap may hold a certain of volume of fluid (e.g., via gravity) before the fluid rises to an exit port and continues to flow along the aspiration pathway. The user may visually monitor the volume level of the fluid trap. One or more volume levels could be quantitatively or qualitatively (e.g., full, half-full, etc.) indicated on the fluid trap through markings (e.g., hash-marks) or other suitable means. The volumes within the fluid trap could be calibrated to the particular application, such as to the volume of a renal calyx. When the collected volume rises to a certain level, the volume could serve as an indicator to the user to halt the suctioning (e.g., by covering a finger port 228) and/or to reinitiate irrigation. In some embodiments, the indicator volume may be a volume at which the collected fluid rises to the exit port and begins flowing through an upstream aspiration line. In some implementations, the user may halt suctioning and/or initiate irrigation when fluid is observed to stop flowing through the aspiration line, indicating the body space (e.g., the calyx) is substantially empty (or that the vacuum lumen 114 is clogged). One or more cycles of aspiration may be performed within each target space, as described elsewhere herein. In some embodiments, a fluid syringe used for supplying irrigation fluid, such as a SAPS™ syringe, may automatically refill upon release of the syringe, facilitating successive flushing of the calyx or other body space. In some implementations, the time it takes to empty and/or refill a syringe may be used to calibrate the duration of the aspiration and/or irrigation pulses.

Disclosed herein are also various methods for using a removal device comprising aspiration and irrigation to remove kidney stones from the kidney, ureter, or other portion of the urinary tract. The methods described herein may be performed with embodiments of the removal device 100 and systems described herein or any other suitable device. The removal device 100 comprising aspiration and irrigation can be inserted through the urethra to a point along the urinary tract proximate to one or more kidney stones. The removal device 100 may be inserted proximally of the one or more kidney stones or the device may be inserted distally of the one or more kidney stones. In some embodiments, the removal device 100 is advanced in a distal direction toward and/or past the plurality of kidney stones while applying aspiration and/or irrigation. For example, the removal device 100 may be advanced from the renal pelvis, into a major calyx of the kidney, and further into a minor calyx of the kidney, or along any portion of such a path. In some implementations, the removal device 100 may provide aspiration and/or irrigation according to one of the patterns or profiles described elsewhere herein during the advancement of the removal device 100. In some embodiments, the removal device 100 is retracted in a proximal direction past and/or away from the plurality of kidney stones while applying aspiration and/or irrigation. For example, the removal device 100 may be retracted from a minor calyx of the kidney, into a major calyx of the kidney, and further into the renal pelvis, or along any portion of such a path. The removal device 100 may provide aspiration and/or irrigation according to one of the patterns or profiles described elsewhere herein during the retraction of the removal device 100. In some embodiments, the removal device 100 may be reciprocated along a proximal-to-distal direction. For example, the removal device 100 may be moved back and forth along trajectory between the renal pelvis and a minor calyx or along a smaller trajectory defined therein or along a larger trajectory encompassing such a path. The removal device 100 may be reciprocated back-and-forth for any number of suitable cycles (e.g., 1 cycle, 2 cycles, 3 cycles, 4 cycles, 5 cycles, 10 cycles, 20 cycles, 50 cycles, 100 cycles, more than 100 cycles, or any number cycles in a range there between, etc.). The removal device 100 may be reciprocated at a substantially constant frequency.

In some implementations, the removal device 100 is manually translocated in a distal and/or proximal direction by the user manually moving a proximal portion of the removal device 100 outside of the body (e.g., handle 200) in a proximal and/or distal direction. In some implementations, the removal device 100 comprises an internal component and an external component surrounding the internal component. The internal component and/or the external component may be independently advanceable with respect to the other for at least some separable distance. For example, the internal component may be a vacuum tube 110 and the external component may be a concentric irrigation tube 130. The vacuum tube 110 may be able to be advanced distally and retracted proximally while the irrigation tube 130 remains stationary and/or the irrigation tube 130 may be able to be advanced distally and retracted proximally while the vacuum tube 110 remains stationary. In some embodiments, the internal component and the external component may be separable such that the distal end of the internal component may be positioned either distally to or proximally to the distal end of the external component. In some embodiments, the internal component and the external component may be separable such that the distal end of the internal component is always distal to (or at least aligned with) the distal of the external component or the distal end of the external component is always distal to (or at least aligned with) the distal end of the internal component. In some embodiments, a catheter 102 comprising the vacuum tube 110 and one or more irrigation lumens 134 may be the internal component and an external sheath may be the external component. Use of an external sheath may prevent pain, discomfort, or irritation along a length of the urinary tract by allowing the internal component to move back and forth freely while providing a stationary barrier between the internal component and the urinary tract over a large portion of the length of the catheter 102.

In some embodiments, the internal component or the external component may be proximally and distally translatable using a mechanism provided on a handle 200 configured to be positioned outside the body of the patient. For example, the handle 200 may comprise a lever or a sliding knob which is coupled to the internal component. The user may distally advance or proximally retract the internal component by actuating the mechanism. The mechanism may limit the amount of separation achievable between the internal component and the external component. In some embodiments, an irrigation port 136 (e.g., irrigation tube 130) may be proximally retracted during suction. Retracting the irrigation port 136 may dissipate the displacement force of the irrigation stream after dislodging a kidney stone and allow the aspiration port 116 to better capture the kidney stone. In some embodiments, the irrigation port 136 is advanced distally during aspiration. Advancing the irrigation port 136 may increase irrigation pressure to facilitate dislodging a kidney stone. The irrigation pressure may be adjusted as needed by axially translocating the irrigation port 136. In some embodiments, the aspiration port 116 (e.g., vacuum tube 110) is axially translocated to induced the same effects. In some embodiments, an aspiration port 116 and an irrigation port 136 are axially moved relative to one another, simultaneously and/or sequentially.

Figure 16A:
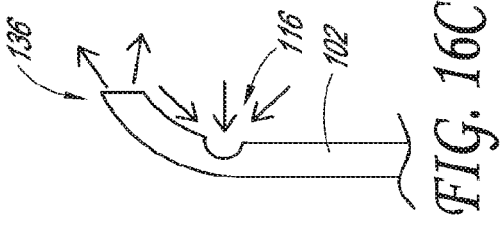
FIGS. 16A-16E schematically depict various movements or ranges or motion the distal end of the catheter may be configured to perform.
Figure 16B:
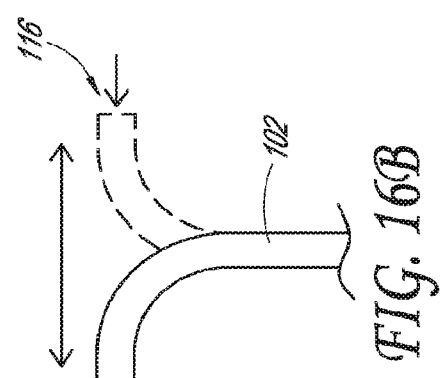

FIGS. 16A-16E schematically illustrates various examples of movement capable of being performed by the removal device 100. In some embodiments, a distal portion of the removal device 100 may be steerable, as described elsewhere herein. The removal device 100 may be inserted to a location proximate one or more kidney stones. The distal portion of the removal device 100 may be moved in a lateral direction (e.g., left-to-right, right-to-left, upward, downward, or any direction there between), as depicted in FIG. 16A, while applying aspiration and/or irrigation. In some implementations, the removal device 100 may provide aspiration and/or irrigation according to one of the patterns or profiles described elsewhere herein during the lateral movement of the distal portion. The removal device 100 may be moved in one direction or may be moved back-and-forth in a reciprocating motion, as depicted in FIG. 16B. The removal device 100 may be moved in various different intersecting trajectories, such as left-to-right, up-to-down, and/or diagonals between those orthogonal directions, as shown in FIG. 16A. Lateral movement may be used to create a sweeping motion of the distal end of the removal device 100. The lateral movement may increase the area or volume that is swept by the catheter 102 and may improve the efficiency of kidney stone removal.

Figure 16C:
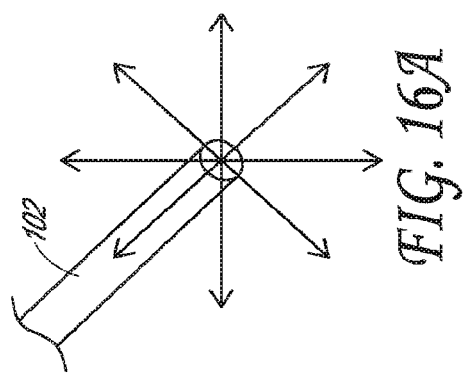

Moving the distal portion of the removal device 100 in a lateral direction may be accomplished by bending a distal length of the removal device 100 such that it curves away from a longitudinal axis defined by a proximal portion of the removal device 100. Providing a single bend in the distal portion of the removal device 100 may cause aspiration ports 116 and/or irrigation ports 136 formed in the distal portion of the removal device 100 to alter their orientation as the distal portion is moved, as shown in FIG. 16B. For example, aspiration ports 116 and/or irrigation ports 136 formed in a distal face of the catheter 102 such that they face a distal direction parallel with the longitudinal axis of the catheter 102 when unbiased may be turned toward a lateral direction substantially orthogonal to the longitudinal axis (of the unbiased device) or some direction in between the longitudinal axis (0 degrees) and an orthogonal direction (90 degrees). In some implementations, the face may be turned even further (more than 90 degrees) such that it is facing at least partially toward the proximal direction aligned along the longitudinal axis, as described elsewhere herein. In some embodiments, the removal device 100 may comprise one or more ports along a lateral sidewall of the catheter 102 (e.g., an aspiration port 116). The one or more ports may be positioned along the length of the steerable portion and/or proximal to the steerable portion. In some implementations, kidney stone removal may be facilitated by bending the steerable distal portion toward the side comprising a lateral aspiration port 116, as depicted in FIG. 16C. In some implementations, kidney stone removal may be facilitated by bending the steerable distal portion in a direction away from the side comprising a lateral aspiration port 116 (180 degrees from the aspiration port 116). In some implementations, kidney stone removal may be facilitated by bending the steerable distal portion along a direction somewhere between the side comprising the lateral aspiration port 116 and the opposite side (between 0 degrees and 180 degrees).

Figure 16D:
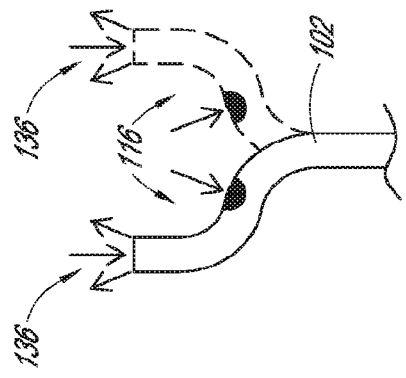

In some embodiments, the steerable distal portion of the removal device 100 may be configured to bend in more than one direction. For example, the distal portion may have two bends that form curves in opposite directions within the same plane. A distal portion having a least two bends may be configured to bend in a manner such that the distal face of the removal device 100 remains facing in a distal direction as the distal portion is moved laterally (e.g., swept left-to-right), as shown in FIG. 16D. In some embodiments, a lateral port (e.g., an aspiration port 116) may be positioned in a steerable portion comprising a first curve or in a steerable portion comprising a second curve. In some embodiments, the lateral port may be positioned between first and second curves. In some embodiments, the distal steerable portion may be configured to form curves in different planes. In some embodiments, more than two curves may be formed along the length of the distal steerable portion. In some embodiments, each curve may be independently controllable, such that a user can modulate the degree of bending in the individual curve, such as using a control mechanism on a proximal handle 200. In some embodiments, the removal device 100 may be configured to assume a predetermined conformation comprising multiple curves upon actuation of a control mechanism. For example, activating the control mechanism a certain amount may be configured to bend one curve a first amount (e.g., number of degrees) in a first direction and to bend a second curve a second amount (e.g., number of degrees) in a second direction.

Figure 16E:
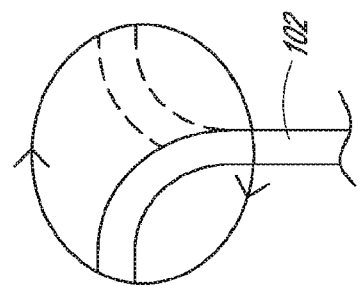

In some embodiments, the removal device 100 or a portion of the removal device 100 may be rotated along the longitudinal axis of the removal device 100 while applying aspiration and/or irrigation. In some implementations, the removal device 100 may provide aspiration and/or irrigation according to one of the patterns or profiles described elsewhere herein during the rotation of the removal device 100. In some embodiments, the removal device 100 may comprise an inner component (e.g., a combined aspiration and irrigation catheter 102 or a vacuum tube 110) and an outer component (e.g., an outer sheath or an irrigation tube 130), as described elsewhere herein. The inner component and/or the outer component may be independently rotatable with respect to the other. In some embodiments, one or both of the components are rotated during aspiration and/or irrigation. If both components are rotated, they may be rotated in the same direction, at the same speed or at different speeds, or in opposite directions, at the same speed or at different speeds. In some embodiments, the entire removal device 100 is configured to be rotatable within the urinary tract. Rotation of the removal device 100 or a portion of the removal device 100 may be useful for moving the distal end of the removal device 100 along a curved trajectory, such as an arc or a circle. For example, 360 degree rotation of the removal device 100 while a steerable distal portion is in a bent configuration will result in the distal tip of the removal device 100 moving in a circular pattern centered around the longitudinal axis of the removal device 100, as depicted in FIG. 16E. More complex trajectories may be created by dynamically bending the steerable distal portion while rotating the removal device 100 or a portion thereof and/or while advancing the removal device 100 in a distal direction or retracting it in a proximal direction. The various features of the methods described herein may be combined in any feasible manner, such that more complex patterns of motion are achievable by the user. These patterns of motion may be combined with the specific patterns of aspiration and/or irrigation disclosed herein to create optimized procedures for the removal of kidney stones.

In some implementations, kidney stone removal may be optimized by strategically positioning the catheter 102 proximate to a target kidney stone prior to providing suction and/or aspiration through the catheter 102. Kidney stones may be removed by positioning the catheter 102 such that the target kidney stone is aligned with an aspiration port 116 configured (e.g. sized) to remove the kidney stone. The aspiration port 116 may be positioned on either a distal face or lateral side of the catheter 102. For instance, the catheter 102 may be positioned such that the target kidney stone is positioned directly in front of the distal face of the catheter 102 comprising a distal-facing aspiration port 116. In some embodiments, the aspiration port may be positioned within or about approximately 0.005 inches, 0.01 inches, 0.02 inches, 0.03 inches, 0.04 inches, 0.05 inches, 0.06 inches, 0.07 inches, 0.08 inches, 0.09 inches, 0.1 inches, 0.2 inches, 0.3 inches, 0.4 inches, 0.5 inches, 0.6 inches, 0.7 inches, 0.08 inches, 0.09 inches, 1 inch, less than 0.005 inches, or more than 1 inch away from the target kidney stone. Positioning the aspiration port to be aligned with the target kidney stone may comprise any one or more of the movements described herein, such as axially translating the catheter 102, rotating the catheter 102, and/or bending one or more distal portions of the catheter 102. Once the aspiration port 116 is positioned within an optimal alignment (e.g., directly aligned) and range of the target kidney stone, aspiration and/or irrigation may be provided to capture the kidney stone. Irrigation may dislodge the target kidney stone, provide pressure to prevent suctioning of adjacent tissue into the suction path, and/or move the kidney stone (e.g., toward the aspiration port 116). Suctioning may draw the target kidney stone into the vacuum lumen 114 for removal. Once suctioning and/or irrigation are applied, the catheter 102 may not need to be moved or repositioned in order to remove the target kidney stone. The kidney stone may be removed from the body without removing the catheter from the kidney. In some implementations, once the target kidney stone is successfully aspirated, suctioning and/or irrigation may be stopped. The catheter 102 may be subsequently repositioned (e.g., while suctioning and/or irrigation are halted) in optimal alignment and range for capturing a subsequent kidney stone. Positioning the catheter 102 in optimal alignment and range may be advantageous in that it prevents the irrigation from moving the target kidney stone away from the catheter 102 prior to the aspiration port being in position to capture the target kidney stone. In some implementations, a guidewire is first positioned adjacent or near a kidney stone (e.g., using direct visualization) and a flexible catheter 102 is subsequently guided into position via the guidewire, with or without direct visualization. The flexible catheter 102 may be repositioned (e.g., in different calyces) using a guidewire and/or a scope for direct visualization. The guidewire and/or scope may be removed prior to initiation irrigation and/or aspiration. Steerable embodiments of the catheter 102 may be able to efficiently remove kidney stones without precise positioning and may be more suitable for performing blindly (without direct visualization, but using indirect visualization such as fluoroscopy and/or ultrasound).

In some embodiments, the target kidney stone is guided to the aspiration port 116. For instance, a shield or basket on an ancillary member, as described elsewhere herein, may be used to guide the kidney stone toward an aspiration port 116 on the catheter 102. An ancillary irrigation tube 130 may be used to push or direct a kidney stone toward the aspiration port 116 via an irrigation stream. The catheter 102 may remain relatively stationary while the kidney stone is guided toward the aspiration port 116. In some embodiments, the operator may not be able to visualize the kidney stones. The shield or other guiding device may be used in a sweeping or scooping motion that would generally cover an entire area of a region (e.g., a pole or calyx) and ultimately guide any kidney stones to an optimal alignment and range in front of an aspiration port 116 of the catheter 102. In some embodiments, the kidney stone is guided to the aspiration port 116 using the catheter 102 itself, such as by contacting the kidney stone with the catheter 102. The distal end 106 of the catheter 102 may be used to contact and guide the kidney stone. In some embodiments, the catheter 102 may have a surface or otherwise be shaped (e.g., scoop shaped such as in FIG. 4G) to facilitate contacting and/or guiding the kidney stone. In some embodiments, the catheter 102 may include a shield member similar to that described elsewhere herein. In some embodiments, the kidney stone is guided to the aspiration port 116 using an irrigation stream coming from the irrigation port 136. In some implementations, the kidney stone may be guided from a first position in the kidney to a second position in the kidney. The second position in the kidney may be more optimal for aligning the aspiration port 116 with the kidney stone. For example, the kidney stone may be less prone to dislocation, such as under the force of irrigation, in the second location than in the first location. Subsequent kidney stones may be moved from a third position to the first position or to a fourth position, which may be more optimal for aligning the aspiration port 116 with the kidney stone than the third position.

Kidney stone removal may be optimized by strategically performing aspiration and/or irrigation in an ordered sequence across various locations. For example, kidney stone removal may be optimized by performing a specific operation comprising a particular sequence of movements and/or a particular pattern of aspiration and/or irrigation at a location then moving the removal device 100 to a subsequent location and performing another specific operation, which may be the same or different from the first operation. This strategy may be repeated over a plurality of locations. In some embodiments, the therapeutic procedure may be performed in a downstream direction. For example, a kidney stone removal operation may be performed in a minor calyx then retracted into the major calyx where another operation is performed. The operation may be repeated any number of times before moving to another location. From the major calyx, the removal device 100 may be retracted into the renal pelvis where another operation may be performed. From the renal pelvis the removal device 100 may be retracted into the ureter where another operation may be performed. Any of the aforementioned locations may be excluded. For example, a therapeutic aspiration and/or irrigation operation may not be performed in the minor calyx and/or may not be performed in the ureter. Any preceding and/or subsequent locations may be combined with a given location such that the operative range of motion of the operation spans the two or more locations across which an operation is performed before substantially repositioning the removal device 100. For example, a therapeutic aspiration and/or irrigation operation may comprise a range of motion extending through both a major calyx and a minor calyx, such as a motion trajectory involving reciprocation between the major calyx and the minor calyx. The procedure may involve moving from branch to branch, wherein a branch comprises the renal pelvis, a major calyx, and an adjoining minor calyx, or a portion thereof. The procedure can be performed by moving to adjacent minor calyces within a branch before moving to adjacent major calyces. In some embodiments, a downstream location may be repeatedly operated upon as various branches are traced. In some embodiments, a downstream location may only be operated upon after completion of all upstream locations. In some embodiments, the same sequence of operations may be performed in a reverse order. That is, a series of therapeutic aspiration and/or irrigation operations may be sequentially performed across various locations, generally moving in an upstream direction, such as from the ureter, to the renal pelvis, to a major calyx, to a minor calyx. Procedures may be performed moving from branch to branch while performing therapeutic aspiration and/or irrigation operations in an upstream direction.

In some embodiments, a removal procedure is initiated with the catheter 102 in a relatively distal position. Irrigation may be applied from the catheter 102 prior to suctioning. In some embodiments, the irrigation may advantageously generate a vortex effect. In some embodiments, the irrigation may generally fill, or at least partially fill, a major or minor calyx with irrigation fluid. Suctioning may then be provided as the catheter 102 is retracted in a proximal direction. The distal end 106 of the catheter 102 may be articulated to sweep the calyx or pole as the catheter 102 is retracted. Suctioning may be provided intermittently during the procedure. Irrigation may be provided continuously throughout the procedure. The procedure may be repeated as necessary. In other embodiments, the same procedure is performed but the catheter 102 is advanced distally during the procedure.

In some embodiments, the catheter 102 is positioned in each of the three kidney poles (upper, middle, and lower) and swept within each pole. For instance, the catheter may be distally advanced into one pole and then the distal end of the catheter 102 may be steered to sweep the area of the pole. After one pole is swept, the catheter 102 may be proximally retracted then distally advanced into the next pole and the procedure repeated. In some implementations, the catheter 102 may be swept in incremental steps. For instance, the distal end 106 of the catheter 102 may be moved across a number of positions and stopped. Aspiration and/or irrigation may be stopped during steering/sweeping of the catheter 102 and then applied for a duration of time while the catheter 102 is maintained in constant position. The sweep pattern may be configured to cover substantially the entire pole. The sweep pattern may move in the same direction as kidney stones tend to move under the force of irrigation (e.g., in the direction of gravity), such that the final destination of the sweep pattern is a point of the pole where any non-aspirated kidney stones are expected to have accumulated. In some implementations, aspiration and/or irrigation may be applied during the sweeping movement or steering of the catheter 102. In some implementations, the procedure may be performed in the upper pole, followed by the middle pole, and finally in the lower pole, as kidney stones may tend to be relocated and accumulate in the lower pole during the procedure. In other implementations, the procedure may be performed in the reverse order or the procedure may be performed in the middle pole then either the upper pole or the lower pole. In some implementations, irrigation may be used to positively flush all the kidney stones into one pole (e.g., the lower pole) and then the removal procedure may be performed in that pole. In some embodiments, kidney stones may be captured or guided into the catheter 102 using a shield or basket device, such as described elsewhere herein. The shield or basket device may be most optimally used in a pole providing the straightest path (e.g., the middle pole).

In some embodiments, the pole with the straightest path may be operated on last and/or a shield or basket device may be used in that pole.

In some implementations, the removal procedure may be performed without the use of a ureteroscope or other direct visualization device, at least during the aspiration and/or irrigation portion of the procedure (when the kidney stone is removed). In some instances, blood produced using a laser for lithotripsy may obscure the visibility of direct visualization modalities. The procedure may be monitored using indirect visualization such as fluoroscopy (e.g., via retrograde pyelogram) and/or ultrasound. Contrast agent may be introduced into the body (e.g., the kidney) via the irrigation lumen or lumens 134 of the removal device 100. In some embodiments, a fiberoptic device (for direct visualization) may be used during the procedure. A fiberoptic lens may be carried on a thin wire that is relatively thin relative to the dimensions of a scope (e.g., an endoscope or ureteroscope). A fiberoptic device may advantageously allow direct visualization while minimally or negligibly reducing the dimensions of the vacuum lumen 114 such that large stones may be suctioned through the removal device 100. Fiber optic cables may run the length of the catheter for introducing light to the in vivo space and/or collecting light from the in vivo space (e.g., two fibers). Fiberoptics may advantageously reduce the heat generated with the use of LED light sources in traditional endoscopes. The camera for use with fiber optics may consume about 1 mm$^2$ of surface area or less and may be positioned at a distal end of the catheter 102 or at a proximal end (e.g., within the handle 200). Kidney stones may not be visible under the indirect visualization. The catheter 102 may comprise radiopaque materials (e.g., a metal coil) and/or may include radiopaque marker bands, such as at a distal end of the device, so that the catheter 102 is visible under fluoroscopy. The distal end 106 of the catheter may be swept through a range of positions, as described elsewhere herein, where kidney stones are expected to be located. The catheter 102 may be strategically swept or repositioned along a direction that kidney stones are likely to have dislocated, as described elsewhere herein, in order to maximize the probability of removing residual kidney stones. In some implementations, contrast agent may be used to monitor the removal procedure. The aspiration (removal from the body) of the contrast agent may indicate the location of the distal tip of the catheter 102 in real-time. Areas which do not contain contrast agent (e.g., are not visible) may be assumed to have already been aspirated. Thus, in some implementations, the aspiration procedure may be conducted until all or significantly all of the contrast agent is removed from the kidney, or at least form the renal calyces.

As an example of a removal procedure, a steerable catheter 102 may be used to sweep each calyx of the target kidney. The catheter 102 may be navigated into each of the major calyces or poles, using the steerability to create an appropriate bend where required (as determined under fluoroscopy), within which a sweep procedure may be conducted. The user may be able to discern the placement of the distal end of the catheter 102 into a target calyx via tactile feedback. For instance, the user may sense less resistance on a lever that is being used to articulate a bend in the catheter 102 and/or may observe less resistance in axially translating the catheter 102 (e.g., in a distal direction) as the distal end enters a calyx. The calyces may be targeted in an upper to lower order (e.g., upper pole, middle pole, lower pole). The sweep procedure may require initiating irrigation and suctioning if not already being applied. In some embodiments, the distal end 106 of the catheter 102 is introduced into the target calyx while suction and irrigation are being applied. In some embodiments, the distal end 106 is introduced into the target calyx without either suction or irrigation. In some embodiments, the distal end 106 is introduced with irrigation but without suction, such as when continuous irrigation is being applied. Suctioning may be prevented by disconnecting the vacuum source, by having the vacuum source in an off position, and/or by operation of a suction valve such as a finger port 228. In some embodiments, the calyx may be sufficiently flushed with irrigation fluid prior to the initiation of suctioning. Doing so may prevent the suctioning from sticking to the kidney tissue and potentially injuring the tissue. The passive outflow of irrigation fluid through the finger port 228 or another port in fluid communication with the kidney may be used to indicate that a sufficient amount of irrigation fluid has been delivered to the target calyx. Once the calyx is sufficiently filled with irrigation fluid, suctioning may be initiated. The suctioning procedure may be performed quickly enough such that the calyx is not emptied or the fluid level within the calyx does not fall below a threshold level (e.g., to prevent sticking of kidney tissue to the catheter 102) during the sweep procedure. The suctioning may be approximately correlated to the irrigation flow (e.g., it may remove the same volume of irrigation fluid as is delivered over a timeframe) or it may remove more or less fluid than is being delivered. In some embodiments, a manual irrigation source is used, such as a syringe, and the manual irrigation source can provide feedback to the user regarding whether the catheter tip is obstructed. For example, if pressing on the syringe plunger is difficult, that may indicate that the catheter tip is positioned against tissue, such as kidney mucosa, or otherwise obstructed. Moving the catheter distally a short distance can then free the catheter tip from the obstruction, as can be confirmed by the ease of infusing irrigation fluid (e.g., by the ease of pressing on a syringe plunger). Thus, some embodiments include utilizing feedback from the irrigation fluid flow to ensure that the vacuum tube will be unobstructed for aspiration.

Once suctioning is applied, the target calyx (e.g., the major calyx) may be swept to capture kidney stones. In some embodiments, the sweep comprises bending the distal end 106 of the catheter 102 within the target calyx in one or more directions. In some embodiments, the sweep comprises performing a complete revolution (360 degree) of the distal end 106 around a circular trajectory within the target calyx, the same as or similar to that described with respect to FIG. 16E. To perform the revolution the distal end 106 of the catheter may be bent in a first direction within the target calyx. Bending the distal end 106 in the first direction may comprise increasing or decreasing an angle of an existing bend in the catheter 102, which was imposed on the catheter 102 to navigate the distal end 106 into the target calyx. The bend in the first direction may be accomplished using one or more levers (e.g., levers 232, 233) on the handle 200, as described elsewhere herein, or another type of steering member. Once the bend in the first direction is in place, the catheter 102 may be rotated by rotating the handle 200 of the removal device 100. In some implementations, the handle 200 and catheter 102 may be rotated 360 degrees to complete the revolution. In some implementations, the catheter 102 may be rotated about 180 degrees in a first direction (e.g., clockwise or counterclockwise) to position the distal tip of the catheter 102 opposite its starting position relative to the unbent (with respect to the additional bend in the first direction) portion of the catheter 102. The catheter 102 may then be bent in a second direction, substantially opposite the first direction, using one or more levers or another type of steering member, to reposition the distal tip of the catheter 102 roughly at its starting position within the target calyx. The distal tip of the catheter 102 will create additional sweeping motions along a semi-arc trajectory, substantially normal to the plane of the revolution during the bending in the second direction. The amount of bending in the second direction may be approximately twice the amount of bending (e.g. twice the angle of bend) as was applied when bending in the first direction. The catheter 102 may then be rotated in a second direction, opposite the first direction of rotation, about 180 degrees to complete the entire revolution of the circular trajectory. Breaking the circular trajectory into two (or more) 180 degrees rotations in opposite directions may comprise easier hand motions for the user to operate the handle 200 to complete the revolution. The handle and operation of the catheter 102 may be designed so that the removal device 100 can be used in a highly ergonomic manner.

In some embodiments, the circular trajectory may be divided into more than two rotating movements (e.g., 90 degrees movements). The completion of the circular trajectory may comprise tracking the distal tip over overlapping portions of the trajectory. In some embodiments, the circular trajectory may be repeated (e.g., 1, 2, 3, or more than 3 times). The angle of the bending (e.g., in the first direction and the second direction) may be increased or decreased between repeated movements, such that the circular trajectory is larger or smaller and positioned more proximally or more distally within the target calyx. In some embodiments, the distal tip of the catheter 102 may be distally advanced or proximally retracted during and/or between repeated trajectory movements. In some embodiments, the distal tip is maintained in constant movement within the calyx, at least during suctioning. Once the sweeping procedure is completed, the distal end 106 of the catheter 102 may be withdrawn from the target calyx (e.g., by proximally retracting the handle 200). In some implementations, irrigation may be continually provided as the distal end 106 is withdrawn from the calyx. In some implementations, irrigation may be continually provided as the distal end 106 is withdrawn and inserted into the next target calyx. In some implementations, suction may be continually provided as the distal end 106 is withdrawn from the calyx. Application of suction during withdrawal from the calyx may capture any stones that might otherwise migrate into the calyx during removal of the distal end 106, or at least prevent the stones from migrating into the already swept calyx. The distal end 106 may be steered into the next target calyx and the sweeping procedure repeated. The steerability of the catheter 102 may allow navigation of the distal end 106 into the next calyx under indirect visualization (e.g., fluoroscopy) without use of a guidewire or direct visualization (e.g., an endoscope). The steerability may allow the distal end 106 to be navigated into any of the major calyces without use of a guidewire or direct visualization (e.g., an endoscope). The steerability may allow the distal end 106 to be navigated into any of the minor calyces without use of a guidewire or direct visualization (e.g., an endoscope). This sweeping procedure may be repeated until all of the kidney calyces have been swept. In some embodiments, each calyx is swept one time. In some embodiments, one or more of the calyces may be swept multiple times.

During use of the catheter 102, the vacuum lumen 114 may become clogged by stones and/or other debris which may prevent further aspiration of stones. Some tests have shown that catheters 102 may tend to become clogged near the distal end and/or near stepped changes in diameter within the handle. Stones of relatively oblong shapes, jagged profiles, and/or groups of stone having mixed sizes and/or dimensions may be particularly prone to causing clogs. The removal device 100 may include one or more features configured to indicate the presence of a clog to a user. For example, the pressure within the vacuum lumen 114 proximal to the obstruction should increase when the vacuum lumen 114 becomes clogged. The removal device 100 may include an electrical and/or mechanical pressure transducer or pressure gauge (e.g. a Bourdon tube) in fluid communication with the vacuum lumen 114 for monitoring pressure within the catheter 102 (e.g., proximal to the vacuum lumen 114). A pressure rise above a numerical level and/or above a marked level may indicate the presence of an obstruction. In some embodiments, the user may visually observe the indicated pressure rise and cease suctioning. In some embodiments, the removal device 100 may be configured to automatically shut off the negative pressure source upon detecting a rise above a maximum pressure (e.g., via the controller). In some embodiments, a simple binary mechanical indicator may alert the user of the presence of an obstruction. For example, the removal device 100 may comprise a pressure band. The pressure band may be removably coupled or attached to the removal device 100 such as along an aspiration line leading to the handle or any other suitable position configured to remain outside of the body. At least a portion of the pressure band may be placed in fluid communication with the vacuum lumen 114 when the pressure band is attached to the removal device 100. For instance, the pressure band may comprise a ring shape having a slit along its circumference that allows the pressure band to be placed over the aspiration line or a portion of the handle. The pressure band may be elastically deformable to fit over the aspiration line. The pressure band may be configured to cover and fluidly seal an opening in the aspiration line. When the pressure within the vacuum lumen 114 surpasses a threshold pressure, the pressure may elastically deform the pressure band causing it to decouple from the removal device, as an indicator that a clog has been detected. Once the obstruction is attended, the user may reapply the pressure band, which may be reusable. In some implementations, the clog may be audibly detectable. An operator may be able to audibly discern the difference between a higher flow rate when the vacuum lumen 114 is unclogged and a lower flow rate when the vacuum lumen 114 is clogged. The sound produced from aspiration may be louder when the vacuum lumen 114 is unclogged than when the vacuum lumen 114 is clogged. In some embodiments, the vacuum tube 110 (or a vacuum line coupled to the vacuum tube 110 such as through a proximal fluid port 222 of a handle 200) may comprise one or more small apertures that place the vacuum lumen 114 in fluid communication with the ambient environment. The apertures may be sized such that they do not significantly diminish the flow rate of the aspiration through the vacuum lumen 114 and/or create a significant decrease in pressure. In some implementations, the apertures may be configured to produce (e.g., whistle) or amplify the sound of suctioning such that an operator can audibly detect the presence of a clog.

In some embodiments, the catheter 102 may be moved through a prescribed range of motions that allows cleaning or clearing the catheter 102 when clogged, without removing the catheter 102 from the body. For instance, the catheter 102 may be moved into a position that substantially straightens the vacuum lumen 114 to remove any kinks and/or optimize pressure. The irrigation stream, in embodiments where possible, may be directed toward the aspiration port 116 to maximize pressure within the vacuum lumen 114. The distal end 106 of the catheter 102 may be moved away from tissue and the suction may be increased to de-clog the vacuum lumen 114. The vacuum lumen 114 may be temporarily placed in fluid communication with a positive pressure source (e.g., a syringe) rather than a negative pressure source, which may be temporarily turned off or disconnected. The positive pressure source may force a fluid (e.g., air or irrigation fluid) distally through the vacuum lumen 114 to dislodge the obstruction. The positive pressure may cause the obstruction to be moved distally out of the distal end of the catheter 102. In some embodiments, the handle 200 may comprise an additional fluid port 222 (e.g., a leur-connector port) for placing the vacuum lumen 114 in fluid communication with a positive pressure source. The catheter 102 may be withdrawn from the body and manually unclogged. In some embodiments, an obturator, such as obturator 400 described elsewhere herein or an obturator similar thereto, may be used to dislodge the obstruction, either ex situ or in situ. The unclogging obturator may be received in the vacuum lumen 114 through a proximal end of the removal device 100. The unclogging obturator may be used in situ (e.g., while the distal end of the catheter remains positioned inside the kidney) or on a catheter 102 that has been removed from the body. The unclogging obturator may be the same as or different from the obturator used to introduce the catheter into the body, if an obturator is used during the introduction. For example, an unclogging obturator may be relatively stiffer along its length than an introducing obturator to facilitate transmitting a distal pushing force on the obstruction. The unclogging obturator may be provided together with the removal device 100 (e.g., as part of a kit) or as a separate component. The distal end of the unclogging obturator may be flat, round, pointed, tapered, dome-shaped, bullet-shaped, etc. The unclogging obturator may comprise measurements or other markings along its length that are visible to a user along at least the portion extending from a proximal end of the removal device 100. The markings may indicate the relative distance into the catheter 102 that the distal end of the unclogging obturator has been inserted. A user may use the markings to approximate the location of the obstruction within the catheter 102. In some embodiments, the unclogging obturator may comprise a lumen (e.g., a central lumen) for receiving a guidewire. The guidewire may be axially translatable relative to the unclogging obturator. The guidewire may be used to exert force on the obstruction. The guidewire may have a relatively large cross-sectional area (e.g., the cross-sectional area may be maximized) or a relatively small cross-sectional area (e.g., the cross-sectional area may be minimized). In some embodiments, the vacuum tube 110 and/or the unclogging obturator may be mechanically oscillated or vibrated to facilitate loosening obstructions. In some embodiments, the unclogging obturator (or pusher) may comprise a small diameter wire (relative to the inner diameter of the vacuum lumen 114) or at least a small diameter wire extending distally from a larger diameter elongate body. The small diameter wire have sufficient rigidity to be pushed through the vacuum lumen and to dislodge a clog. In some implementations, particularly during an in situ unclogging, the small diameter wire may advantageously dislodge the clog and allow the debris (e.g., kidney stones) to continue to travel proximally through the vacuum lumen 114, since the small diameter wire does not substantially alter the entire cross sectional area of the vacuum lumen 114.

In some embodiments, a system is provided for guiding a clinician through a procedure. The system may include a display (e.g., a computer screen) for displaying information to the user. The display may be part of a controller, as described elsewhere herein. In some embodiments, the display may depict an anatomical representation of the body lumen in which the procedure is performed (e.g., the urinary tract). The display may depict actual visualization information (e.g., video image) retrieved from an imaging device (e.g., a ureteroscope) or representational information. The images may be real-time or obtained prior to performing the procedure. For example, the images may be obtained from an imaging device inserted into or along side the removal device 100, as described elsewhere herein. In some embodiments, the display may depict instructional information, textually or graphically (e.g., through symbols, pictures, or locations on a map) to the clinician. For example, the display may indicate the next physiological location for performing an operation (e.g., the next calyx). The anatomical location may be indicated on a map representation of the patient. Locations already operated on, the most recently operated on location, the next location to be operated on, and/or locations yet to be operated on may also be indicated (e.g., using different colors). In some implementations, the user may interact with the system, such as by inputting completion of an anatomical location (e.g., marking a checklist), and/or by marking locations which are to be operated on during or prior to the operation. The display or other portions of the system (e.g., a display on the device handle 200) may indicate operative values to the user. For instance, the display may indicate a pressure or flow value to the user, which, in some embodiments, may be modulated in real time by the user, such as through a button or finger port on the handle 200. In some embodiments, the system guides a clinician through the procedure by providing audio signals or instructions. For example, tones or verbal instructions may be provided to indicate that the clinician should perform a particular irrigation or aspiration sequence, move the catheter through a specific series of movements, or move to a different anatomical location.

In some embodiments, the removal system and/or removal device 100 may comprise a catheter 102 comprising suction and optionally irrigation, as described elsewhere herein, and an additional component configured to be positioned adjacent the catheter 102 within the body (e.g., the urinary tract). In some embodiments, the adjacent component may be coupled to the catheter 102 along the length of the catheter 102, along a portion of the length of the catheter 102, along a proximal portion of the catheter 102, and/or at the handle (e.g., sharing the same handle or having a separate handle coupled to the catheter 102 handle). In some embodiments, the adjacent component may not be coupled to the catheter 102 but may be delivered adjacent the catheter 102, simultaneously with the catheter 102, prior to delivering the catheter 102, or after delivering the catheter 102.

FIGS. 17A-17E schematically illustrate various examples of the additional component configured to be positioned adjacent the catheter 102. In some embodiments, the adjacent component may be a safety guidewire 302, as shown in FIG. 17A, which may be the same or similar to safety guidewires, particularly those for use in urology, known in the art. The safety guidewire 302 may provide, for example, quick emergency access to the urinary tract (e.g., the ureter or kidney) without necessitating the removal of the catheter 102 (which may provide access for a visualization tool, such as a ureteroscope, during an emergency procedure).

The safety guidewire 302 may also be used to introduce ancillary tools for use during the routine procedure (e.g., kidney stone removal procedure). In some embodiments, the safety guidewire 302 may be used to introduce or may be integral with an irrigation tube 130. The irrigation tube 130 may comprise a separate lumen, as described elsewhere herein, for receiving the safety guidewire 302 and a separate lumen for providing irrigation fluid or the irrigation lumen 134 may be used to receive the safety guidewire 302. The irrigation lumen 134 may have a cross sectional area larger than the cross-sectional area of the safety guidewire 302. The ancillary irrigation tube 130 may be the same as or similar to irrigation tubes 130 described elsewhere herein or comprise the same or similar features as irrigation lumens 134 described elsewhere herein. For example, the ancillary irrigation tube 130 may comprise distal irrigation ports 136 and/or lateral irrigation ports 136. The irrigation flow through the ancillary irrigation tube 130 may be controlled separately from irrigation and/or aspiration through the catheter 102 or may be by synchronized with the irrigation and/or aspiration through the catheter 102 according to any of the patterns described elsewhere herein. In some embodiments, the ancillary irrigation tube 130 may be advanced distally or retracted proximally relative to the catheter 102, such that irrigation stream of the ancillary irrigation tube 130 may be dynamically positioned relative to the one or more aspiration ports 116, such as during aspiration. In some embodiments, the ancillary irrigation tube 130 may be steerable (e.g., comprise a steerable distal portion) as described with respect to the catheter 102 elsewhere herein. Movement of the ancillary irrigation tube 130 in an axial, lateral, and/or rotational direction may be used to create more complex arrangements of the ancillary irrigation tube 130 with respect to the one or more aspiration ports 116 of the catheter 102. For example, the ancillary irrigation tube 130 may be bent in a substantially "c" shape configured to direct an ancillary irrigation stream toward the aspiration port 116 (e.g., from a lateral direction or a proximal and lateral direction), as schematically depicted in FIG. 17B. The ancillary irrigation tube 130 may be dynamically repositioned during the removal procedure. The ancillary irrigation tube 130 may be moved while the catheter 102 remains static or may move simultaneously with movement of the catheter 102, according to any of the motions described elsewhere herein. In some embodiments, the use of an ancillary irrigation tube 130 may allow use of a catheter 102 comprising no irrigation lumens 134. A catheter 102 comprising no irrigation lumens 134 may optimize the space available for the vacuum lumen 114 of the catheter 102, which may advantageously increase the suction generated by the catheter 102.

In some embodiments, the safety guidewire 302 may be used to introduce a shield 304 or may be integral with a shield 304. In some embodiments, the shield 304 may be positioned at the distal end of a tube comprising a lumen configured to receive and be advanced over the safety guidewire 302. In some embodiments, the shield 304 may comprise a mesh configured to allow fluid passage through the shield 304. The size of the mesh may be configured to prevent passage of kidney stones through the shield 304. In some embodiments, the mesh size may configured to contain or trap kidney stones of a certain size (e.g., large or medium) but to allow passage of kidney stones of a smaller size. In some systems, various shield 304 components of different configurations (e.g., mesh size, shield 304 shape, etc.) may be selectable to use with the catheter 102. The shield 304 may prevent movement of kidney stones from one calyx to another calyx. The shield 304 can make the use of irrigation which stirs up debris such as kidney stones more effective. In some implementations, the shield 304 may be configured to prevent the escape of kidney stones that have been moved (e.g., under the force of irrigation) toward one or more aspiration ports 116. For example, the shield 304 may be positioned on a proximal side of an aspiration port 116, as illustrated in FIG. 17C. In some embodiments, an edge of the shield 304 may intersect directly with or adjacent to an edge of an aspiration port 116 (e.g., a proximal edge of an aspiration port 116), such that the shield 304 guides kidney stones and/or other debris toward the aspiration port 116. The shield 304 may be configured with a conical shape or other curved shape. The shield 304 may have an increasing diameter or span as it extends in a distal and/or radially outward direction. In some embodiments, the shield 304 may be joined to the safety guidewire 302 or tube member (e.g., at a proximal end) around a portion of the circumference of the safety guidewire 302 or tube (e.g., 45 degrees, 90 degrees, 135 degrees, 180 degrees, 224 degrees, 270 degrees, etc.). The shield 304 may not be joined to the safety guidewire 302 or tube member along a portion of the circumference configured to sit or be positioned adjacent to the catheter 102, such that the shield 304 does not interfere with positioning the catheter 102 and ancillary device side-by-side. The circumferential span may remain constant, increase, or decrease as the shield 304 extends from the junction between the shield 304 and the tube member or guidewire. In some embodiments, the shield 304 may be configured to effectively wrap around the catheter 102, as shown in FIG. 17D, such that the shield 304 can extend along a greater portion or the entirety of the circumference of the catheter 102. In some implementations the shield 304 may be configured to wrap around the catheter 102 at a proximal portion of the catheter 102 positioned outside of the body and the shield 304 may serve to couple the ancillary device to the catheter 102. The shield 304 may be configured to be advanced (e.g., may slide) along the catheter 102 as it is introduced into the body. In some embodiments, the shield 304 may be positioned such that a distal end of the shield 304 extends beyond the distal end of the catheter 102. In some embodiments, the shield may curve inward toward the longitudinal axis or crossing the longitudinal axis of the catheter 102. The shield 304 may extend at least partially in front of a distal face of the catheter 102. In some embodiments, the shield 304 may have a curved or scooped shape.

In some embodiments, the shield 304 may have a collapsed configuration for introduction into the urinary tract an expanded configuration in which the shield 304 has a larger diameter and/or cross-sectional area, such as for use in the kidney (e.g., the renal pelvis, the major calyx, the minor calyx, etc.). FIG. 17E depicts an example of the shield in a collapsed configuration. The expansion and/or collapse of the shield 304 member may be controlled by pull wires 230, similar to those described elsewhere herein, or any other suitable mechanism, such as those known in the art. For example, a rod may be positioned within the tube member 305 of the shield device. The rod may be coupled to a distal end of the shield 304 such that advancement and retraction of the rod increases and decreases an effective length of the rod and expands and collapses the shield 304, respectively. The effective length of the rod may be transiently fixed using a screw mechanism or other suitable mechanism for holding the shield 304 in a particular configuration. In some embodiments, the effective length of the rod may be increased or decreased by rotating the rod. In some embodiments, the shield 304 may be fixed in a collapsed configuration, and expanded configuration, or in any intermediate configuration there between.

In some embodiments, the shield 304 may be solid. The shield 304 may be either rigid or flexible. In some embodiments, the shield 304 may comprise a metal material. In some embodiments, the shield 304 may comprise a polymer material or a polymer material may be used to coat the shield 304. In some embodiments, the shield 304 may be joined to the safety guidewire 302 or tube member 305 at a distal point and expand in a proximal and/or radially outward direction. For instance, the shield 304 may be positioned distally of an aspiration port 116, as illustrated in FIGS. 17C-17E. Irrigation may be directed in a substantially distal direction toward the aspiration port 116. In some embodiments, the shield 304 member may be coupled to or integrated with the ancillary irrigation tube 130 or other ancillary device. In some embodiments, the ancillary device may be a visualization device, such as a ureteroscope, which may facilitate visualization of the removal procedure.

Figure 18B:
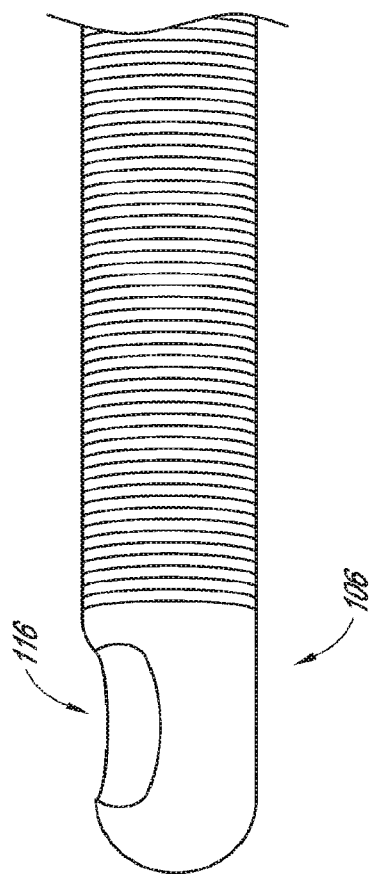
FIGS. 18A-18B illustrate an example of a distal end of a removal device comprising aspiration through a lateral aspiration port.
Figure 18A:
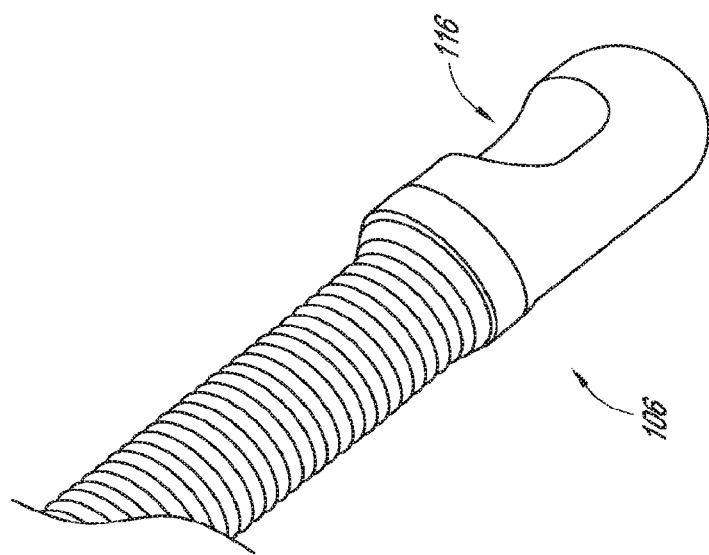

FIGS. 18A-18B illustrate images of a distal end 106 of an embodiment of the removal device 100. The distal end 106 may be the same as that depicted in FIG. 1. In some embodiments, the distal end 106 comprises a lateral aspiration port 116 and no distal-facing aspiration port. The distal end may have an atraumatic shape such as a rounded, domed, or bullet-shaped configuration. In some embodiments, the distal end 106 may have a flared or expanded diameter relative to a proximal portion of the catheter 102.

FIGS. 19A-19H schematically depict various positions of guidewires, delivery sheaths, and catheter 102 of the removal device 100 in a kidney. In some implementations, these positions may depict a general sequence of positions assumed by the devices throughout a kidney stone removal procedure. Various steps may be altered, omitted, and/or reordered. Additional positions not shown may also be employed. In some implementations, the kidney may first be inspected via a ureteroscope or other endoscope. The ureteroscope may be advanced into the kidney via a guidewire. The ureteroscope may be used to locate and/or count the kidney stones within the calyces of the kidney. In some implementations, a lithrotripsy device (e.g., a laser) may be inserted through the ureteroscope and used to break apart the kidney stones into smaller fragments. The ureteroscope may be removed prior to the next steps. In some implementations, a guidewire may remain positioned within the kidney.

Figure 19C:
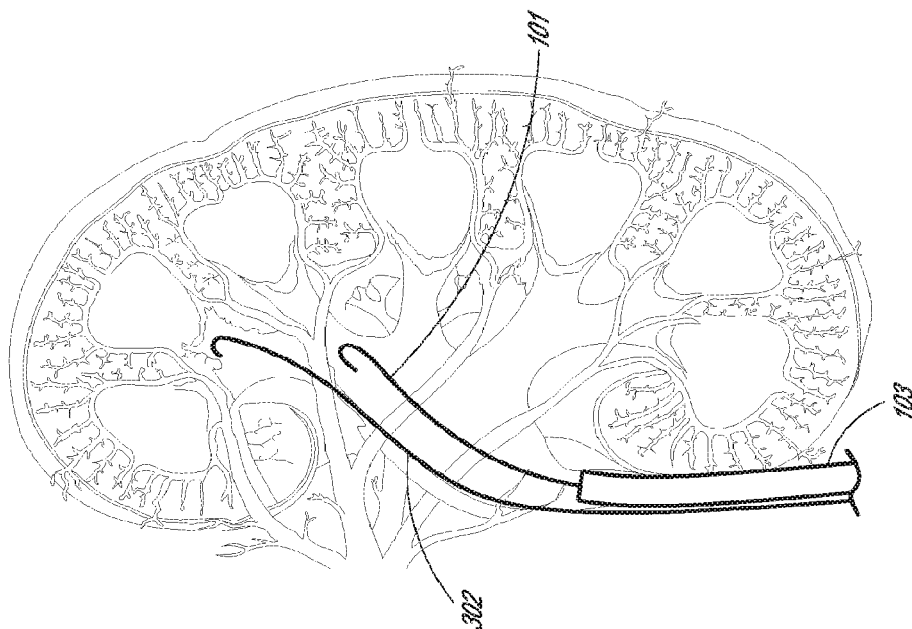
FIGS. 19A-19H schematically illustrate various positions of guide wires, delivery sheaths, and removal device catheters within a kidney.
Figure 19B:
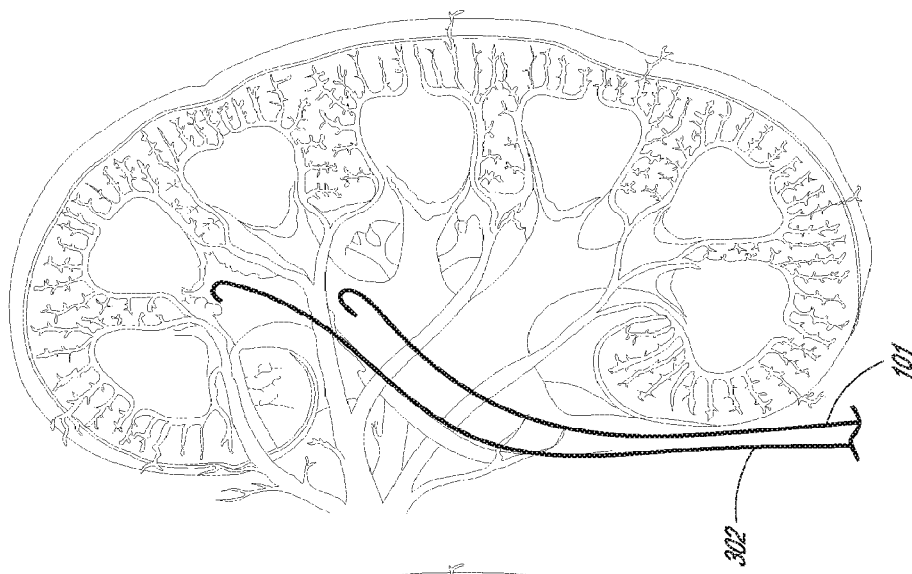
Figure 19A:
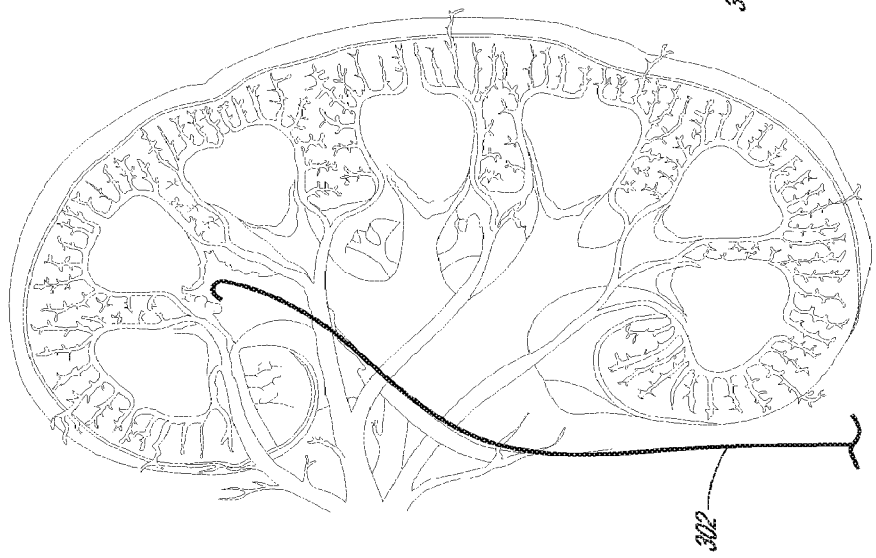
Figure 19F:
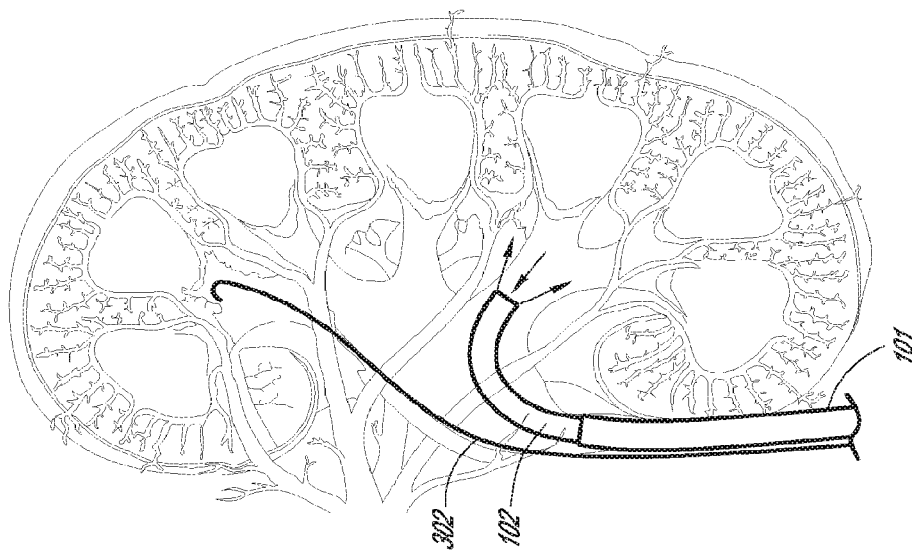
Figure 19E:
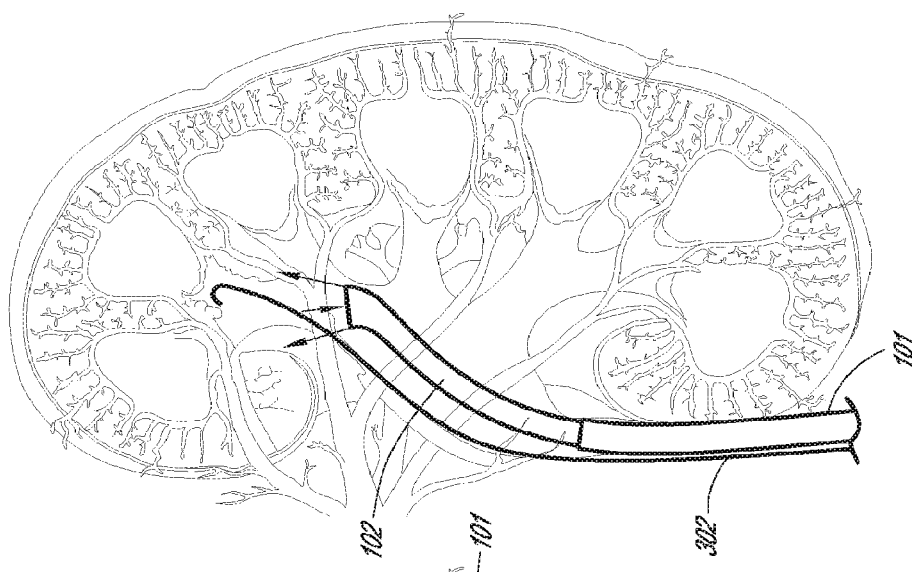
Figure 19D:
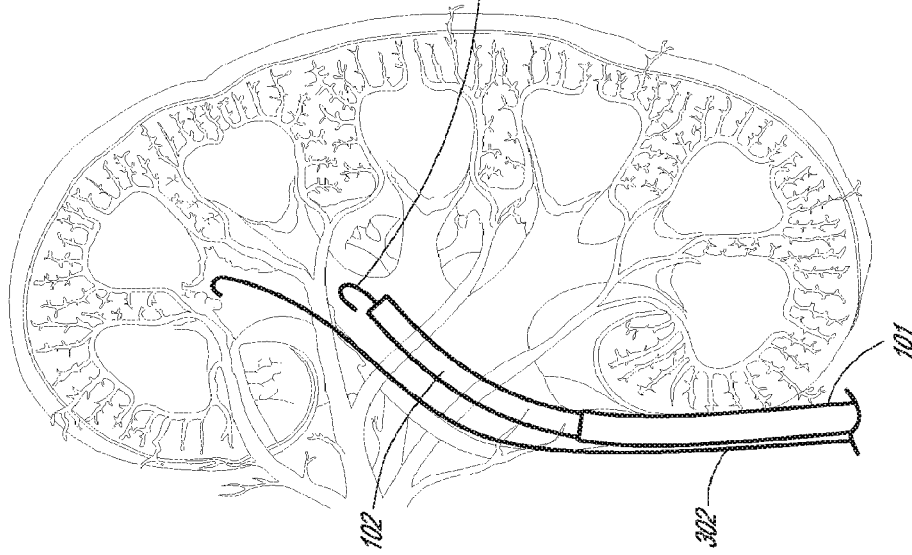
Figure 19H:
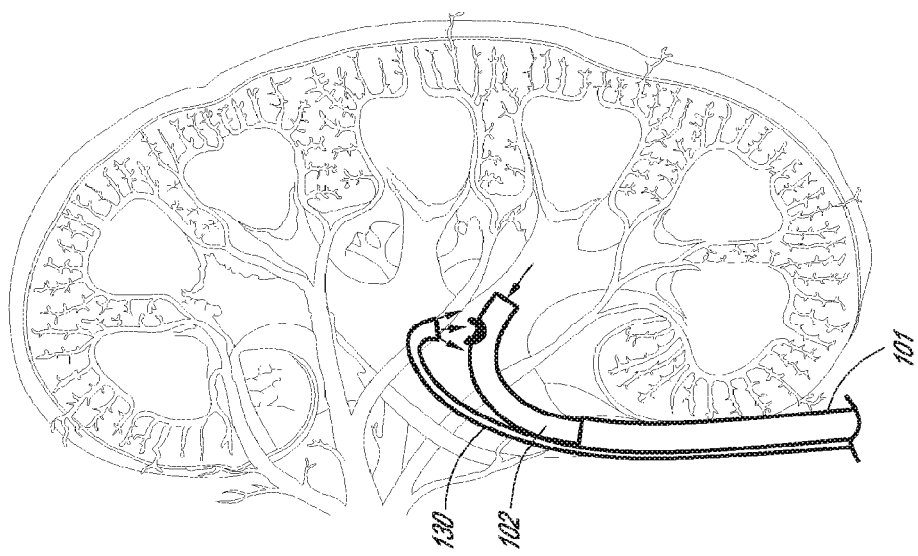
Figure 19G:
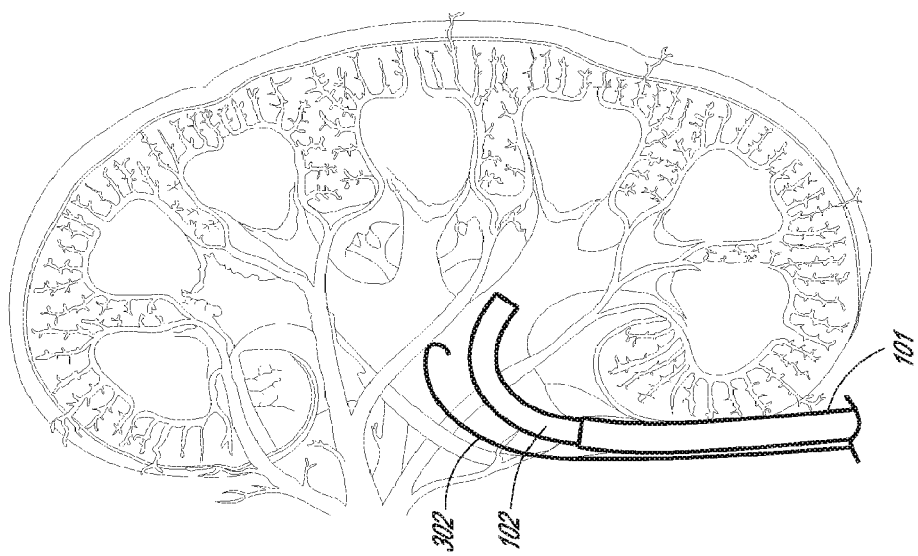

FIG. 19A depicts the insertion of a first guidewire into the kidney (e.g., a major calyx or pole of the kidney). The guidewire may be a safety guidewire 302, as shown and described elsewhere herein, or may be a primary guidewire 101 for delivery of the removal device. FIG. 19B depicts the insertion of a second guidewire into the kidney. The second guidewire may be a primary guidewire 101 as shown, or a safety guidewire 302. The first and second guidewires may be positioned within the same pole of the kidney, as shown, or may be positioned in different poles. FIG. 19C depicts the insertion of a delivery sheath 103 through the ureter. A delivery sheath 103 may be advanced over the primary guidewire 101 for introducing the catheter 102 into the urinary tract. The delivery sheath 103 may be advanced to a position such as the ureter, the renal pelvis, or past the renal pelvis. In some implementations, the delivery sheath 103 may be omitted altogether. The catheter 102 may be introduced via a guidewire. In some implementations, the catheter 102 may be introduced with the aid of an obturator, such as obturator 400 described elsewhere herein. The obturator may be received through the vacuum lumen 114 or another lumen of the catheter 102. The obturator may comprise a lumen for receiving the guidewire. The obturator may serve to fill the space or at least a portion of the space between the guidewire and the sidewall of the catheter 102, which may make it easier to track the catheter 102 over the guidewire. After the catheter 102 is positioned (e.g., within the kidney) the obturator may be proximally withdrawn, with or without the guidewire, so that the vacuum lumen 114 may be used for aspiration. FIG. 19D depicts the advancement of the catheter 102 distally beyond the distal end of the delivery sheath 103. In some embodiments, the catheter 102 may be advanced over the primary guidewire 101, as shown and as described elsewhere herein. In some embodiments, the catheter 102 may be advanced beyond the delivery sheath 103 without the use of the primary guidewire 101. The distal portion 106 of the catheter may be sufficiently steerable to navigate the catheter 102 beyond the delivery sheath 103 without the use of the primary guidewire 101. In some embodiments, the primary guidewire 101 may be removed from the delivery sheath 103 prior to advancement of the catheter 102. FIG. 19E depicts the catheter 102 being used to provide suctioning and irrigation in the upper pole. FIG. 19F depicts the repositioned catheter 102 providing suctioning and irrigation in the lower pole. The safety guidewire 302 may be repositioned substantially simultaneously with, prior to, or subsequently to the repositioning of the catheter 102. In some embodiments, the catheter 102 may be repositioned with the use of the primary guidewire 101. The primary guidewire 101 may be reinserted into the catheter 102, as described elsewhere herein, with or without an obturator, for repositioning the catheter 102 or, if never removed, may be advanced distally within the catheter 102. In some embodiments, the catheter 102 may be repositioned without the use of the primary guidewire 101. The catheter 102 may be repositioned by proximally retracting and/or distally advancing the catheter 102; by steering a distal end 106 of the catheter 102; and/or by rotating the catheter 102. FIG. 19G depicts the repositioning of the safety guidewire 302 to be substantially adjacent to catheter 102. FIG. 19H depicts the advancement of an ancillary device such as an irrigation tube 130 over the safety guidewire 302, as described elsewhere herein. As shown in FIG. 19H, the ancillary irrigation tube 130 may be used to advantageously direct irrigation fluid toward an aspiration port 116, such as a lateral aspiration port 116. In some embodiments, a safety guidewire 302 may be advanced into the kidney only when needed, such as after the advancement and potentially the initial use of the catheter 102. The devices may be removed from the body in any suitable order. For instance, the catheter 102 may be retracted into the delivery sheath 103 and removed together from the body. The ancillary device and/or safety guidewire 302 may be removed from the body following the removal of the catheter 102 or vice-versa.

In some embodiments, the catheter 102 may comprise a preformed shape (a non-linear shape). For instance, the distal end 106 of the catheter may be preformed with a curve. The pre-shaped catheter 102 may be steerable or non-steerable. The shape may resemble a shape of any configuration of a J-catheter for example. For example, the shape may resemble that of a Shirey transvascular catheter, a Brockenbrough transeptal catheter, a softip coronary catheter, hockey stick catheter, an Amplatz catheter, an EBU or Left Graft catheter, a IMA or XBRCA catheter, etc. In some embodiments, the catheter 102 may comprise a shape memory material (e.g., nitinol or another shape memory metal or a shape memory polymer), at least a long the pre-shaped portion. The transition temperature may be configured such that the catheter 102 assumes its preformed shape at physiological temperature, at room temperature, some temperature between, or below room temperature. In some implementations, the user may be able to customize the shape prior to use of the catheter 102 in the body. The shape of the catheter 102 may be reformable (e.g., by heating). The catheter 102 may cooperate with an outer sheath that is used to modulate the shape of the catheter 102. The outer sheath may be substantially linear or at least a shape different from the pre-formed catheter (e.g., straighter than the preformed catheter 102). The outer sheath may be more rigid than the flexible pre-shaped catheter 102 and may control the shape of the catheter 102, at least along portions of the length in which it surrounds the catheter 102. Thus, the shape of the pre-shaped catheter 102 may be effectively controlled (e.g., effectively straightened) by advancing the outer sheath over the shaped portion of the pre-shaped catheter 102. The adjustability of the shape may be used to facilitate navigating the pre-shaped catheter 102 into the calyces of the kidney. For example, the catheter 102 may be introduced through the ureter along with the outer sheath such that the catheter 102 is straight. Once the distal end 106 of the catheter 102 is positioned in the renal pelvis, the outer sheath may be retracted relative to the catheter 102 and/or the catheter may be advanced relative to the outer sheath to expose the pre-curved portion of the catheter 102. The catheter 102 may assume a tighter bend (smaller radius of curvature) the larger the length of the catheter 102 that is exposed from the outer sheath. Thus, the appropriate angle of bend may be achieved by selectively extending the catheter 102 from the outer sheath a given distance. The appropriate angle of bend may be chosen for navigating the catheter into each of the calyces.

In some embodiments, a stone collection container or line-trap may be positioned in-lie between the vacuum source and the handle 200 of the removal device. The collection trap may be configured to collect kidney stones that are aspirated through the removal device 100. For example, the collection trap may comprise a closed container (maintaining the vacuum seal) in which an inlet line extends from the handle 200 to the collection strap (it may extend into the collection trap) and an outlet line extends from the collection trap to the vacuum source (it may extend into the collection trap). The outlet line may be positioned at a top end of the collection trap or elsewhere on the collection trap. The inlet line may be positioned at a top end of the collection trap. Gravity may be used collect stones in the bottom of the collection trap. For example, the collection trap may substantially resemble the stone catcher of the Lithoclast Ultra Collection Device™. The collection trap may be used to evaluate the removed stones and/or for reconciliation (e.g., counting or weighing) of the collected stones to determine the efficacy or completion of the treatment. In some embodiments, the collection trap may be positioned upstream of an aspiration line. For example, the collection trap may be connected directly to or positioned near a hospital wall-mounted suction outlet. The collection trap may be self-supporting and may rest on the ground or a cart or may be supported by the wall when attached to a wall outlet. There may be a sufficient length of flexible aspiration line between the collection trap and the removal device 100. In some embodiments, the collection trap may be rigidly attached to the handle of the removal device 100. For instance, the collection trap may be supported on a proximal end of the handle and may connect to a fluid port 222. An aspiration line may extend from the collection canister to the negative pressure source. In some embodiments, the collection canister may be disposable. In some embodiments, the collection canister may be reusable. The collection canister may be used with a disposable interior liner if reused that may make disposal of the contents after a procedure readily disposable.

In some embodiments, the collection trap may comprise indicators configured to provide information related to the weight, color, and/or size of the collected stones. For example, the collection trap may include one or more size filters (e.g., meshes). A size filter may be positioned at the outlet (which may, for example, be positioned at the bottom end of the device rather than the top end) which allows only for the collection of stones greater than a threshold size. Alternatively, one or more size filters may be positioned at the bottom of the collection trap such that smaller stones fall deeper into the bottom of the collection container, while larger stones are collected closer to the top of the container. The one or more filters may act to effectively sieve the collected stones. In some embodiments, the collection trap or at least a portion thereof (e.g., a bottom portion) is configured to rotate and may act as a centrifugal force trap. In some embodiments, the collection trap may be coupled to a scale that monitors the mass of the collected stones within the collection trap. In some embodiments, reagents (e.g., colorimetric reagents) may be stored in the bottom of the collection trap and may react with the collected stone to produce observable colorimetric changes depending on a property (e.g., a chemical property) of the collected stones. In some embodiments, the collection trap (which may be at least partially transparent) may be coupled to a spectrophotometer, fluorescence detector, or other optic measurement device. Assessing color information about the irrigation fluid may be useful for determining physiological information such as potential hematuria in the kidney. The collection trap may be used to monitor outflow from the kidney and thereby provide an additional safety mechanism. Other suitable indicators may be used as well.

FIGS. 20A-20D schematically illustrates the dimensions and configuration of an example of an obturator 400 configured to be used with the removal device 100. FIG. 20A illustrates a side view of the obturator 400. FIG. 20B illustrates a distal end view of the obturator 400. FIG. 20C illustrates a cross section of a proximal end of the obturator 400. FIG. 20D illustrates a cross section of a distal end of the obturator 400. The obturator 400 may be configured to be received within the vacuum lumen 114 of the vacuum tube 110. The obturator 400 may comprise a tapered distal end 406, as shown in FIGS. 20A and 20D. The obturator 400 may comprise a fluid port, such as a luer fitting (e.g, a clear polycarbonate female luer fitting) at its proximal end 404. The obturator 400 may comprise a lumen 402 extending from the proximal end 404 to the distal end 406. The lumen 402 may be configured for receiving a guidewire. In some embodiments, the obturator (e.g., over a guidewire) may be used to facilitate in placing the catheter 102 in the kidney and potentially at least in one of the target calyces (e.g., the initial target calyx) before being removed. The obturator may be relatively flexible. For example, the obturator may be about 25D, 30D, 35D, 40D, less than 25D, more than 40D, or a durometer selected from a range there between. In some embodiments, the obturator may comprise PEBAX® or another suitable material. In some embodiments, the obturator 400, or portions thereof, may be translucent. In some embodiments, the obturator 400, or portions thereof, may be radiopaque. The obturator 400 may be configured to lock into place with the handle 200 of the removal device. The obturator 400 may comprise one or more wings 403 at the proximal end 404.

In some embodiments, the catheter 102 and/or the obturator 400 may be configured to vibrate. In some implementations, vibrations from the obturator 400 may be transferred to the catheter 102 when the obturator 400 is inserted, at least partially, into the catheter 102. Vibration of the catheter 102 and/or the obturator 400 may facilitate navigation of the removal device 100 through the urethra, ureter, and/or other body canals, particularly where the body canal is narrow and/or tortuous. Vibration of the catheter 102 and/or an obturator 400 inserted through the catheter 102 to a location proximal to a clog in the vacuum lumen 114 may help dislodge a clog in the lumen 114. In some embodiments, the handle 200 may comprise a motor or other electromechanical mechanism for initiating the vibrations. In some embodiments, an ancillary vibratory device may be coupled outside of the body to a proximal end of the catheter 102 (e.g., distal to strain relief 226) and/or proximal end of the obturator 400 (e.g., proximal to handle 200). With respect to the catheter 102, the vibratory device may vibrate the vacuum tube 110 and/or the irrigation tube 130. The vibrations may propagate from a proximal end of the shaft(s) toward a distal end of the shaft(s). In some embodiments, the sidewall of one or more shafts may comprise relatively rigid elements (e.g., structural support elements such as coils) which are prone to vibration. For example, the rigid elements may be metal (e.g., stainless steel). These rigid elements may extend from a proximal end to or toward a distal end of the shaft(s). In some embodiments, the vibration may be applied directly to the rigid element. For instance, in some embodiments, the rigid element may protrude proximally from the polymer layers of the sidewall of the one or more shafts.

The embodiments disclosed herein are not necessarily limited to use for removal of kidney stones and/or removal of kidney stones from the kidney through the ureter. For example, the devices, systems, and methods described herein may also be applied to applications such as nephroscopy and percutaneous nephrolithotomy, in which stones are moved via a puncture wound in the kidney through a minimally invasive procedure. In some implementations, the size (e.g., diameter) of the removal device 100 may be increased (e.g., an outer diameter of 10 mm or grater) if used percutaneously to accommodate larger stones and/or to accommodate a direct visualization device (e.g., a ureteroscope). The removal device 100 may comprise the same or similar functionalities, including steerability.

Example

A prototype removal device was tested in a live pig model. Notably, a pig kidney has a more tortuous anatomy with shallower/shorter/narrower/smaller calyces than a human kidney, which is expected to make isolation of stones within the pig calyces more difficult since they can easily escape from the calyx during the procedure. Pigs also have more calyces than humans. Also, the upper and lower poles of the pig kidney are oriented at significantly more severe angles to the ureter than the angles of a human kidney. The prototype comprised a steerable distal portion and a single distal-facing aspiration port in fluid communication with a single finger port suction valve on the handle for controlling suctioning. The 12 Fr catheter comprised a large aspiration lumen concentrically surrounded by an irrigation lumen.

A female pig was positioned in a supine or flat position (not in a Trandelenburg or reverse Trandelenburg position). Cystoscopy and ureteroscopy (with a flexible Storz™ ureteroscope) were initially performed on the pig subject. The procedure was also monitored under fluoroscopy using a contrast agent. A 0.035 inch sensor guidewire was placed into the target kidney. A 36 cm 12/14 Fr (inner diameter/outer diameter) access sheath was introduced. An obturator was inserted into the aspiration lumen of the catheter and the obturator and catheter were advanced over the guidewire. In some test runs, the catheter was advanced into the target calyx of the right or left pig kidney, and, upon placement of the catheter, the guidewire and obturator were removed from the catheter to measure the time required to successfully deliver the device (the deliverability). In other test runs, kidney stone fragments sized approximately 1 mm and 2 mm, or aluminum balls of the same size, were loaded into the target calyx via a basket using the access sheath, the scope, and/or the obturator. The placement within the calyces of the kidney were confirmed via ureteroscope, after which a guide wire was introduced into the calyx and the scope was removed. The aluminum balls were shaped into more oblong conformations that more accurately reflect stone fragments, since perfectly spherical objects are expected to be more difficult to aspirate. The aluminum balls are visible on fluoroscopy and allowed tracking of the migration of the balls. The balls were reported to float more easily than human kidney stones and to more readily migrate from their original location than human kidney stones. The successful placement of the kidney stone fragments in the target calyx was inspected and confirmed via the ureteroscope. The catheter was then advanced over the guidewire into the target calyx and the obturator and guidewire were removed. The catheter was connected to a syringe (Boston Scientific Single Action Pumping System or SAPS™) as a source of irrigation and a vacuum source generating a pressure of 150 mm Hg and continuous irrigation (10 cc at a time) and suction, modulated by the physician via the finger hole, were initiated within the target calyx to collect the kidney stone fragments under a blind procedure (the kidney stone fragments are not visible via fluoroscopy). The small amount of irrigation fluid delivered was removed with each cycle of suctioning to prevent over-pressurization of the kidney. During the procedure with the human kidney stones, each calyx was swept under fluoroscopy moving from the upper calyx to the lower calyx. Contrast agent was used to facilitate improved visualization of the kidney's anatomy. Upon completion of a sweeping procedure, the catheter was removed from the pig and the stone fragments captured were collected from the aspiration waste and counted. The catheter was inspected for any clogging or kinking. The ureteroscope was reintroduced into the kidney and the kidney was inspected for tissue damage and residual stones.

In a first test, 6 out of 10 2 mm aluminum balls were successfully placed in the upper, middle, and lower calyces of the left kidney. Several of the stones had quickly migrated from the middle calyx to the lower calyx. The 10 aluminum balls comprised a mass of 95 mg. Initially, the aluminum balls were attempted to be removed using a flexible catheter of similar construction as described above, except that the catheter was non-steerable. The flexible catheter was unable to access any of the pig calyces at its given flexibility. Irrigation flow pressure was increased to attempt to create a vortex effect from within the renal pelvis. The non-steerable catheter removed 0 of 6 aluminum balls after applying 200 cc of total irrigation volume. The procedure, from the initiation of suction and irrigation to the removal of the catheter lasted 3 minutes 10 seconds. The procedure resulted in additional migration of the stones, including one stone to the upper calyx and another deep into the lower calyx. Afterwards, removal was attempted using the steerable catheter. A total irrigation volume of 240 cc was applied and 4 of the 6 aluminum balls were successfully removed from the calyces without any clogging of the catheter. The two unremoved aluminum balls were those that had migrated during the procedure with the non-steerable catheter. The procedure, from the initiation of suction and irrigation to the removal of the catheter lasted 2 minutes 50 seconds.

In a second test, 9 out of 10 2 mm stone fragments were successfully placed in the middle calyx, with a few of the fragments quickly migrating to the upper calyx of the right kidney. The 10 fragments comprised a total mass of 67 mg. A total irrigation volume of 120 cc was applied and 9 of the 9 stone fragments were successfully removed from the calyces without any clogging of the catheter. The procedure, from the initiation of suction and irrigation to the removal of the catheter lasted 2 minutes 15 seconds.

In a third test, 8 of 10 stone fragments were successfully placed in the upper and middle calyces of the right kidney—2 in the upper calyx and 6 in the middle calyx. The 10 fragments comprised a total mass of 67 mg. A total irrigation volume of 250 cc was applied and 8 of the 8 stone fragments were successfully removed from the calyces without any clogging of the catheter. The procedure, from the initiation of suction and irrigation to the removal of the catheter lasted 3 minutes 10 seconds.

The catheter was able to access all of the kidney's calyces within a span of 30 seconds. The catheter was able to be easily navigated into the anterior and posterior calyces of each major calyx. The physician was able to confirm minimal tissue damage during the procedure by monitoring the color (i.e. the amount of blood) in the irrigation fluid that exited via the finger port via passive outflow when the kidney pressure rose with the addition of the irrigation fluid. No perforation, tearing, or bleeding of the kidney was observed to be associated with the procedure. Safe suctioning within the kidney was achieved with using no more than 240 cc irrigation fluid in each procedure.

The tests showed that the procedure was successfully performed with no direct visualization using a scope, under standard fluoroscopy. Using fluoroscopy, the physician was able to access each calyx within 30 seconds and the entire procedure took an average of 2 minutes to complete. The absence of a scope inside the aspiration lumen during the procedure was highly advantageous in that it maximized the patency of the aspiration lumen during aspiration. The absence of a scope is expected to allow larger fragments to be removed than when a scope is used. The physician noted the steerable catheter was easy to use and similar to operating a flexible ureteroscope.

It is understood that this disclosure, in many respects, is only illustrative of the numerous alternative device embodiments of the present invention. Changes may be made in the details, particularly in matters of shape, size, material and arrangement of various device components without exceeding the scope of the various embodiments of the invention. Those skilled in the art will appreciate that the exemplary embodiments and descriptions thereof are merely illustrative of the invention as a whole. While several principles of the invention are made clear in the exemplary embodiments described above, those skilled in the art will appreciate that modifications of the structure, arrangement, proportions, elements, materials and methods of use, may be utilized in the practice of the invention, and otherwise, which are particularly adapted to specific environments and operative requirements without departing from the scope of the invention. In addition, while certain features and elements have been described in connection with particular embodiments, those skilled in the art will appreciate that those features and elements can be combined with the other embodiments disclosed herein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of removing kidney stones from a kidney of a patient, the method comprising:
    inserting a steerable distal portion of a catheter system through the urethra, bladder, and ureter and into the kidney, the distal portion comprising a vacuum lumen and an irrigation lumen, wherein a distal face of the distal portion comprises (i) an aspiration port and (ii) a plurality of irrigation ports in fluid communication with the irrigation lumen, wherein the aspiration port has an inner diameter larger than the inner diameter of any one of the plurality of irrigation ports;
    irrigating the kidney by applying irrigation fluid at a flow rate in a first flow rate range through the irrigation lumen and out from at least one of the irrigation ports;
    inserting the distal portion into a first calyx of the kidney;
    applying irrigation fluid at a flow rate in a second flow rate range through the irrigation lumen and out from at least one of the irrigation ports;
    removing kidney stones from the first calyx by applying suction through the vacuum lumen;
    applying irrigation fluid at the flow rate or a different flow rate in the second flow rate range through the irrigation lumen and out from at least one of the irrigation ports;
    steering the distal portion within the first calyx by manipulating a wire pull member of a proximal handle portion of the catheter system, the wire pull member attached to a plurality of pull wires running from the distal portion to the wire pull member, wherein pulling on one or more the pull wires using the wire pull member causes the distal portion to bend;
    removing the distal portion from the first calyx;
    inserting the distal portion into a second calyx of the kidney; applying irrigation fluid at the flow rate or a different flow rate in the first flow rate range through the irrigation lumen and out from at least one of the irrigation ports;
    removing kidney stones from the second calyx by applying suction through the vacuum lumen;
    applying irrigation fluid at the flow rate or a different flow rate in the second flow rate range through the irrigation lumen and out from at least one of the irrigation ports; and
    steering the distal portion within the second calyx by manipulating the wire pull member.

2. The method of claim 1, wherein irrigation fluid is applied continuously at the flow rate or a different flow rate in the first flow rate range through the irrigation lumen while the distal portion of the catheter is removed from the first calyx and inserted into the second calyx.

3. The method of claim 1, further comprising:
    after inserting the distal portion into the kidney, continuously applying irrigation fluid through the irrigation lumen and out from at least one of the irrigation ports into the kidney until irrigation fluid returns through the vacuum lumen to outside of the patient.

4. The method of claim 1, further comprising:
after inserting the distal portion into the first calyx, continuously applying irrigation fluid through the irrigation lumen and out from at least one of the irrigation ports into the kidney until irrigation fluid returns through the vacuum lumen to outside of the patient.

5. The method of claim 1, further comprising:
after inserting the distal portion into the second calyx, continuously applying irrigation fluid through the irrigation lumen and out from at least one of the irrigation ports into the kidney until irrigation fluid returns through the vacuum lumen to outside of the patient.

6. The method of claim 1, further comprising:
removing the distal portion from the second calyx and inserting the distal portion into an additional calyx of the kidney;
applying irrigation fluid at the flow rate or a different flow rate in the first flow rate range through the irrigation lumen and out from at least one of the irrigation ports;
removing kidney stones from the additional calyx by applying suction through the vacuum lumen;
applying irrigation fluid at the flow rate or a different flow rate in the second flow rate range through the irrigation lumen; and
steering the distal portion within the additional calyx by manipulating the wire pull member.

7. The method of claim 6, wherein the first calyx, the second calyx, or the additional calyx includes a calyx within a lower pole of the kidney.

8. The method of claim 1, wherein the catheter system is configured to allow kidney stone transport through the vacuum lumen when the distal portion is bent to form a curve in the range of about 100 degrees to about 200 degrees.

9. The method of claim 1, wherein the irrigation lumen is fixed with respect to the vacuum lumen.

10. The method of claim 1, wherein at least one of the plurality of irrigation ports is configured to create an irrigation stream that extends radially outward away from a longitudinal axis of the distal portion.

11. The method of claim 10, wherein all of the plurality of irrigation ports are configured to create the irrigation stream that extends radially outward away from the longitudinal axis of the distal portion.

12. The method of claim 1, wherein the plurality of irrigation ports are configured to create an irrigation stream that diverges away from a longitudinal axis of the distal portion.

13. The method of claim 1, further comprising a nozzle incorporated into the distal portion and the nozzle forms the distal face of the distal portion.

14. The method of claim 1, wherein the vacuum lumen has an inner diameter greater than 2 mm.

15. The method of claim 1, wherein the vacuum lumen has an inner diameter of about 2.5 mm.

16. The method of claim 1, wherein the catheter system further comprises a direct visualization device configured to be movable within the vacuum lumen and inserting the distal portion into the kidney, first calyx, or second calyx is done while visualizing the kidney, first calyx, or second calyx using the direct visualization device.

17. The method of claim 16, wherein the direct visualization device is configured to be removed from within the vacuum lumen prior to kidney stone transport through the vacuum lumen.

18. The method of claim 17, further comprising removing the direct visualization device from within the vacuum lumen prior to removing kidney stones from the first calyx and replacing the direct visualization device into the vacuum lumen prior to inserting the distal portion into the second calyx.

19. The method of claim 1, wherein the first flow rate range is from about 5 ml/min to about 20 ml/min.

20. The method of claim 1, wherein the second flow rate range is from about 50 ml/min to about 200 ml/min.

* * * * *